(12) United States Patent
Zhu et al.

(10) Patent No.: US 10,994,031 B2
(45) Date of Patent: May 4, 2021

(54) COMPOSITES AND COMPOSITIONS FOR THERAPEUTIC USE AND METHODS OF MAKING AND USING THE SAME

(71) Applicant: Board of Regents of the Nevada System of Higher Education, on behalf of the University of Nevada, Reno, NV (US)

(72) Inventors: Xiaoshan Zhu, Reno, NV (US); Violeta Demillo, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 434 days.

(21) Appl. No.: 15/872,763

(22) Filed: Jan. 16, 2018

(65) Prior Publication Data

US 2018/0154024 A1    Jun. 7, 2018

Related U.S. Application Data

(63) Continuation-in-part of application No. PCT/US2016/042613, filed on Jul. 15, 2016.
(Continued)

(51) Int. Cl.
*A61K 9/00* (2006.01)
*A61K 49/00* (2006.01)
(Continued)

(52) U.S. Cl.
CPC ............ *A61K 49/0067* (2013.01); *A61K 9/48* (2013.01); *A61K 49/0002* (2013.01);
(Continued)

(58) Field of Classification Search
CPC .................................................. A61K 49/0067
See application file for complete search history.

(56) References Cited

U.S. PATENT DOCUMENTS 4,416,668 A    11/1983 Thompson
8,940,333 B2    1/2015 Hsieh et al.
(Continued)

FOREIGN PATENT DOCUMENTS

| WO | WO 2007/024393 | 3/2007 |
| WO | WO 2011/119654 A1 | 9/2011 |
| WO | WO 2013/182707 | 12/2013 |

OTHER PUBLICATIONS

Shrake et al., "Facilitated preparation of bioconjugatable zwitterionic quantum dots using dual-lipid encapsulation," *Journal of Colloid and Interface Science*, vol. 437, pp. 140-146, Sep. 21, 2014.
(Continued)

*Primary Examiner* — Paul W Dickinson
(74) *Attorney, Agent, or Firm* — Klarquist Sparkman, LLP

(57) ABSTRACT

Disclosed herein are embodiments of composites and compositions that can be used for therapeutic applications in vivo and/or in vitro. The disclosed composites can comprise cores having magnetic nanoparticles, quantum dots, or combinations thereof and zwitterionic polymeric coatings that facilitate solubility and bioconjugation. The compositions disclosed herein can comprise the composites and one or more biomolecules, drugs, or combinations thereof. Also disclosed herein are methods of making the composites, composite components, and methods of making quantum dots for use in the composites.

19 Claims, 46 Drawing Sheets

Related U.S. Application Data

(60) Provisional application No. 62/569,291, filed on Oct. 6, 2017, provisional application No. 62/203,325, filed on Aug. 10, 2015, provisional application No. 62/194,122, filed on Jul. 17, 2015.

(51) Int. Cl.
  *A61K 49/18*  (2006.01)
  *A61K 9/48*  (2006.01)
  *G01N 33/58*  (2006.01)
  *B82Y 5/00*  (2011.01)

(52) U.S. Cl.
  CPC ...... *A61K 49/0056* (2013.01); *A61K 49/1866* (2013.01); *A61K 49/1887* (2013.01); *G01N 33/587* (2013.01); *G01N 33/588* (2013.01); *B82Y 5/00* (2013.01)

(56) References Cited

U.S. PATENT DOCUMENTS

| | | |
|---|---|---|
| 2011/0014296 A1 | 1/2011 | Chen et al. |
| 2012/0067821 A1 | 3/2012 | Chang et al. |

OTHER PUBLICATIONS

Zhang et al., "Self-assembly multifunctional nanocomposites with Fe3O4 magnetic core and CdSe/ZnS quantum dots shell," *Journal of Biomedical Research Part A*, pp. 840-846, Oct. 29, 2007.

Extended European Search Report issued for EPC Application No. 16828325.7 dated Jan. 24, 2019.

Demillo et al., "Zwitterionic amphiphile coated magnetofluorescent nanoparticles-synthesis, characterization and tumor cell targeting," *Journal of Materials Chemistry B*, 3(42): 8328-8336, Sep. 14, 2015.

Examination Report issued by European Patent Office dated Nov. 6, 2019, for EPC Application No. 16828325.7.

International Search Report and Written Opinion issued for International Application No. PCT/US2016/042613 dated Oct. 18, 2016.

Chen et al., "Thermal decomposition based synthesis of Ag—In—S/Zns quantum dots and their chlorotoxin-modified micelles for brain tumor cell targeting," *RSC Adv.*, 74(5): 60612-60620, Jul. 8, 2015.

Huang et al., "A polymer encapsulation approach to prepare zwitterion-like, biocompatible quantum dots with wide pH and ionic stability," *J. Nanopart. Res.*, 16(8): 2555, Jul. 19, 2014.

Demillo et al., "Fabrication of $MnFe_2O_4$—$CuInS_2$/ZnS magnetofluorescent nanocomposites and their characterization," *Colloids and Surfaces A: Physicochemical and Engineering Aspects*, 464(5): 134-142, Oct. 16, 2014.

Cormode et al., "A versatile and tunable coating strategy allows control of nanocrystal delivery to cell types in the liver," *Bioconjug. Chem.*, 22(3): 353-361, Mar. 16, 2011.

Tarannum et al., "Advances in synthesis and applications of sulfo and carbo analogues of polybetaines: a review," *Reviews in Advanced Sciences and Engineering*, 2(2): 90-111, Jun. 2013.

Han et al., "Spatial charge configuration regulates nanoparticle transport and binding behavior in vivo," *Angew Chem Int Ed Engl.*, 52(5): 1414-1419, Jan. 28, 2013.

Wu et al., "Carboxybetaine, sulfobetaine, and cationic block copolymer coatings: a comparison of the surface properties and antibiofouling behavior," *Journal of Applied Polymer Science*, 124(3): 2154-2170, May 5, 2012.

Kober et al., "Transient magnetic birefringence for determining magnetic nanoparticle diameters in dense, highly light scattering media," *Nanotechnology*, 23(15): 25 pages, Mar. 28, 2012.

Jiang et al., "An effective polymer cross-linking strategy to obtain stable dispersions of upconverting $NaYF_4$ nanoparticles in buffers and biological growth media for biolabeling applications," *Langmuir*, 28(6): 3329-3247, Jan. 17, 2012.

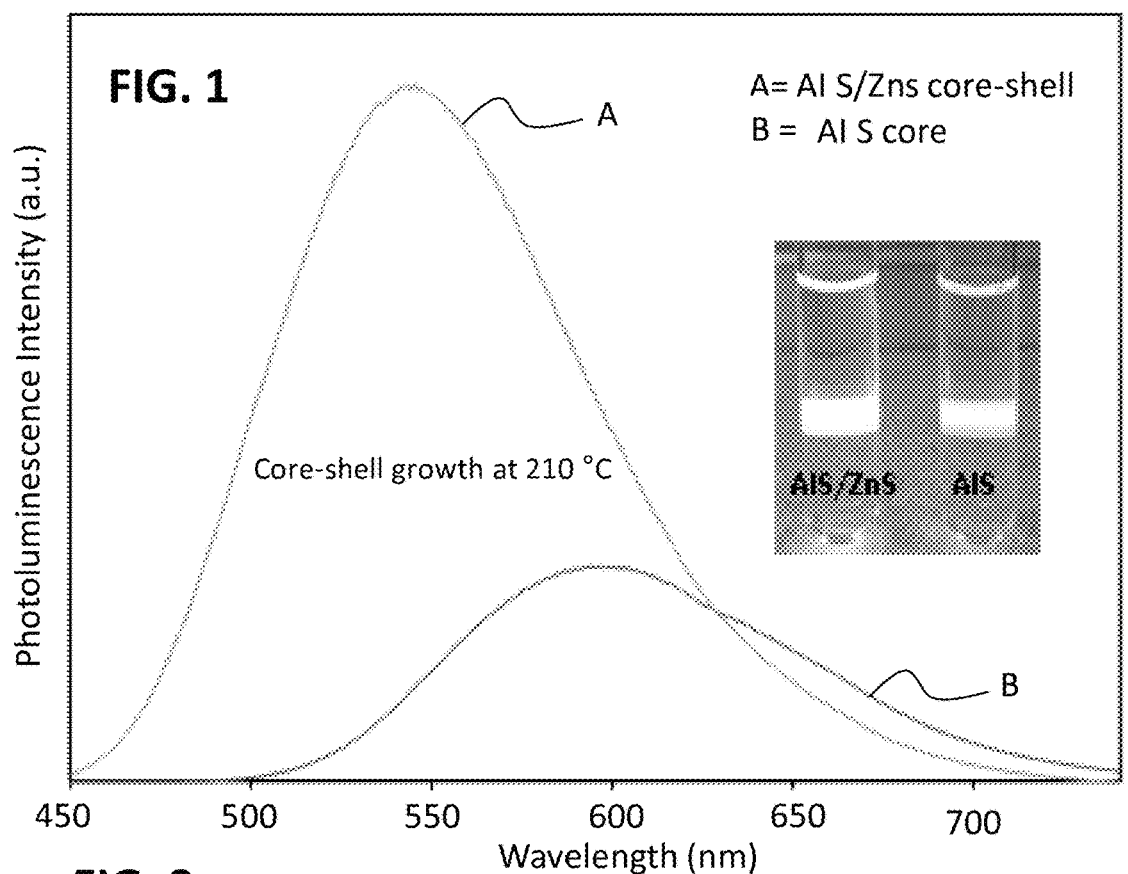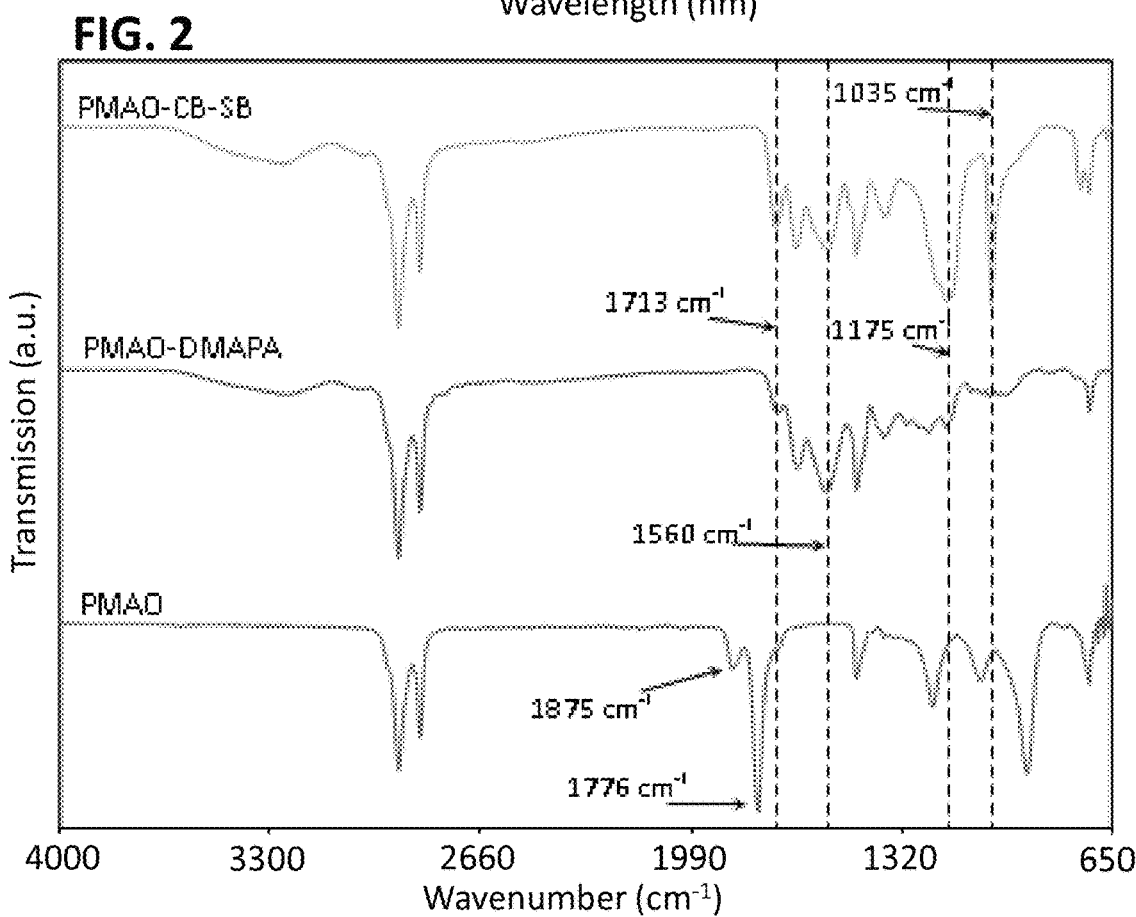

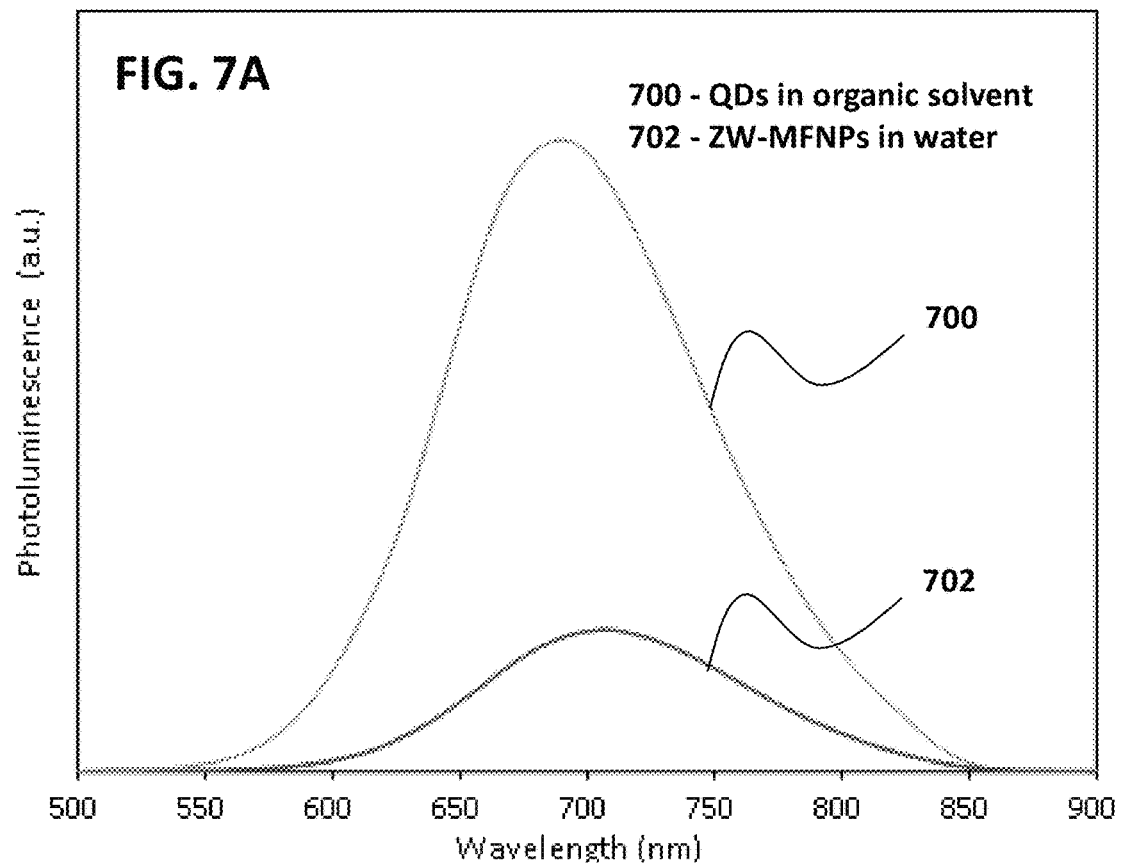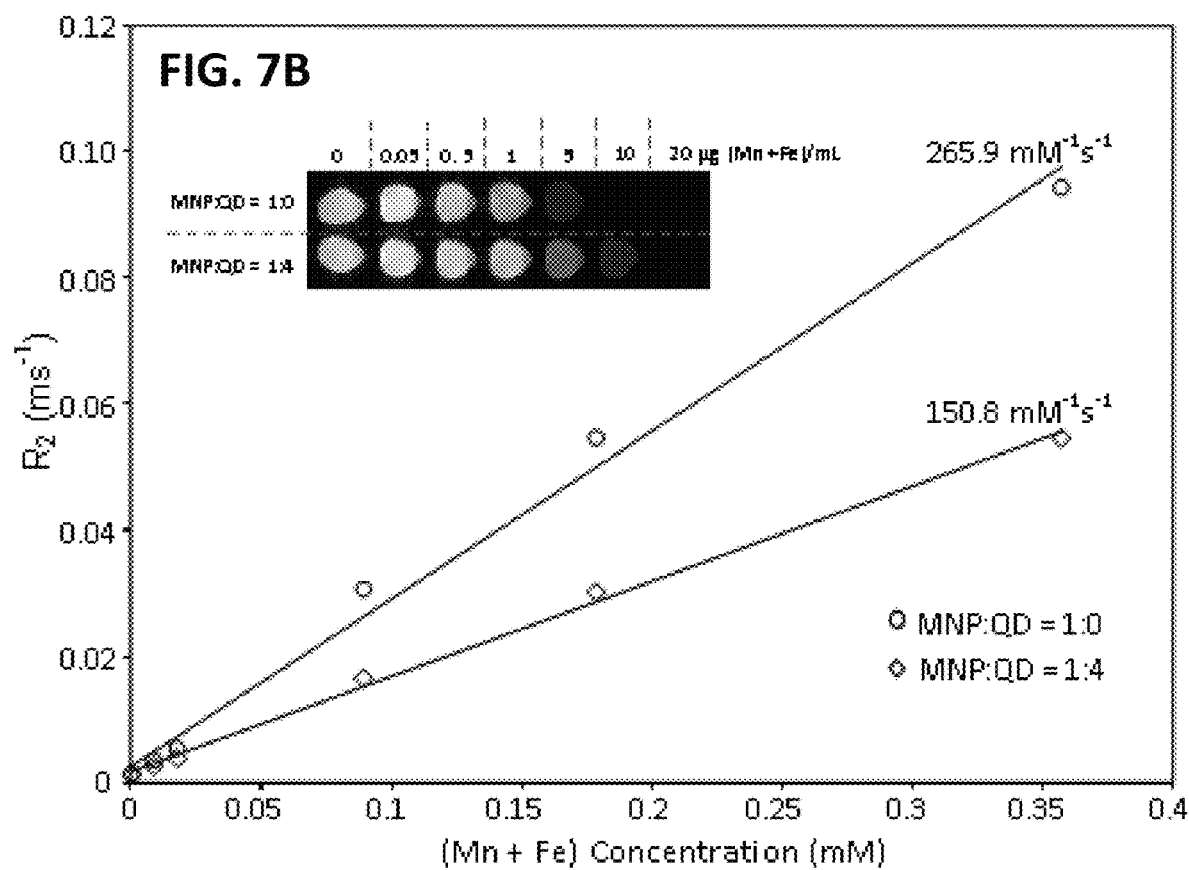

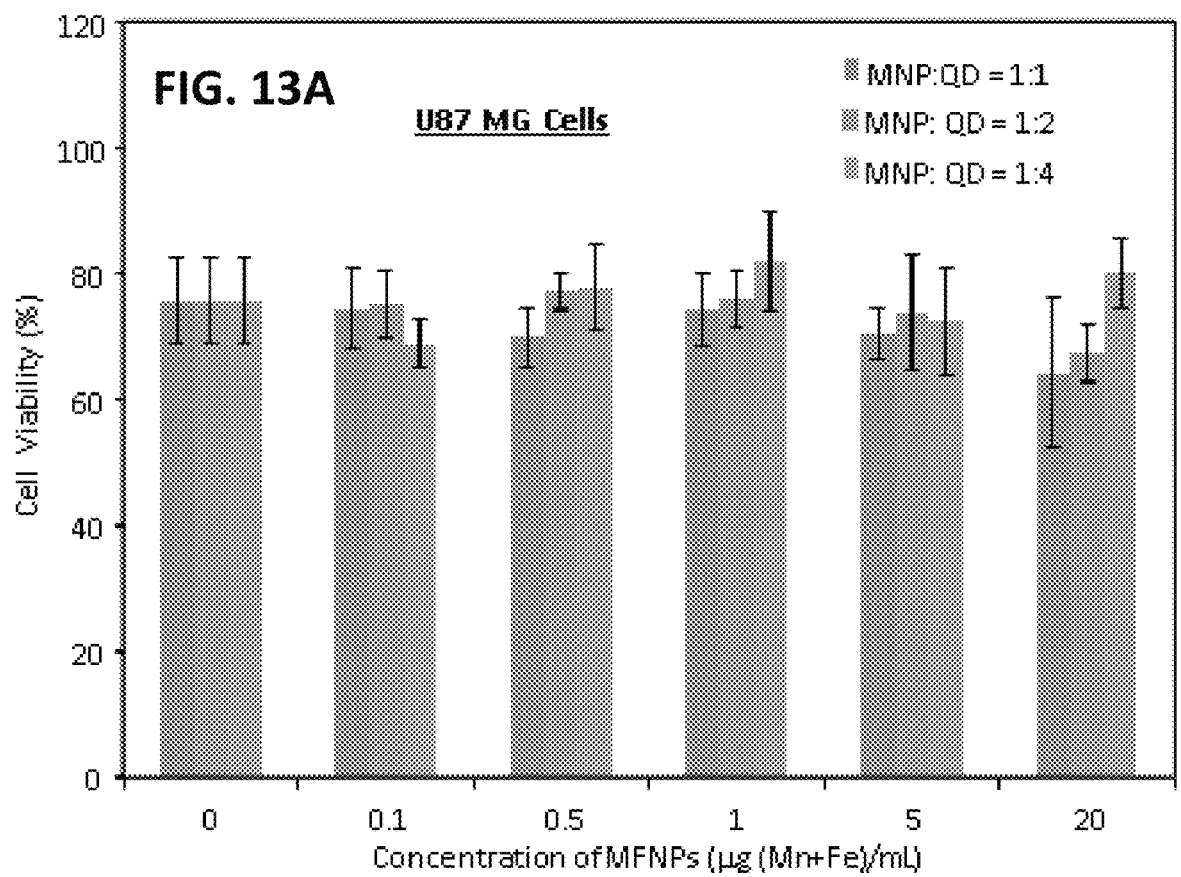
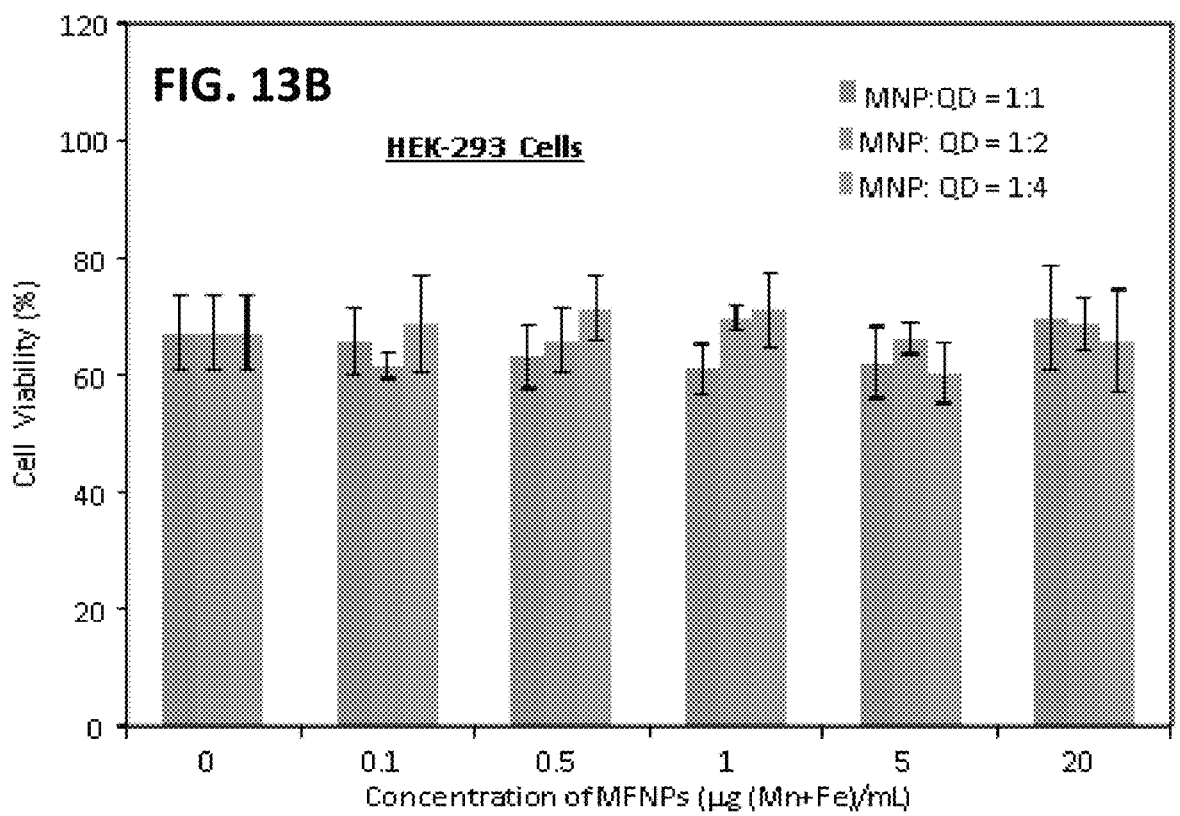

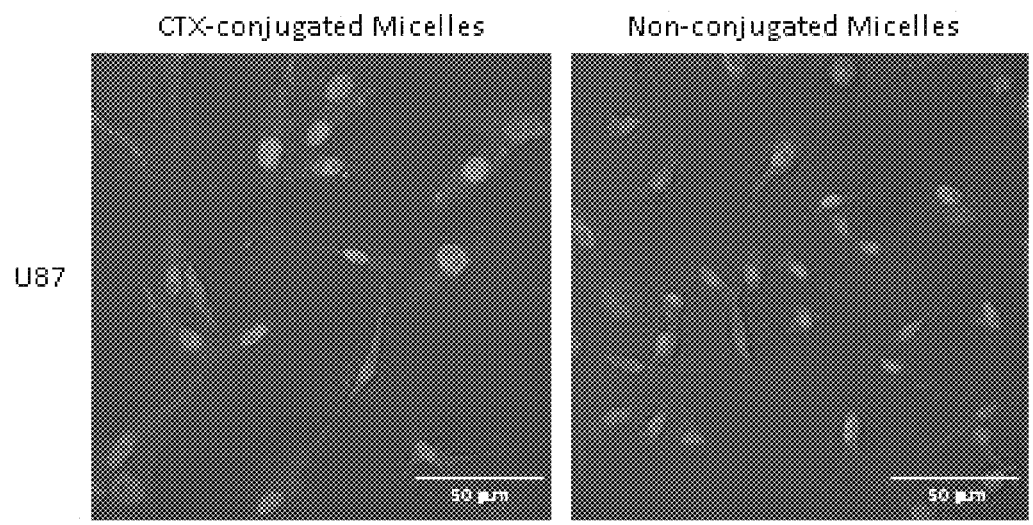
FIG. 31A  FIG. 31B
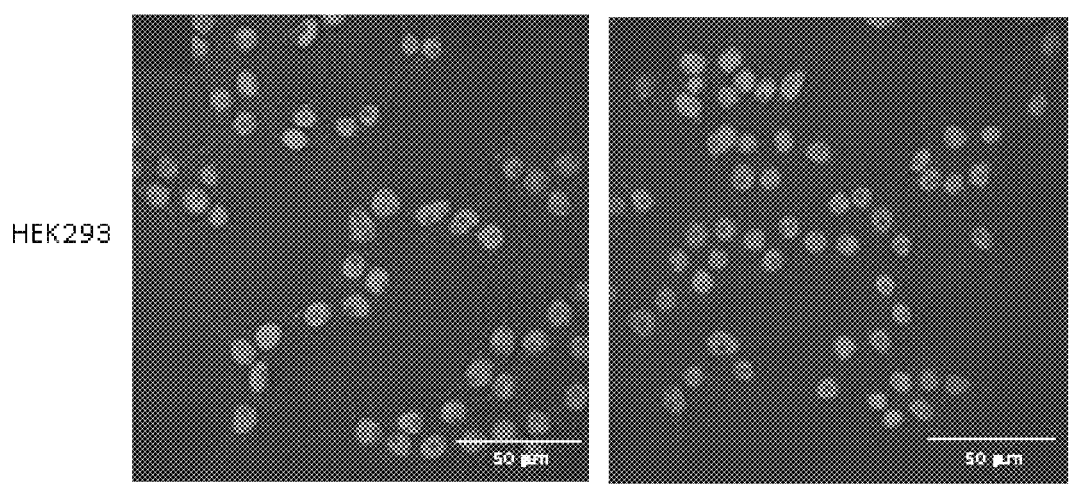
FIG. 31C  FIG. 31D

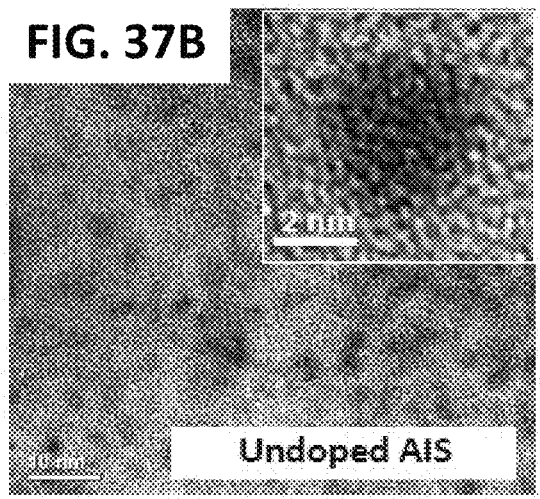
FIG. 37B Undoped AIS
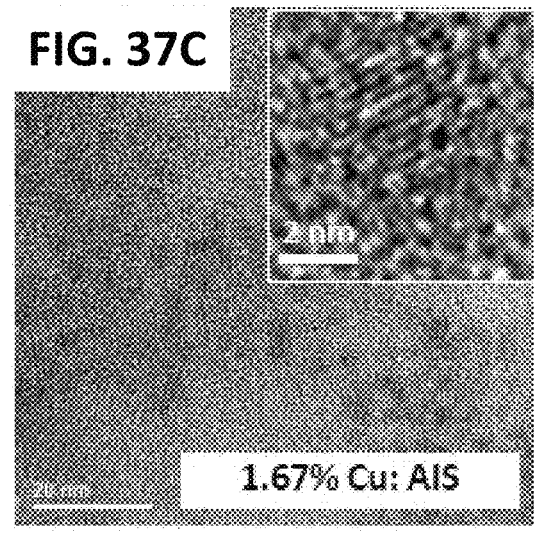
FIG. 37C 1.67% Cu: AIS
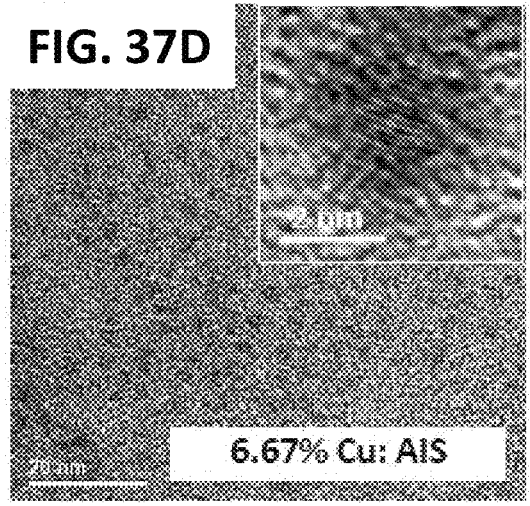
FIG. 37D 6.67% Cu: AIS

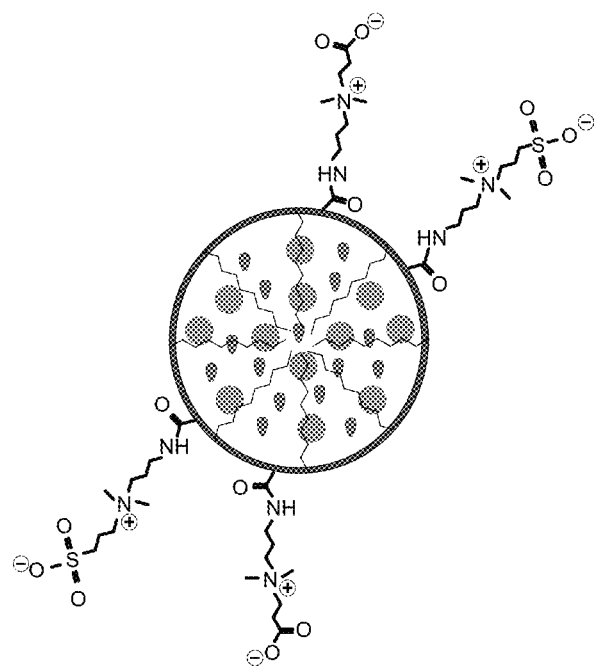
FIG. 51A
MR Image
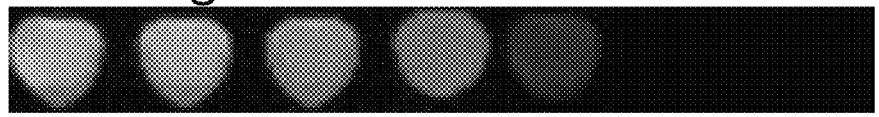
Optical Image
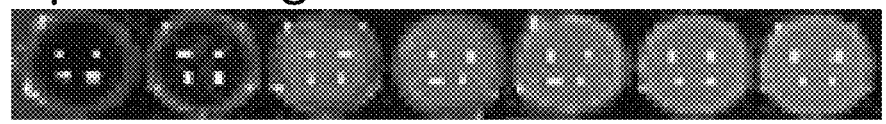
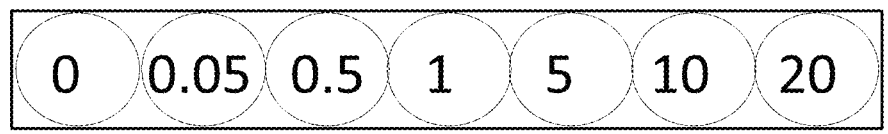
μgFe+Mn/mL
FIG. 51B

COMPOSITES AND COMPOSITIONS FOR THERAPEUTIC USE AND METHODS OF MAKING AND USING THE SAME

CROSS REFERENCE TO RELATED APPLICATION

This application claims the benefit of U.S. Provisional Application No. 62/569,291, filed on Oct. 6, 2017; and is a continuation-in-part of PCT Application No. PCT/US2016/042613, filed on Jul. 15, 2016, which claims the benefit of U.S. Provisional Application No. 62/203,325, filed Aug. 10, 2015, and U.S. Provisional Application No. 62/194,122, filed on Jul. 17, 2015; each of these applications is incorporated herein by reference in its entirety.

ACKNOWLEDGMENT OF GOVERNMENT SUPPORT

This invention was made with government support under Contract No. 1P20GM103650 awarded by the National Institutes of Health. The government has certain rights in the invention.

FIELD

The present disclosure concerns embodiments of composites and compositions comprising nanoparticle and/or quantum dot cores, and zwitterionic polymeric coatings. Also disclosed herein are embodiments of methods of making components used in the composites and compositions, as well as methods of making and using the composites and compositions.

BACKGROUND

Magnetofluorescent nanoparticles enabling simultaneous fluorescence labeling and magnetic field assisted separation, sorting, heating or imaging are gaining momentum for biomedical applications at the cellular, tissue or anatomical levels. For this reason, research approaches have been reported on the controlled synthesis of magnetofluorescent nanoparticles regarding their size, shape, composite and surface properties. To achieve colloidal stability and biocompatibility for various in vitro or in vivo applications, the hydrophilic shell of these type of magnetofluorescent nanoparticles are usually formed by anti-fouling poly(ethylene glycol) (PEG) chains. Zwitterion-coating approaches also have been developed for individual cadmium-based quantum dots or AuNPs but not for magnetofluorescent compounds. These approaches mainly involve the coupling of zwitterions with thiol ligands, such as dihydrolipoic acid. These coupled ligands are further exchanged with native hydrophobic ligands (trioctylphosphine oxide) to form thiol-bound zwitterionic quantum dots through the high binding affinity of thiols to Zn or Au atoms on quantum dot or AuNP surface.

Significant efforts are still needed to develop high quality quantum dots into broader biomedical applications especially for in vitro or in vivo sensing/imaging and drug delivery. There exists a need in the art for facile, scalable methods of making chalcopyrite quantum dots that are compatible for use in magnetofluorescent composites comprising nanoparticles. There also exists a need in the art for composites comprising zwitterionic coatings that can be used to produce composites capable for biomedical use and/or coupling to biomolecules.

SUMMARY

Disclosed herein are embodiments of composites comprising a core comprising one or more nanoparticles (such as magnetic nanoparticles), one or more quantum dots, or a combination thereof, and a zwitterionic polymeric coating comprising a zwitterionic polymer having any one of the formulas and/or structures disclosed herein. In some embodiments, the core comprises at least one magnetic nanoparticle and at least one quantum dot. Also disclosed herein are embodiments of compositions comprising a composite having a core comprising one or more magnetic nanoparticles, one or more quantum dots, or a combination thereof, a zwitterionic polymeric coating defining the core, and a biomolecule, a drug, or a combination thereof.

Also disclosed herein are embodiments of methods for making the composites, methods of making quantum dots, and methods of using the disclosed composites for visualizing uptake/binding in cells or tissues and/or treating subjects.

The foregoing and other objects, features, and advantages of the present disclosure will become more apparent from the following detailed description, which proceeds with reference to the accompanying figures.

BRIEF DESCRIPTION OF THE DRAWINGS

FIG. 1 is a combined photoluminescence spectrum of $AgInS_2$ (AIS) quantum dots and AIS/ZnS quantum dots where the inset shows a digital photograph of AIS quantum dots and AIS/ZnS quantum dots in organic solvents exposed under a UV laser beam.

FIG. 2 is a combined Fourier Transform Infrared (FT-IR) spectrum of a representative polymer precursor ("PMAO"), a representative polymer intermediate ("PMAO-DMAPA"), and a zwitterionic polymer ("PMAO-CB-SB").

FIG. 6A is a TEM image of a representative composite core having a nanoparticle to quantum dot ratio of 1:4; FIG. 6B is a zoomed image of a single composite core illustrating both spherical and irregular particle shapes representing nanoparticles and quantum dots; and FIG. 6C is an EDX spectrum.

FIGS. 7A and 7B are graphs illustrating results obtained from analysis of representative composites; FIG. 7A is a combined photoluminescence spectrum of hydrophobic quantum dots in organic solvent and water-soluble composites as disclosed herein; FIG. 7B is a graph of $R_2$ parameters of composites disclosed herein versus (Mn+Fe) concentration (the slope $r_2$ of each curve=$R_2$/[(Mn+Fe) concentration]), wherein the inset image is a representative magnetic resonance image of zwitterionic magnetofluorescent nanoparticles and zwitterionic magnetic nanoparticles.

FIG. 8A is a combined spectrum illustrating photoluminescence of hydrophobic quantum dots in THF and water-soluble composites; and FIG. 8B is a graph of $R_2$ parameters of composites versus (Mn+Fe) concentration (the slope $r_2$ of each curve=$R_2$/[(Mn+Fe) concentration]), wherein the inset image is a representative magnetic resonance image of composites fabricated with the nanoparticle to quantum dot mass ratios of 1:0, 1:1, 1:2, and 1:4.

FIGS. 13A and 13B are graphs illustrating cell viability cell treated with representative composites disclosed herein illustrating that the composites have no significant effects on cell cytotoxicity; FIG. 13A shows cell viability of U-87 MG cells treated with composites at different concentrations over 24 hours; and FIG. 13B shows cell viability of HEK-293 cells treated with zwitterionic magnetofluorescent nanoparticles at different concentrations over 24 hours.

FIG. 16A is a confocal image illustrating cellular uptake/internalization of cyclophosphamide ("CTX")-conjugated composites by U-87 cells; FIG. 16B is a confocal image illustrating cellular uptake/internalization of non-conjugated composites by U-87 cells; FIG. 16C is a confocal image illustrating cellular uptake/internalization of CTX-conjugated composites by HEK-293; FIG. 16D is a confocal image illustrating cellular uptake/internalization of non-conjugated composites by HEK-293 cells; and FIG. 16E is a bar graph of micelle photoluminescence intensity as a function of composite concentration illustrating the fluorescent intensity per unit area of cytoplasm for U-87 and HEK-293 cells incubated with CTX- and non-conjugated composites with different concentrations.

FIG. 19A is a TEM image of a representative quantum dot; FIG. 19B is a high resolution TEM image of a representative quantum dot; and FIG. 19C is an EDX spectrum of a representative quantum dot.

FIG. 24A illustrates quantum dots made using a Ag:In molar ratio of Ag:In=1:1; and FIG. 24B illustrates quantum dots made using a Ag:In molar ratio of Ag:In=1:2.

FIG. 28A is a TEM image of an individual quantum dot-micelle; FIG. 28B is a high resolution TEM image of an individual quantum dot-micelle; and FIG. 28C is an EDX spectrum of quantum dot-micelles.

FIG. 30A shows confocal images demonstrating the cellular uptake/internalization of CTX-conjugated quantum dot-micelles (100 times diluted from stock) by U-87 cells; FIG. 30B shows confocal images presenting the quenching effect of 1,10-phenanthroline on the uptake/internalization; and FIG. 30C shows quantitative data indicating the cellular uptake/internalization and the quenching effect under the different concentrations or dilutions of CTX-conjugated quantum dot-micelles (100-800 times dilutions).

FIGS. 31A-31E illustrate results obtained from analysis of representative quantum dots made using a disclosed thermal decomposition methods embodiment; FIG. 31A is an overlaid confocal image of U-87 cells after incubation with CTX-conjugated micelles comprising the quantum dots; FIG. 31B is an overlaid confocal image of U-87 cells after incubation with non-conjugated micelles comprising the quantum dots; FIG. 31C is an overlaid confocal image of HEK-293 cells after incubating with CTX-conjugated micelles comprising the quantum dots; FIG. 31D is an overlaid confocal image of HEK-293 cells after incubating with non-conjugated micelles comprising the quantum dots; and FIG. 31E illustrates the fluorescent intensity per unit area of cytoplasm for U-87 and HEK-293 cells incubated with CTX-conjugated and non-conjugated AIS/ZnS micelles.

FIG. 35A is a graph of photoluminescence intensity (a.u.) as a function of wavelength (nm) showing the effect of Cu-dopant concentrations on photoluminescence for surface-doped quantum dots, wherein the inset data plot shows that the evolution of photoluminescence spectra of non-doped AIS nanocrystals is not significant in the time course of growth; and FIG. 35B shows the absorption spectra of the copper-doped quantum dots with different Cu initial concentrations.

FIG. 36A shows the evolution of photoluminescence spectra of 3.33% Cu:AIS quantum dots in the time course of reaction using a surface doping approach, wherein the inset is the evolution of photoluminescence spectra of Cu:AIS quantum dots prepared through a homogenous reaction; FIG. 36B shows the temporal evolution of absorption spectra of 3.33% Cu:AIS quantum dots.

FIGS. 37A-37D show characterization data of representative Cu-doped quantum dots disclosed herein; FIG. 37A shows XRD patterns for AIS, 1.67% Cu:AIS and 6.67% Cu:AIS quantum dots; FIG. 37B shows TEM and high resolution TEM (insets) images of AIS quantum dots; FIG. 37C shows TEM and high resolution TEM (insets) images of 1.67% Cu:AIS quantum dots; and FIG. 37D shows TEM and high resolution TEM (insets) images of 6.67% Cu:AIS quantum dots.

FIG. 38A shows digital images of Cu:AIS and Cu:AIS/ZnS quantum dots suspended in organic solvents under a UV lamp;

FIG. 38B is a combined absorption spectrum of photoluminescence and absorption spectra of the core and core/shell quantum dots; FIG. 38C is shows the XRD patterns of 6.67% Cu:AIS and Cu:AIS/ZnS quantum dots; FIG. 38D shows TEM and high resolution TEM (inset) images of 6.67% Cu:AIS/ZnS quantum dots.

FIG. 45A shows a representative synthesis of Mn:AIZS-ZnS nanocrystal embodiments and the effect of Mn levels on photoluminescence tunability, wherein AIZS cores are formed first, Mn and Zn precursors are added to the surface, and the nanocrystal surfaces are further passivated by zinc (yellow, red, and green represent AIZS composites, Mn, and ZnS shell, respectively); FIG. 45B is a graph showing photoluminescence spectra of Mn:AIZS/ZnS nanocrystals as compared to an undoped AIZS/ZnS nanocrystal; and FIG. 45C is a graph showing absorption spectra of the nanocrystals, wherein some there is some spectrum overlap between photoluminescence spectra and absorption spectra indicating some photoluminescence emissions will be reabsorbed by the nanocrystals themselves.

FIGS. 47A-47D illustrate images of a Mn-doped nanocrystal embodiments, wherein FIG. 47A is a TEM image of a 0.075 mmol-Mn-doped AIZS/ZnS nanocrystal; FIG. 47B is a high resolution TEM image of a 0.075 mmol-Mn-doped AIZS/ZnS nanocrystal; FIG. 47C is a fast Fourier transform (FFT) pattern on the HRTEM image of a 0.075 mmol-Mn-doped AIZS/ZnS nanocrystal; and FIG. 47D is an EDX spectrum of the 0.075 mmol-Mn-doped AIZS/ZnS nanocrystal, which illustrates Ag, In, Mn, Zn and S elements (and wherein the unlabeled peaks above 10 KeV are gold elements from the gold-mesh grid used for TEM imaging).

FIG. 50A is an illustration of such a nanocrystal wherein Mn atoms are doped into the core of an AZIS nanocrystal and then the cores are shelled with ZnS layers; FIG. 50B is a graph showing fluorescence and absorption spectra of Mn-doped AZIS/ZnS nanocrystals; and FIG. 50C is a graph showing fluorescence decays of Mn-doped AZIS/ZnS nanocrystals under different Ag levels in the composites.

FIGS. 51A and 51B provide a schematic illustration of a representative composite wherein a zwitterionic polymer encapsulates both magnetic nanoparticles and I(II)-III-VI quantum dots through self-assembly (FIG. 51B) and representative magnetic resonance image and optical image of the composite at difference concentrations, wherein the concentration is marked by the Fe+Mn mass/mL (FIG. 51B).

FIG. 53A shows distribution after 3 hours of incubation; and FIG. 53B shows distribution after 24 hours of incubation.

DETAILED DESCRIPTION

I. Explanation of Terms

Figure 3:
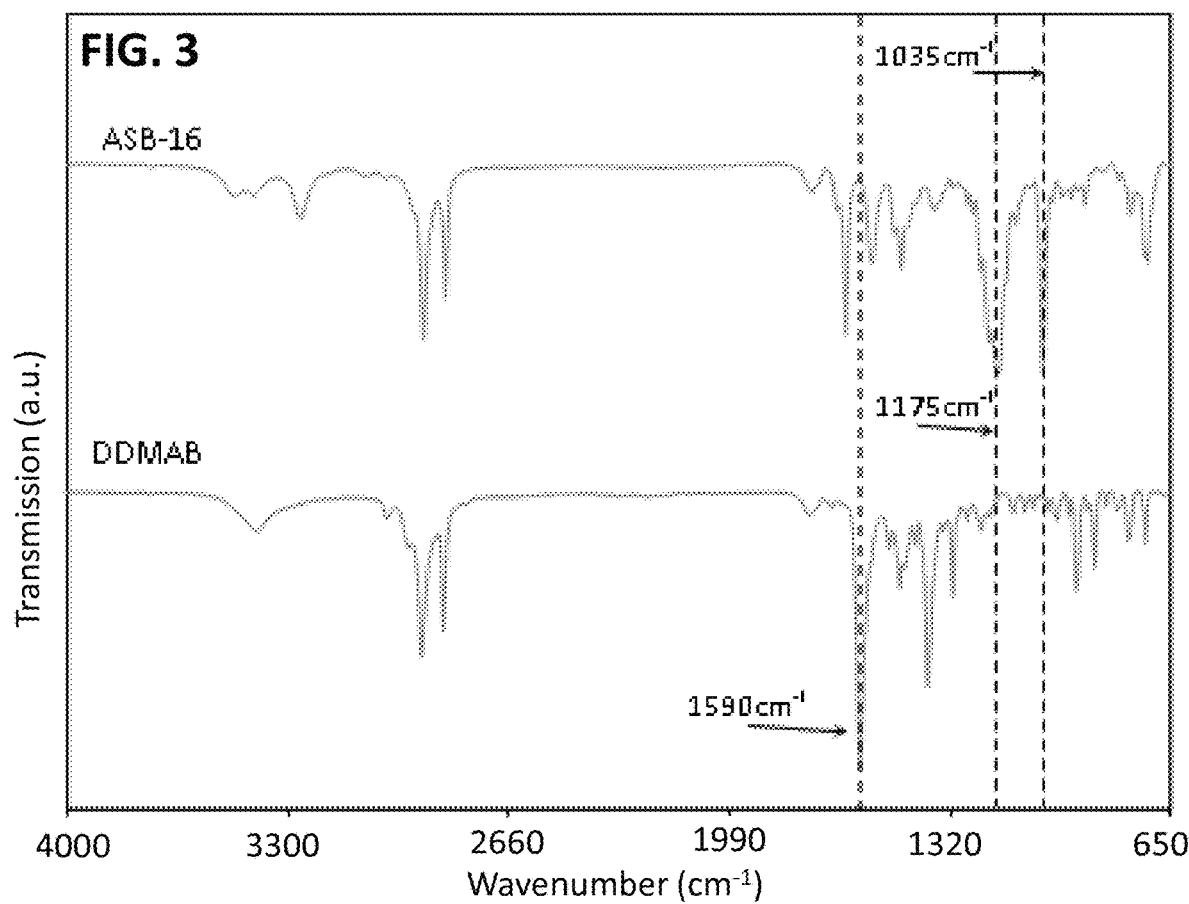
FIG. 3 is a combined FT-IR spectra of amidosulfobetaine-16 ("ASB-16") (with sulfobetaine) and N-dodecyl-N,N-(dimethylammonio)butyrate ("DDMAB") (with carboxybetaine).

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include an $R^a$ group that, though not part of the defined functional group, indicates how the functional group attaches to the compound to which it is bound.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Carboxylate: $R^aC(O)O^-$, wherein $R^a$ is the atom of the formulas disclosed herein to which the carboxyl group is attached.

Composite: A material comprising a core (which may comprise a nanoparticle, a quantum dot having a core or core/shell structure, or a combination or plurality thereof) and a zwitterionic polymeric coating comprising a zwitterionic polymer having a structure satisfying a formula disclosed herein, wherein the zwitterionic polymer coating encapsulates the core and wherein the composite exhibits properties that differ from each of its individual components.

Encapsulated: When a drug is described herein as "encapsulated," it is intended to mean that the drug is located within or attached to polymer side chains of the zwitterionic polymeric coatings described herein and/or within the core of the composite as defined by the zwitterionic polymeric coating.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Magnetic Nanoparticle: A class of nanoparticles that can be manipulated using magnetic field gradients.

Quantum Dot: A nanoscale particle that exhibits size-dependent electronic and optical properties due to quantum confinement. The quantum dots disclosed herein generally have at least one dimension less than 100 nanometers. The disclosed quantum dots may be colloidal quantum dots, i.e., quantum dots that may remain in suspension when dispersed in a liquid medium.

Sulfonate: A functional group having a formula $R^aSO_3^-$, wherein $R^a$ is the atom of the formulas disclosed herein to which the sulfonate is attached.

Zwitterionic Polymer/Zwitterionic Polymeric Coating: A polymer or polymeric coating disclosed herein that comprises both positive and negative electrical charges and that comprises a polymeric backbone having one or more zwitterionic side-chains extending therefrom. Typically, the polymers and polymeric coatings comprise at least one functional group that comprises a positive charge and at least one functional group that comprises a negative charge, and in most embodiments both such functional groups are located in the same polymer side chain (as distinguished from the polymer backbone).

II. Introduction

Micellar magnetofluorescent nanoparticles inherit the merits of magnetic nanoparticles (e.g., high saturation magnetization) and quantum dots (e.g., photostability and luminescence wavelength tunability), and also provide complementary merits from both magnetic resonance imaging and optical imaging (i.e., high spatial resolution and high sensitivity). Conventional methods used to produce magnetofluorescent nanoparticles require forming a hydrophilic shell using anti-fouling poly(ethylene glycol) (PEG) chains to achieve colloidal stability and biocompatibility for various in vitro or in vivo applications. Although PEG chains render such nanoparticles stable in physiological media, PEG groups are sensitive to solution pH and salinity and tend to cause such nanoparticles to aggregate in acidic or salt-rich microenvironments. This aggregation further degrades and can even change the diagnosis/therapy functionalities devised for original nanoparticles. This shortcoming of PEG-functionalized magnetofluorescent nanoparticles limits their applications in biological or biomedical applications, where harsh conditions are ubiquitous. For instance, many cellular organelles are maintained under acidic conditions and rich in salts. Moreover, it has been suggested in the art that PEG may induce in vivo production of anti-PEG immunoglobulin M (IgM) antibodies, which further affects in vivo applications of PEG coated magnetofluorescent nanoparticles.

Other conventional magnetofluorescent nanoparticles comprise cadmium-based quantum dots and/or gold nanoparticles with dihydrolipoic acid that can undergo ligand exchange with trioctylphosphine oxide ligands to form zwitterionic cadmium-based quantum dots or gold nanoparticles with singular ligands that are coupled to the cadmium core through a sulfur atom. Zwitterion coupled thiol ligands, however, have not been applicable to the preparation of magnetofluorescent nanoparticles integrating both magnetic nanoparticles and quantum dots. These thiol ligands are individually attached to the core and do not comprise a polymeric backbone.

The disclosed composites and methods of making the same address deficiencies associated with conventional composites and techniques. For example, scalable syntheses of high quality quantum dots are desired because a large amount of bright quantum dots can be produced in a single synthetic reaction to sustain biomedical research for reliable experimental observation or data collection and also save synthesis costs. The disclosed methods provide the ability to obtain such scalable syntheses. In addition, since quantum dots usually are synthesized in organic solvents and thus capped with hydrophobic ligands, facile surface/interface chemistries are required to render I—III-VI quantum dots water-dispersible and also to provide functional groups for subsequent bio-conjugation with biological moieties. The disclosed composites and compositions address this need. Additionally, the composites disclosed herein possess several merits including dual imaging properties, high (Mn+Fe) recovery, excellent stability in aqueous solutions with a wide pH/ionic-strength range and physiological media, minimal cytotoxicity, the ability to tune photoluminescence by surface doping, and cell targeting capabilities before and after bio-conjugation. Without being limited to a particular theory, it is currently believed that the high recovery of the composites is attributed to the efficient wrapping of the composite cores by the aliphatic tails of the zwitterionic polymeric coating, and that the colloidal stability, and minimal cytotoxicity for cell targeting results from the nature of the incorporated zwitterionic groups.

Additionally, the composites can be used for cell imaging and the photoluminescence tunability of the composites from the visible to near infrared (NIR) range contributes to their utility in in vivo diagnosis. The fluorescence imaging data obtained from the composites (e.g., NIR and magnetic resonance imaging) may also be used to provide complimentary information on tumor biology and thus enhance diagnosis accuracy.

III. Composites and Compositions

Disclosed herein are embodiments of composites and compositions thereof, wherein the composites comprise a core having a nanoparticle, quantum dot, or combination thereof and a polymeric coating that encapsulates the core. In exemplary embodiments, the composites comprise magnetofluorescent cores and a zwitterionic polymeric coating suitable for promoting biocompatibility and coupling to biomolecules. In particular disclosed embodiments, the magnetofluorescent core comprises at least one quantum dot and at least one magnetic nanoparticle.

The zwitterionic polymer coating, which comprises a polymeric backbone from which zwitterionic side chains extend, can be used to encapsulate the core of the composite, such as by forming a polymeric layer that surrounds a composition of magnetic nanoparticles, quantum dots, or a combination thereof. In particular disclosed embodiments, the zwitterionic polymeric coating comprises a polymer having a hydrophobic portion and a hydrophilic portion. The hydrophobic portion can be oriented so that it interacts with the core comprising the magnetic nanoparticles, quantum dots, or combination thereof to form a micellar core. The hydrophilic portion can be oriented so that it extends from the micellar core to promote solubility and/or biomolecular conjugation.

In some embodiments, the zwitterionic polymeric coating can comprise a polymer having a pH-responsive group, which can comprise a combination of a functional group positioned on the polymeric chain of the polymer, which comprises a tertiary amine, and a functional group positioned on the polymeric chain of the polymer, which comprises a carboxyl group. The combination of these two functional groups can provide a weak zwitterionic moiety. In such a weak zwitterion, the free proton from the carboxyl group can be transferred to the tertiary amine without affecting the neutral charge of the whole pair. In some embodiments, the $pK_a$ of the carboxyl group of the weak zwitterionic moiety is around 5.0-6.0, and can be protonated in acidic endosomes and thus lead to osmotic swelling and endosome rupture benefitting the ensodomal escape of micelles. In yet additional embodiments, the zwitterionic polymer can comprise carboxybetaine groups that can also absorb protons in acidic conditions for endosomal escape. In some embodiments, the molar ratio of functional groups present on the zwitterionic polymeric coating (e.g., carboxybetaine groups, sulfobetaine groups, pH responsive groups, and thiol-containing groups) can be modified to provide a desired reactivity of the micelle formed with the polymeric coating and the core.

In particular disclosed embodiments, the zwitterionic polymeric coating can comprise a polymer having a structure meeting Formula I below.

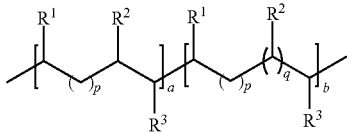

Formula I

With reference to Formula I, each $R^1$ can provide the hydrophobic portion of the polymer and independently can be selected from hydrogen or aliphatic; each $R^2$ independently can be —C(O)Z, wherein Z can be selected from hydroxyl, ether, amine, thiol, or thioether; each $R^3$ can (alone or in combination with $R^2$) provide the hydrophilic portion of the polymer and independently can be selected from amide-aliphatic-amine (e.g., —CO(NR$^b$)C1-C10alkylN(R$^b$)$_2$, wherein each $R^b$ independently can be selected from hydrogen, aliphatic, heteroaliphatic, aryl, or heteroaryl), amide-aliphatic-amine-aliphatic-carboxylate (e.g., —CO(NR$^b$)C1-C10alkyl [N(R$^b$)$_2$]$^+$C1-C10alkyl-CO$_2^-$, wherein each $R^b$ independently can be selected from hydrogen, aliphatic, heteroaliphatic, aryl, or heteroaryl), amide-aliphatic-amine-aliphatic-sulfonate (e.g., —CO(NR$^b$)C1-C10alkyl [N(R$^b$)$_2$]$^+$C1-C10alkyl-SO$_3^-$, wherein each $R^b$ independently can be selected from hydrogen, aliphatic, heteroaliphatic, aryl, or heteroaryl), or amide-aliphatic-thiol (e.g., —CO(NR$^b$)C1-C10alkylSH, wherein $R^b$ can be selected from hydrogen, aliphatic, heteroaliphatic, aryl, or heteroaryl); p can be an integer selected from zero to 5; q can be an integer selected from zero or 1; and each of a and b independently can be an integer selected from 1 to 200.

In some embodiments, the zwitterionic polymeric coating can comprise a polymer having a structure satisfying any one of Formulas II-VI below.

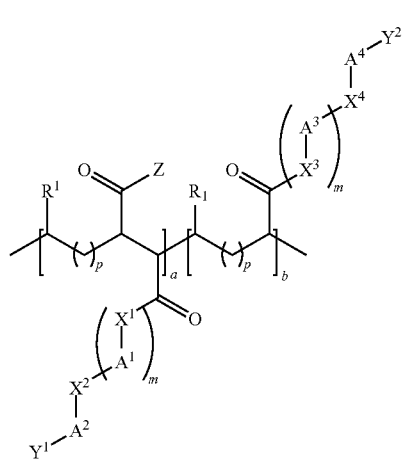

Formula II

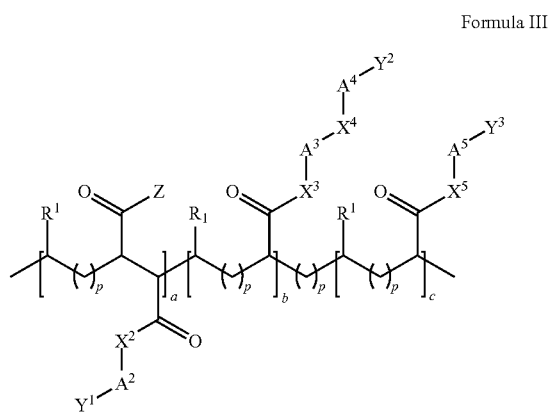

Formula III

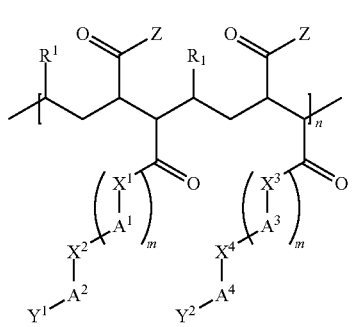

Formula IV

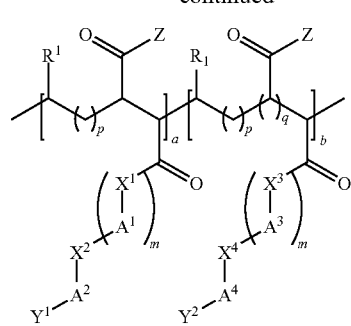

Formula V

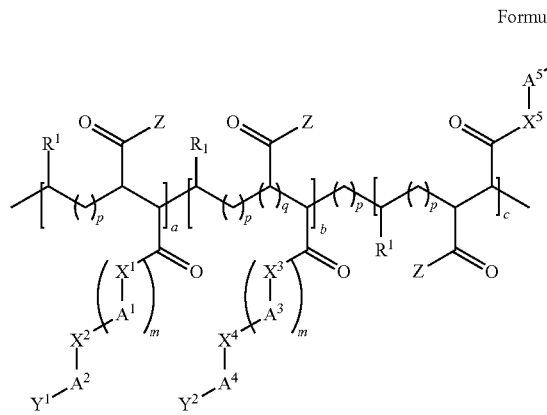

Formula VI

With reference to Formulas II-VI, each $R^1$ independently can be selected from hydrogen or aliphatic; each $X^1$, $X^2$, $X^3$, $X^4$, and $X^5$ independently can be selected from $NR^b$, $N(R^b)_2{}^+$, oxygen, or sulfur, wherein each $R^b$ independently can be selected from hydrogen, aliphatic, heteroaliphatic, aryl, or heteroaryl; each $A^1$, $A^2$, $A^3$, $A^4$, and $A^5$ independently can be selected from aliphatic or heteroaliphatic; each $Y^1$, $Y^2$, and $Y^3$ independently can be selected from amine, thiol, carboxylate or sulfonate; each Z independently can be selected from hydroxyl, ether, amine, thiol, or thioether; n can be an integer selected from 1 to 200; each m can be an integer selected from 0 to 3, such as 0, 1, 2, or 3; each p independently can be an integer selected from zero to 5; a can be an integer selected from 1 to 200, such as 1 to 100 or 5 to 50; and b and c independently can be an integer selected from 0 to 200, such as 1 to 100 or 5 to 50.

In particular disclosed embodiments, each $R^1$ independently can be selected from hydrogen, alkyl, alkenyl, or alkynyl; each $X^1$, $X^2$, $X^3$, $X^4$, and $X^5$ independently can be selected from $NR^b$, $N(R^b)_2{}^+$, oxygen, or sulfur, wherein each $R^b$ independently can be selected from hydrogen, alkyl, alkenyl, alkynyl, heteroalkyl, heteroalkenyl, heteroalkynyl, phenyl, naphthyl, or pyridinyl; each $A^1$, $A^2$, $A^3$, $A^4$, and $A^5$ independently can be selected from alkyl, alkenyl, alkynyl, heteroalkyl, heteroalkenyl, or heteroalkynyl; each $Y^1$ and $Y^2$ independently can be selected from carboxylate or sulfonate; $Y^3$ can be SH; each Z independently can be selected from hydroxyl, thiol, or $NH_2$; and m is 1.

In yet additional embodiments, each $R^1$ independently can be selected from hydrogen or C1-C20 alkyl (such as C1-C16 alkyl, or C1-C10 alkyl); each $X^1$, $X^2$, $X^3$, $X^4$, and $X^5$ independently can be selected from NH or $NMe_2{}^+$; each $A^1$, $A^2$, $A^3$, $A^4$, and $A^5$ independently can be selected from C1-C20 alkyl (such as C1-C10 alkyl or C1-C5 alkyl, or C1-C3 alkyl); each $Y^1$ and $Y^2$ independently can be selected from carboxylate or sulfonate; $Y^3$ can be SH; and each Z independently can be hydroxyl. In exemplary embodiments, the zwitterionic polymer coating can have any one of the structures below.

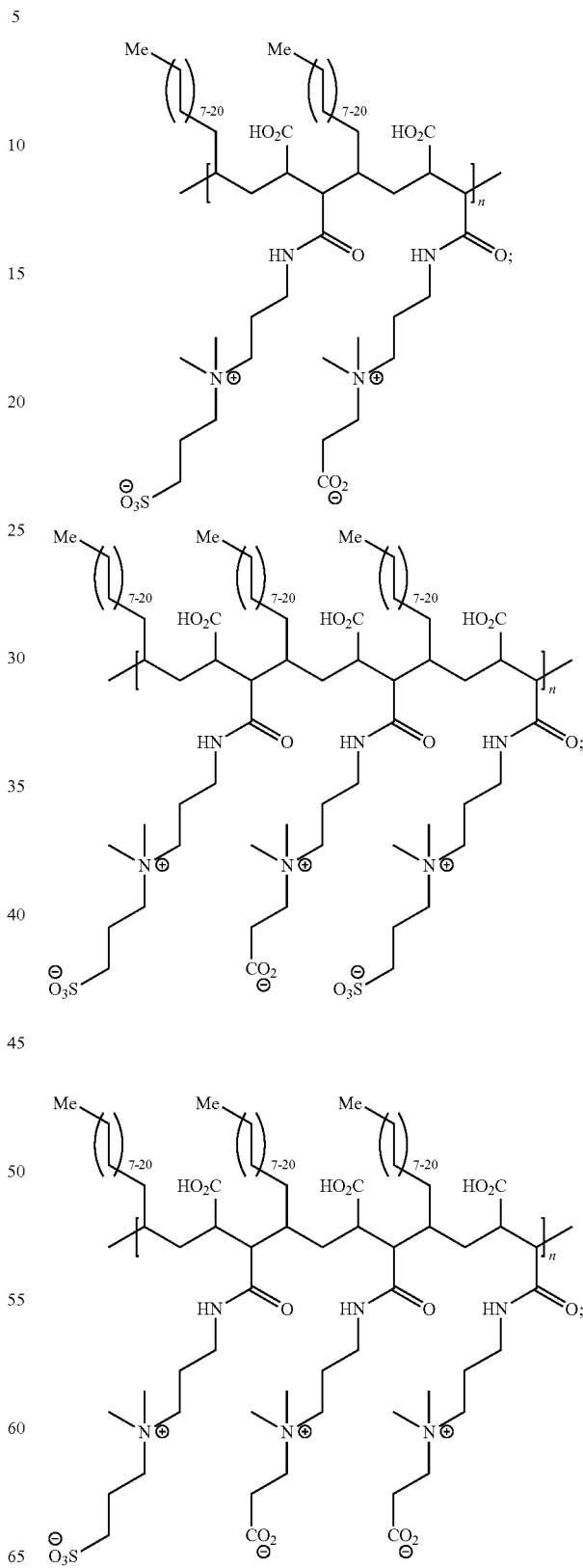

-continued

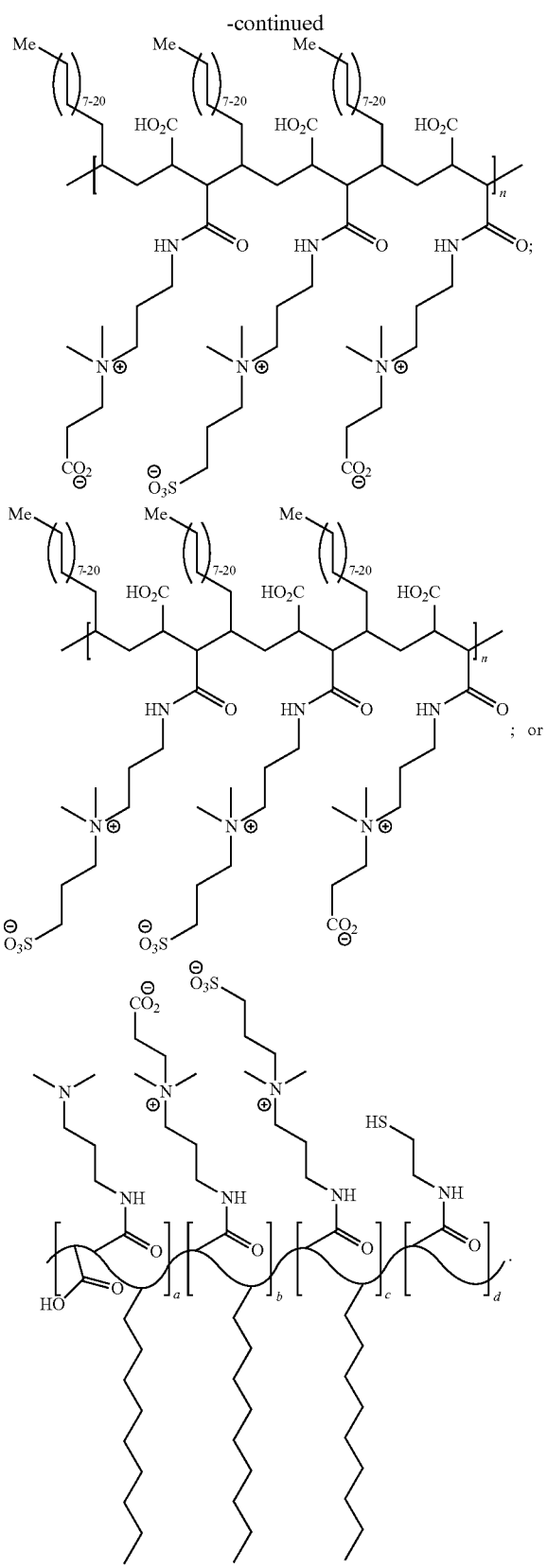

The composites disclosed herein can comprise a core that includes a nanoparticle, a quantum dot, or a combination thereof. In particular embodiments, the core comprises a magnetic nanoparticle, a quantum dot, or a combination thereof. In yet additional embodiments, the core comprises a magnetic nanoparticle and a quantum dot. In such embodiments, the core is considered magnetofluorescent. In particular disclosed embodiments, the composite comprises $MnFe_2O_4$ magnetic nanoparticles, $CuInS_2$ quantum dots, $AgInS_2$ quantum dots, or any combination thereof.

In some embodiments, the nanoparticles are magnetic and can be nanoparticles comprising a metal selected from Mn, Fe, Ni, Co, or combinations thereof. In particular disclosed embodiments, the magnetic nanoparticle comprises a metal and/or a metal oxide, such as an iron oxide, a nickel oxide, a cobalt oxide, a manganese oxide, or a combination thereof. Exemplary magnetic nanoparticles include, but are not limited to $MnFe_2O_4$, $Fe_3O_4$, $CoFe_2O_4$, FePt, or a combination thereof. In some embodiments, the nanoparticles, quantum dots, or both can have core sizes of greater than 1 nm to 10 nm, such as 1 nm to 8 nm, or 1 nm to 5 nm.

Suitable quantum dots that can be used in the composites disclosed herein include, but are not limited to, tertiary or ternary quantum dots, such as $AgInS_2$, $Ag(In,Ga)Se_2$, $Ag(Zn,Sn)Se_2$, $Ag(Zn,Sn)S_2$, $AgIn(Se,S)_2$, $AgZn(Se,S)_2$, $AgSn(Se,S)_2$, and $Ag(Zn,Sn)(Se,S)_2$ZnSSe, ZnSeTe, ZnSTe, ScSTe, HgSSe, HgSeTe, HgSTe, ZnHgS, ZnHgSe, ZnHgTe, ZnHgSSe, ZnHgSeTe, InGaAs, GaAlAs, InGaN, $CuInS_2$, $Cu(In,Ga)Se_2$, $Cu(Zn,Sn)Se_2$, $Cu(Zn,Sn)S_2$, $CuIn(Se,S)_2$, $CuZn(Se,S)_2$, $CuSn(Se,S)_2$, and $Cu(Zn,Sn)(Se,S)_2$. In some embodiments, the quantum dots used in the composites are quantum dots. Exemplary quantum dots include, but are not limited to, $CuInS_2$ quantum dots and $AgInS_2$ quantum dots. The quantum dot can be a core quantum dot or a core/shell quantum dot. In core/shell embodiments, the quantum dot can be selected from any quantum dot described herein and can further comprise a shell made of a binary material selected from, but not limited to, CdS, CdSe, CdTe, GaAs, InAs, InN, InP, InSb, PbS, PbSe, PbTe, ZnS, ZnSe, or ZnTe; an ion species, such as a halide (e.g., bromide, chloride, fluoride, or iodide); or a combination thereof. In exemplary embodiments, ZnS or chloride is selected as the shell component. Exemplary embodiments of core/shell quantum dots include, but are not limited to, $CuInS_2$/ZnS quantum dots and $AgInS_2$/ZnS quantum dots. Core and core/shell quantum dots can be used in combination with nanoparticles, particularly nanoparticles, to form an overall core used in the composites disclosed herein.

The core of the composite also can be doped with one or more metals. In particular disclosed embodiments, quantum dots (core and/or core/shell quantum dots) and/or nanoparticles (e.g., magnetic nanoparticles) can be doped with a metal selected from Cu, Ag, Au, Mn, Zn, or combinations thereof. Doping the cores of the disclosed composites provides the ability to tune the optical properties and material characteristics of the cores and also can prolong the photoluminescence lifetime of the composites disclosed herein. Photoluminescence tuning of the composites can be used avoid cross-talk with other existing dyes in bioimaging/sensing, and also provides design flexibility for optoelectronic devices, such as light-emitting diodes (LEDs) with different color emissions. Like other composites disclosed herein, the doped cores can be encapsulated with the zwitterionic polymeric coatings disclosed herein to form composites. The doped composites can be used as photoluminescent probes in cellular imaging and tissue imaging.

Also disclosed herein are compositions comprising the composites described above and one or more biomolecules. In some embodiments, the biomolecules of the composition can be the same. In yet other embodiments, multiple different biomolecules can be used. Biomolecules can be selected from targeting ligands, antibodies, nucleic acids, therapeutic molecules, or a peptide having biofunctionality, or combinations thereof. In exemplary embodiments, the biomolecules can be selected from chlorotoxin, avidin, biotin, folic acid, arginylglycylaspartic acid, or combinations thereof.

The biomolecules can be chemically conjugated to the composites, such as electrostatically and/or covalently. In some embodiments, biomolecules can be covalently bound to functional groups on the composite, such as carboxylate groups of the zwitterionic polymer coating. In some embodiments, the composites can comprise a mixture of carboxylate and sulfonate functional groups to facilitate conjugation to biomolecules through the carboxylate groups and also to maintain the zwitterionic nature of the polymer using sulfonate groups, which do not react with the biomolecules. In some embodiments, the disclosed compositions can be used to determine and demonstrate the biomedical uses of the composites and compositions, such as by performing cellular/tissue studies to investigate cytotoxicity of the composites and/or compositions and specific cellular binding/uptake of conjugated composites by cells, such as tumor cells.

Figure 33:
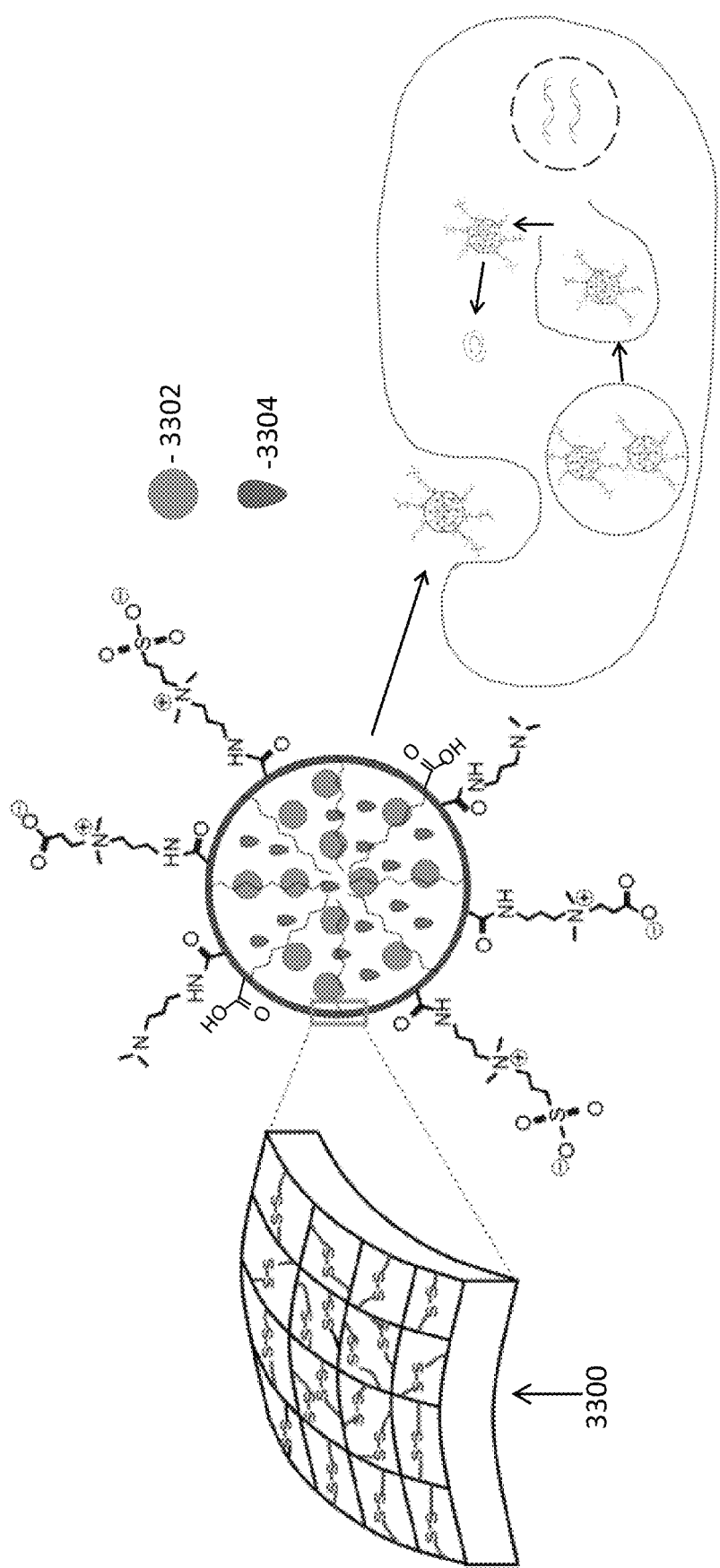
FIG. 33 is a schematic diagram illustrating a representative composite and use of the composite to administer drug molecules to a cell.

In some embodiments, drugs, such as chemotherapy drugs (e.g., doxorubicin, daunorubicin, epirubicin, idarubicin, or the like) can be loaded into the cores of micelles for therapeutic drug delivery applications. Once exposed to physiological conditions (e.g., circulation environments), drugs encapsulated in micelles usually are released within the first several hours, after which their concentrations reach a saturation plateau. The burst release should be minimal before micelles are internalized into target cells, but efficient after they are in target cells. To prevent premature drug leakage, thiol groups can be incorporated into the zwitterionic polymer to form disulfide cross-linkages in oxidative conditions and thereby form a cross-linked layer of the zwitterionic polymeric coating. FIG. 33 illustrates an exemplary embodiment wherein a cross-linked layer 3300 is formed by thiol groups of a polymeric coating backbone. The presence to thiol groups can help different polymer backbones to cross link with each other and form a shell on the surface. This shell is stable under physiological conditions minimizing drug leakage, but sensitive to and degradable in intracellular reductive-microenvironments. As illustrated in FIG. 33, the cross-linked layer can encapsulate quantum dots 3302 and drug molecules 3304. The devised shell is designed to help micelles to achieve more drug release inside cells.

The composites disclosed herein can be characterized using a variety of techniques. In some embodiments, Fourier transform infrared (FT-IR) spectroscopy and nuclear magnetic resonance (NMR) spectroscopy can be used to characterize the composites. In yet additional embodiments, the composites can be characterized based on their particle composition and size, iron content recovery rates, optical properties, colloidal stability, and magnetic relaxivity in harsh conditions using transmission electron microscopy (TEM), energy-dispersive X-ray (EDX) spectroscopy, dynamic light scattering (DLS), UV-Vis spectroscopy, fluorescence spectroscopy, magnetic resonance spectroscopy, and combinations thereof.

IV. Methods of Making Composite Components, Composites, and Compositions

Described herein are embodiments of methods for making the composite components described above, the composites themselves, and compositions comprising the composites. Methods for making composite components, such as the zwitterionic polymer coating and the quantum dots that can be used in the magnetofluorescent core also are described below.

In some embodiments of making the zwitterionic polymers described herein, the methods comprise converting a polymer precursor to a polymeric intermediate, which can then be reacted with suitable reagents that provide the zwitterionic portion of the polymer.

Scheme 1

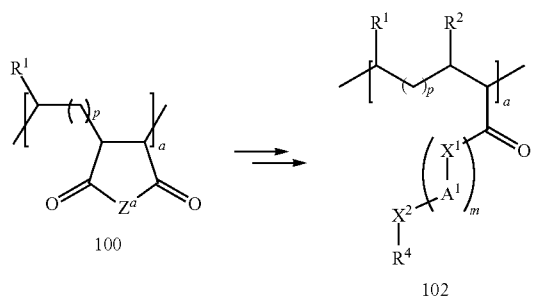

As illustrated in Scheme 1, polymeric precursor 100 can be converted to polymeric intermediate 102 by addition of an appropriate nucleophile to polymeric precursor 100, which ring-opens to provide polymeric intermediate 102. With respect to Scheme 1, each $R^1$, $R^2$, $X^2$, $A^1$, m a, and p can be as recited above; $Z^a$ can be selected from oxygen or $NR^b$; and each $R^4$ independently can be selected from hydrogen or aliphatic. In particular embodiments, a method as illustrated in Scheme 2 can be used to produce polymeric intermediate 202 from polymeric precursor 200. In some embodiments, the zwitterionic polymer coating can comprise functional groups suitable for forming disulfide cross-linkages within the polymeric coating to thereby form a cross-linked layer of the polymer (FIG. 33). In such embodiments, the disulfide-containing polymers can be made by reacting a polymeric precursor with a disulfide-containing reagent, such as 2-(2-pyridyldithio)ethylamine. The disulfide bond of the disulfide-containing reagent can be reduced to a thiol using excess dithiothreitol (DTT). The crosslinking between thiol groups of the polymeric coating can be conducted under aqueous oxidative conditions during the removal of DTT from micelles by dialysis against PBS buffer.

Scheme 2

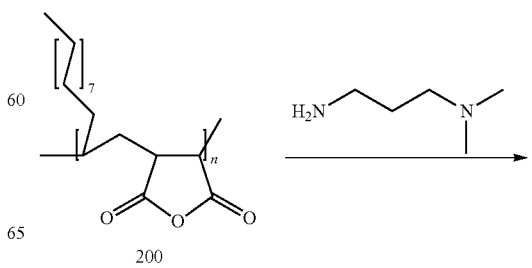

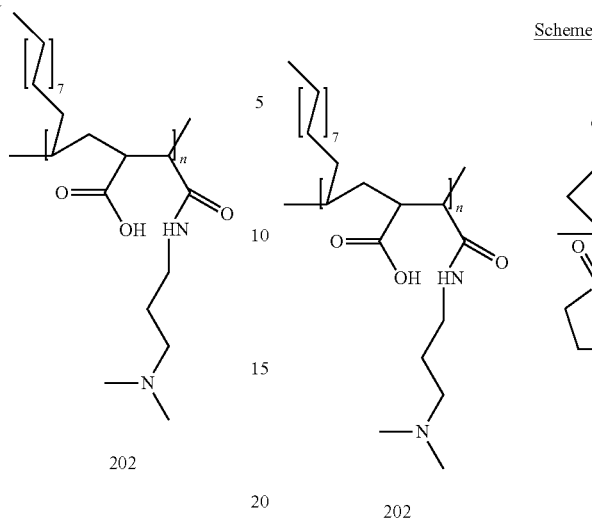

The polymeric intermediate can then be converted to a zwitterionic polymer 300 by reacting polymeric intermediate 102 with one or more different electrophiles capable of providing a carboxylate moiety, a sulfonate moiety, or a combination thereof, as illustrated in Scheme 3 below. In some embodiments, a cyclic lactone and/or a cyclic sulfone can be used as the electrophile component.

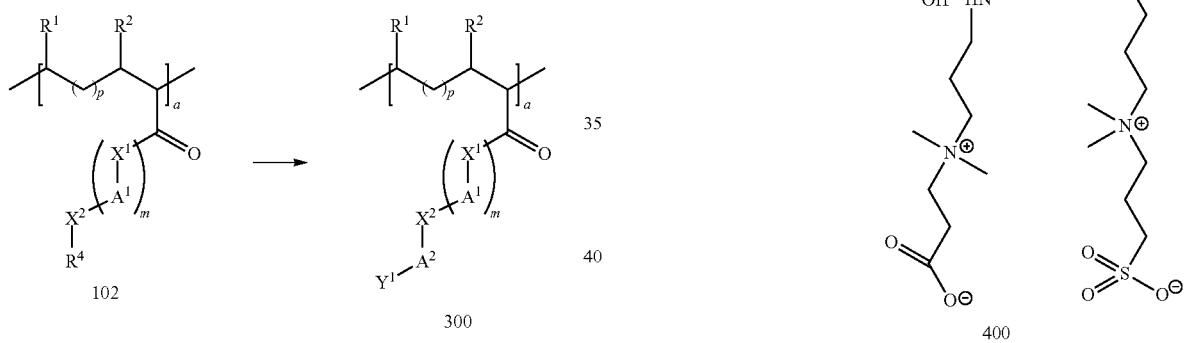

An exemplary method of producing a zwitterionic polymer is illustrated below in Scheme 4. As illustrated in Scheme 4, polymeric intermediate 202 is reacted with β-propiolactone and 1,3-propanesultone in one step to provide the carboxylate- and sulfonate-containing zwitterionic polymer 400. This method can be used to produce such compounds in one step without having to utilize multiple steps to attach both the carboxylate and the sulfonate moieties. The resulting zwitterionic polymer possesses carboxybetaine groups, sulfobetaine groups, and hydrophobic groups on their backbones. Compared to sulfobetaine, carboxybetaine groups are not only zwitterions but also supply carboxyl heads for bio-conjugation with conventional EDC/NHS cross-linkers. The sulfobetaine groups are insensitive to regular bio-crosslinking reactions and thus keep the zwitterionic property of the amphiphiles during conjugation. Although simple carboxyl groups are presented on the polymer backbone, carboxybetaine in the polymeric coating can further increase the biomolecule loading capability of composites through bio-crosslinking. Moreover, carboxybetaine branches can be provided that are similar to or substantially similar to the length of the sulfobetaine branches and therefore are easy to access for bio-conjugation.

In yet additional embodiments, the zwitterionic polymeric coating can be made by first making a functionalized zwitterionic intermediate 500 and then reacting the functionalized zwitterionic intermediate 500 with a polymeric precursor 100, such as is illustrated in Scheme 5.

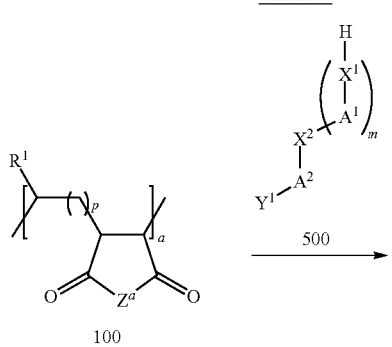

-continued

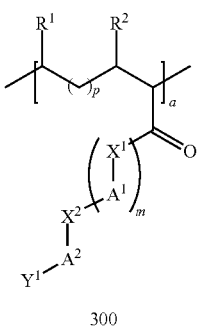

300

With respect to Scheme 5, each of $R^1$, $R^2$, $R^4$, $X^1$, $X^2$, $A^1$, $Z^a$, m, a, and p can be as recited above. A representative method of making the zwitterionic polymer in this fashion is illustrated in Scheme 6 below.

Scheme 6

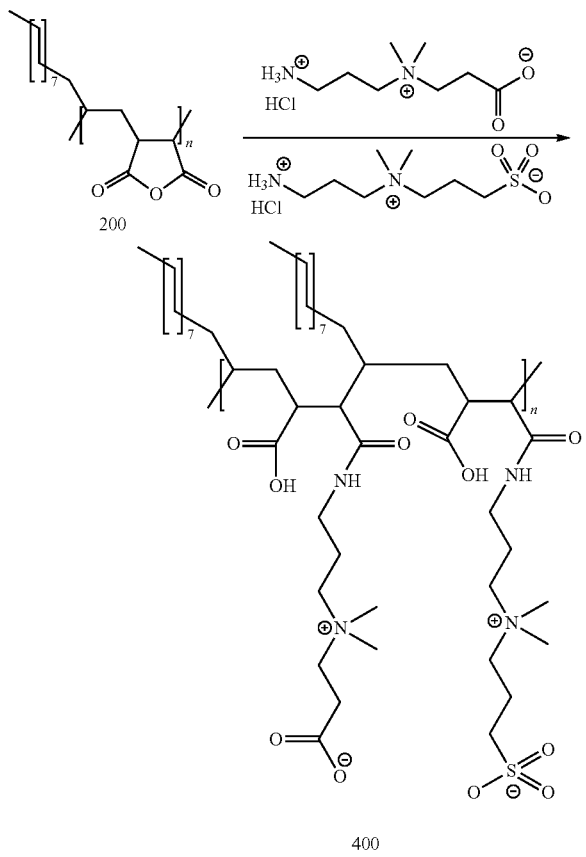

Figure 32:
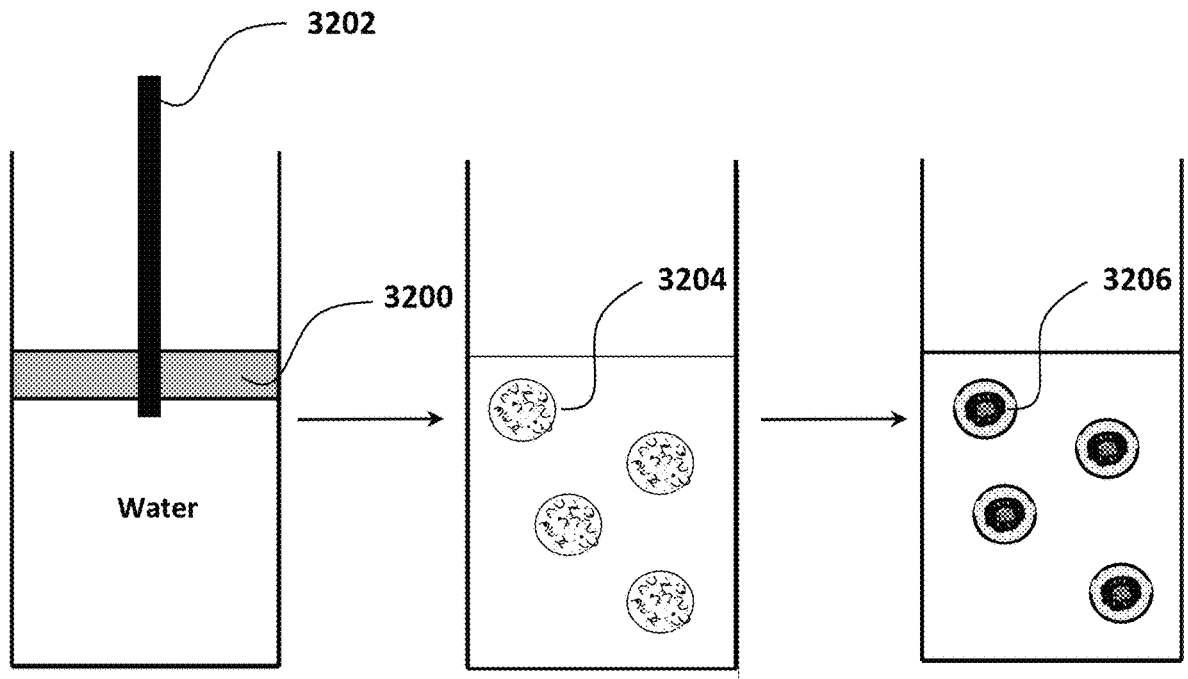
FIG. 32 provides an exemplary schematic of a representative method of making micelles comprising the polymeric coatings disclosed herein.

To produce the composites, the zwitterionic polymeric coating together with hydrophobic magnetic nanoparticles, quantum dots, or a combination thereof can be dissolved in organic solvents and then dispersed into water under sonication. FIG. 32 provides an exemplary schematic of a representative method of making micelles comprising the polymeric coatings disclosed herein. As illustrated in FIG. 32, an organic solution 3200 comprising a polymer as disclosed herein, one or more quantum dots, nanoparticles, a drug, or any combination thereof is mixed with water and undergoes sonication using a sonicator 3202. After sonication the micelles begin to form (3204) and vacuum removal of the organic solvents provides the formed micelles (3206). After dispersion, organic solvents can be removed by vacuum under rotary evaporation. In the dispersion and vacuum, hydrophobic alkyl tails in the amphiphiles interact with hydrophobic nanoparticles, quantum dots, or both to form the stable micellar cores, and carboxylate and sulfonate groups are exposed to water.

In some embodiments, the quantum dots used in the composites disclosed herein can be made using a thermal decomposition method. The thermal decomposition method can be easily scaled up to a commercial scale for quantum dot production as compared to conventional hot-injection methods. In some embodiments, a quantum dot precursor is used in the thermal decomposition method. In comparison to hot-injection methods, the present method does not require multiple washing and dryings steps or the use of toxic sodium diethyldithiocarbamate to produce the quantum dot precursor. Instead, the present methods use metal precursors and non-toxic ligands to produce the quantum dots in situ. No complex precursors, external sulfur sources, or other solvents are needed. Also, all chemicals used in the methods are commercially available.

The thermal decomposition methods described herein can comprise combining a Group 11 metal precursor, a Group 13 metal precursor, and a ligand in a thiol-containing solvent. In some embodiments, the Group 11 metal precursor is selected from a silver precursor or a copper precursor. In some embodiments, the Group 13 metal precursor is an indium precursor. In particular disclosed embodiments, silver acetate or copper acetate can be used as the Group 11 metal precursor and indium acetate can be used as the Group 13 metal precursor. Suitable ligands include, but are not limited to fatty acids, such as oleic acid, palmitoleic acid, linoleic acid, and the like. In some embodiments, the thiol-containing solvent is dodecanethiol, octadecanethiol, octanethiol, decanethiol, or combinations thereof.

The Group 11 metal precursor, the Group 13 metal precursor, and the ligand are combined in the thiol-containing solvent and are heated at a temperature suitable to facilitate thermal decomposition of the precursors to thereby form the desired quantum dots, such as quantum dots. In some embodiments, the temperature ranges from 150° C. to 200° C., such as 160° C. to 190° C., or 170° C. to 180° C. In particular disclosed embodiments, the reaction mixture of the Group 11 metal precursor, the Group 13 metal precursor, the ligand, and the solvent is heated at 170° C.

In some embodiments, the methods can use a particular ratio of metal precursors to provide the disclosed quantum dots. In some embodiments, a Group 11:Group 13 metal precursor molar ratio ranging from 1:1 to 1:5 can be used, such as 1:1 to 1:4, or 1:1 to 1:3, or 1:1 to 1:2. In exemplary embodiments, an Ag:In molar ratio of 1:2 or a Cu:In molar ratio of 1:2 can be used.

In some embodiments, the method can further comprise growing a shell on the quantum dot surface to enhance quantum yield. To enhance the quantum dot quantum yield (QY), a ZnS shell can grown on the quantum dot surface to form quantum dots having increased quantum yield as compared to quantum dots without a shell.

In an exemplary embodiment of the thermal decomposition methods disclosed herein, which is described solely by way of example, indium acetate and silver acetate or copper acetate can be reacted with a sulfur source, such as dodecanethiol, to form intermediate compounds of $Ag(SC_{12}H_{25})_x$ or $Cu(SC_{12}H_{25})_x$ and $In(SC_{12}H_{25})_x$ upon heating and are dissolved in dodecanethiol. As the reaction temperature is raised to a temperature ranging from 150° C. to 200° C. (e.g., 160° C. to 190° C., or 170° C. to 180° C.) the intermediate compounds can act as precursors and further decompose to form Ag—S or Cu—S and In—S to form Ag—In—S or Cu—In—S particles. Without being limited to a particular theory, it is currently believed that a 1:2 molar ratio of Cu:In or Ag:In can be used to circumvent the possibility of producing $Ag_2S$ or $Cu_2S$ particles. To further enhance the quantum yield, the AIS or CIS quantum dots can be passivated with a shell, such as a ZnS shell to form AIS/ZnS or CIS/ZnS quantum dots. In some embodiments, the core/shell quantum dots exhibited a significant quantum yield up to 41% but with a blue shift, as demonstrated in FIG. 1.

Embodiments of doped composites can be made using new synthetic methods disclosed herein that are reproducible and avoid multiple washing/drying steps and complex synthetic reactions. In particular disclosed embodiments, the methods use dopant precursors that are commercially available and relatively safe to use (e.g., no glove box is needed in preparing these precursors, and no highly restricted handling or disposal is required). In some embodiments, the methods described above for making the composites can be further modified to include a step whereby dopant precursors, such as CuI, $Mn(acetate)_2$, $Zn(acetate)_2$, $AgNO_3$, $Au(acetate)_3$, and the like, are added to composite solutions to provide surface-doped composites. In yet additional embodiments, doped composites comprising a core passivated with a shell can be made by coating and/or etching the shell components onto a doped core composition formed using a dopant precursor and a composite solution. Thus, in particular disclosed embodiments, a surface doping method is used, in contrast to a homogenous doping technique where the dopant is merely added to the precursors used to make the composite. The amount of dopant added can range from greater than 0 mol % to 15 mol %, such as from greater than 0 mol % to 10 mol %, or 3 mol % to 10 mol %, or 6 mol % to 10 mol %. In some representative embodiments, 3.33 mol %, 6.67 mol % and 10 mol % of the dopant can be added. In particular disclosed embodiments, a dopant precursor can be dissolved in a suitable solvent and then added dropwise to a solution comprising the un-doped composite. The composite solution can be heated to temperatures ranging from 120° C. to 200° C. or higher prior to addition of the dopant. After the dopant is added, the resulting reaction mixture can be cooled to ambient temperature. Methods for making doped core/shell composites can comprise preparing a doped composite as described above and then growing the shell on the doped core by adding selected shell precursors to a solution comprising the doped composite. In particular disclosed embodiments, the amount of the shell precursor added to the solution typically is an amount that would provide a sufficient number of shell atoms absorbed on to the surface of the doped composite; thus, in some embodiments, the amount can be determined based on the diameter of the doped composite. As an exemplary embodiment, doped core/shell composites can be obtained by preparing a shell precursor solution having a fixed concentration of the shell precursor, such as $Zn(acetate)_2$, and then injecting a selected volume of the shell precursor solution (e.g., 0.5 mL) into a reactor comprising the doped composite. In some embodiments, at least 1 to 20 injections, such as 1 to 15 injections, or 2 to 10 injections, or 4 to 9 injections of the shell precursor solution can be added. After each injection, the quantum yield of the composites can be assessed to provide a curve of quantum yield as a function of injection time. This curve can be used to obtain suitable injection times and the total amount of the precursor solution to be added to provide the desired core/shell doped composites.

The doping methods described above can be used to provide doped composites that exhibit high quantum yields (e.g., 50% or higher, such as 60% or higher) and prolonged photoluminescent lifetimes (e.g., 300 ns or more, such as 500 ns or more). The optical properties and material characteristics of the doped composites can be characterized using photoluminescence spectroscopy, UV-Vis spectroscopy, X-ray diffraction (XRD), transmission electron microscopy (TEM), energy-dispersive X-ray (EDX) spectroscopy, time-resolved photoluminescence spectroscopy, or combinations thereof.

V. Methods of Using Composites and Compositions

Figure 43:
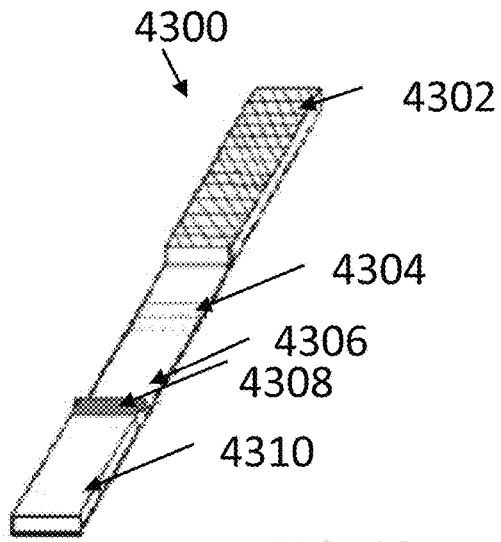
FIG. 43 is an illustration of a sensing probe as described herein.

The composites and compositions described herein can be used for biomedical imaging, biosensing, and therapeutic treatment. In some embodiments, the composites and compositions can be used for cell- or tissue-based diagnosis and therapy. For example, the composites and compositions can be used as contrast agents and/or probes for imaging cells, tumors, and/or detecting endogenous targets expressed in cells. In some embodiments, the compositions can comprise a composite and a biomolecule having therapeutic activity and/or a therapeutic drug and therefore the compositions can be used to treat, prevent, and/or ameliorate a disease or disorder. The disclosed composites and compositions are non-toxic, stable, and aqueous-soluble, and thus are suited for imaging of subjects both in vitro and in vivo as well as for drug delivery to a subject. In some embodiments, the composites and/or composite components (e.g., cores and/or zwitterionic polymer) can be used as imaging probes for flow cytometry, cell and tissue staining, cell tracking, Western blotting, in vivo imaging, and the like. In yet additional embodiments, the composites can be used as sensing probes. An exemplary sensing probe is illustrated in FIG. 43. According to the embodiment illustrated in FIG. 43, a sensing probe 4300 comprises an absorbent portion 4302, a capturing antibody portion 4304, a membrane (e.g., a nanocellulose membrane) 4306, a composite portion 4308, which comprising one or more of the composites disclosed herein, and a sample application portion 4310. Sensing probes like that illustrated in FIG. 43 can be used to detect the presence of a particular analyte of interest. When such sensors are used, the photoluminescence produced by the composite portion can be used as a signal under continuous excitation. As the composites exhibit long photoluminescence lifetimes, the time-resolved photoluminescence of these composites also can be used as signals. In such embodiments, the time-resolved photoluminescence signals are produced by exciting the composites with a pulse light source; after the pulse excitation light is switched off, the composites will still emit fluorescence for several hundred nanoseconds or longer. Such a time-resolved signal can avoid the interference of any background (autofluorescence).

In particular disclosed embodiments, the disclosed composites are combined with a biomolecule to produce a composition. The biomolecule can be coupled to the composite chemically, such as through a covalent or electrostatic bond. In some embodiments, the biomolecule can be covalently coupled to the composite using conjugation reagents and methods, such as by maleimide-thiol reaction chemistry, NHS-ester reaction chemistry, amino acid couplings, and the like. The coupling of the composite and the biomolecule can be evaluated and confirmed using FT-IR spectroscopy.

After conjugation of the composite and the biomolecule to form the composition, it can be administered to a subject or it can be exposed to a sample in vitro. The composition can be administered using any suitable administration route, such as oral administration, injection, topical administration, inhalation, or a combination thereof. In particular disclosed embodiments, the composition can further comprise a pharmaceutically acceptable carrier, such as water or other pharmaceutically acceptable solvent. In some embodiments, the composition can be administered as a solution, a dispersion, a tablet, or a capsule.

In some embodiments, the doped composites disclosed herein can be in various biomedical applications, such as cell targeting and imaging applications. In particular disclosed embodiments, the doped composites comprise a zwitterionic polymeric coating disclosed herein. These doped composites can be conjugated to targeting moieties, such as antibodies, haptens, peptides, a member of a specific binding pair, and other suitable targeting biomolecules. In particular disclosed embodiments, the doped composites can be coupled to peptides using peptide coupling reagents, such as, but are not limited to 2-(7-aza-1H-benzotriazol-1-yl)-N,N,N',N'-tetramethylaminium hexafluorophosphate, 2-(1H-benzotriazol-1-yl)-N,N,N',N'-hexafluorophosphate, 2-(6-chloro-1H-benzotriazol-1-yl)-N,N,N',N'-tetramethylaminium hexafluorophosphate, 1-hydroxybenzotriazole, dicyclohexylcarbodiimide, diisopropylcarbodiimide, N-(3-dimethylaminopropyl)-N'-ethylcarbodiimide-HCl, benzotriazol-1-yloxy-tris(dimethylamino)-phosphonium hexafluorophosphate, benzotriazol-1-yloxy-tripyrrolidino-phosphonium hexafluorophosphate, bromo-tripyrrolidino-phosphonium hexafluorophosphate, and the like, or a combination thereof. These peptide coupling reagents also can be used for other composites disclosed herein (that is, non-doped composites). In particular disclosed embodiments, the doped composites can be coupled to an RGD peptide for targeting tumors and/or mutations in brain cells, kidney cells, liver cells, breast tissue cells, and the like. In yet additional embodiments, the doped composites (and other composites disclosed herein) can be combined with therapeutics and/or image contrast agents to deliver drugs to particular targets within a subject and/or to provide additional imaging of such targets.

VI. Overview of Several Embodiments

Some embodiments disclosed herein concern composites comprising a core comprising one or more magnetic nanoparticles, one or more quantum dots, or a combination thereof; and a zwitterionic polymeric coating comprising a zwitterionic polymer having a structure satisfying a formula

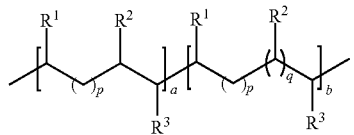

wherein each $R^1$ independently is selected from hydrogen or aliphatic; each $R^2$ is —C(O)Z, wherein Z is selected from hydroxyl, ether, amine, thiol, or thioether; each $R^3$ independently is selected from amide-aliphatic-amine, amide-aliphatic-amine-aliphatic-carboxylate, amide-aliphatic-amine-aliphatic-sulfonate, or amide-aliphatic-thiol; p is an integer selected from zero to 5; q is an integer selected from zero or 1; and each of a and b independently is an integer selected from 1 to 200. In some embodiments, the zwitterionic polymeric coating comprises a zwitterionic polymer having a structure satisfying a formula selected from

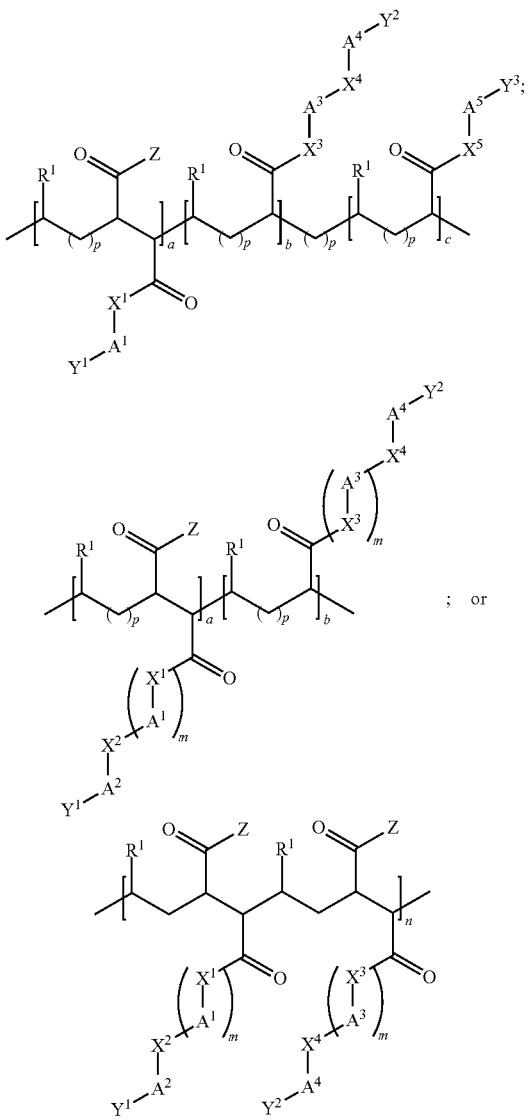

wherein each $R^1$ independently is selected from hydrogen or aliphatic; each of $X^1$, $X^2$, $X^3$, $X^4$, and $X^5$ independently is selected from $NR^b$, $N(R^b)_2^+$, oxygen, or sulfur, wherein each $R^b$ independently is selected from hydrogen, aliphatic, heteroaliphatic, aryl, or heteroaryl; each of $A^1$, $A^2$, $A^3$, $A^4$, and $A^5$ independently is selected from aliphatic or heteroaliphatic; each of $Y^1$, $Y^2$, and $Y^3$ independently is selected from amine, thiol, carboxylate or sulfonate; each Z independently is selected from hydroxyl, ether, amine, thiol, or thioether; n is an integer selected from 1 to 200; each m is an integer selected from 0 to 3; each p independently is an integer selected from zero to 5; each of a, b, and c independently is an integer selected from 1 to 200.

In any or all of the above embodiments, each $R^1$ independently is selected from hydrogen, alkyl, alkenyl, or alkynyl; each of $X^1$, $X^2$, $X^3$, and $X^5$ independently is selected from $NR^b$, $N(R^b)_2^+$, oxygen, or sulfur, wherein each $R^b$ independently is selected from hydrogen, alkyl, alkenyl, alkynyl, heteroalkyl, heteroalkenyl, heteroalkynyl, phenyl, naphthyl, or pyridinyl; each of $A^1$, $A^2$, $A^3$, $A^4$, and $A^5$ independently is selected from alkyl, alkenyl, alkynyl, heteroalkyl, heteroalkenyl, or heteroalkynyl; each of $Y^1$ and $Y^2$ independently is selected from carboxylate or sulfonate and $Y^3$ is thiol; each Z is hydroxyl; and m is 1.

In any or all of the above embodiments, the zwitterionic polymeric coating comprises a zwitterionic polymer have a structure

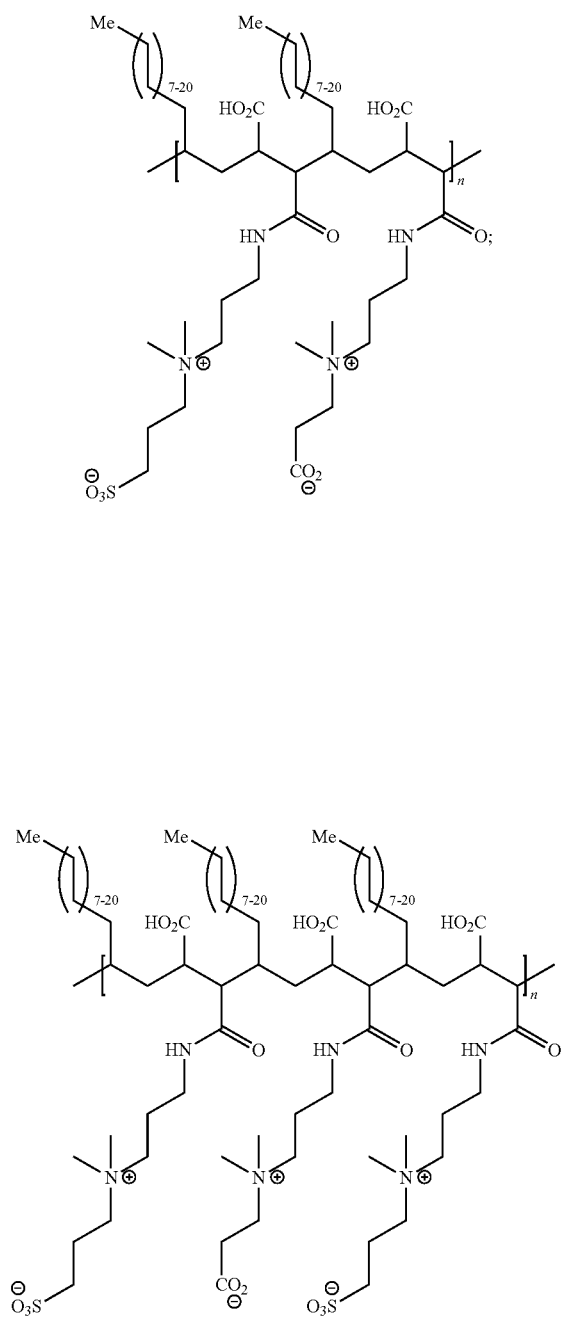

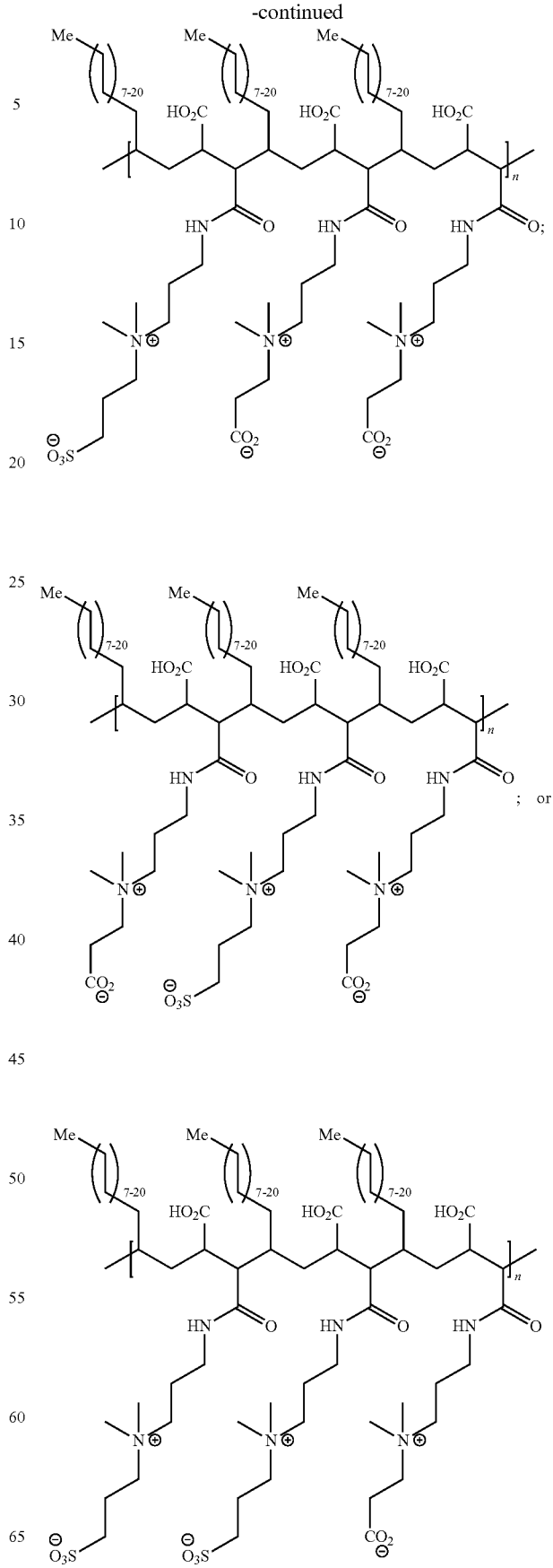

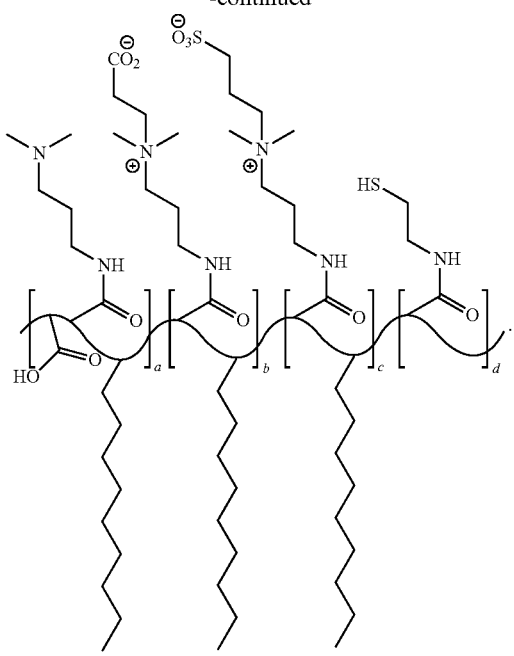

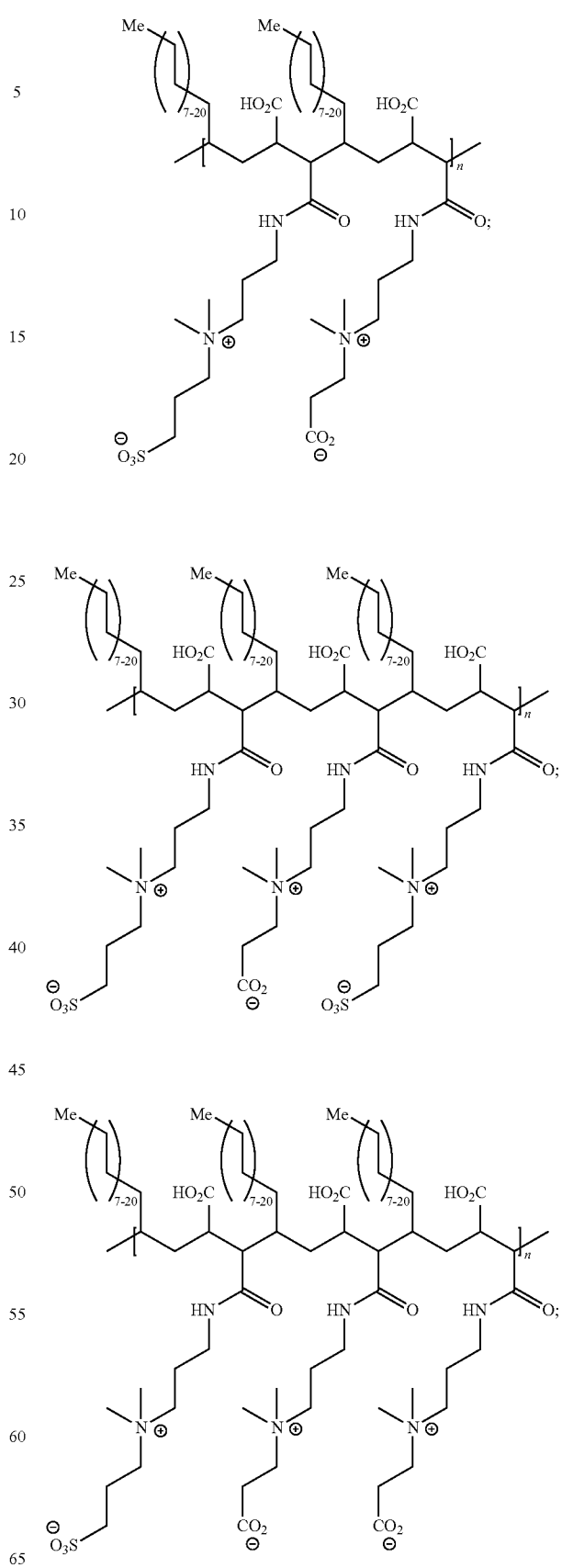

In any or all of the above embodiments, the core comprises at least one magnetic nanoparticle and at least one quantum dot.

In any or all of the above embodiments, the core is doped with a metal selected from Cu, Ag, Au, Mn, Zn, or combinations thereof. In some embodiments, the core is doped with greater than 0 mol % to 10 mol % of the metal.

In any or all of the above embodiments, the core is a quantum dot core and the quantum dot core comprises a ZnS shell. In some embodiments, the quantum dot core exhibits a quantum yield of greater than 50%. In any or both of these embodiments, the quantum dot core exhibits a photoluminescence lifetime ranging from 300 to 500 nanoseconds.

In any or all of the above embodiments, the quantum dot is a quantum dot.

In any or all of the above embodiments, wherein the quantum dot comprises copper or silver.

In any or all of the above embodiments, the quantum dot is an $AgInS_2$ quantum dot or a $CuInS_2$ quantum dot.

In any or all of the above embodiments, the quantum dot further comprises a ZnS shell.

In any or all of the above embodiments, the magnetic nanoparticle comprises Fe.

In any or all of the above embodiments, wherein the magnetic nanoparticle is $MnFe_2O_4$, $Fe_3O_4$, $CoFe_2O_4$, FePt or a combination thereof.

In any or all of the above embodiments, the core comprises a combination of $MnFe_2O_4$ nanoparticles and an $AgInS_2$ quantum dot, a $CuInS_2$ quantum dot, or a combination thereof.

Also disclosed herein are embodiments of composites comprising: a core comprising a combination of $MnFe_2O_4$ nanoparticles and $CuInS_2$ quantum dots, $AgInS_2$ quantum dots, or both; and a zwitterionic polymeric coating comprising a zwitterionic polymer having a structure selected from

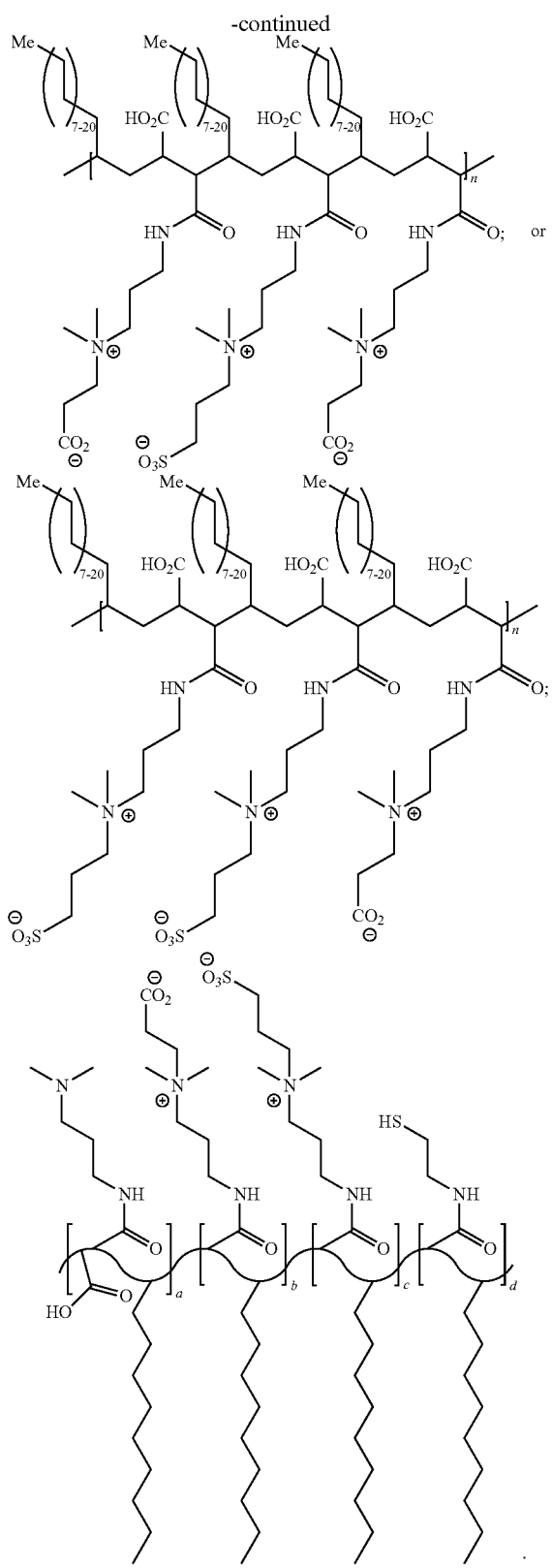

In any or all of the above embodiments, the core further comprises a dopant, a shell, or both. In some embodiments, the dopant is a metal selected from Cu, Ag, Au, Mn, Zn, or combinations thereof. In some or both of these embodiments, the shell is a ZnS or chloride shell.

Also disclosed herein are embodiments of compositions, comprising: a composite having a core comprising one or more magnetic nanoparticles, one or more quantum dots, or a combination thereof and a zwitterionic polymeric coating comprising a zwitterionic polymer having a structure satisfying a formula

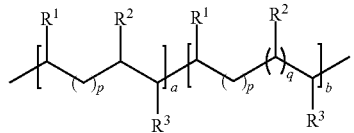

wherein each $R^1$ independently is selected from hydrogen or aliphatic; each $R^2$ is —C(O)Z, wherein Z is selected from hydroxyl, ether, amine, thiol, or thioether; each $R^3$ independently is selected from amide-aliphatic-amine, amide-aliphatic-amine-aliphatic-carboxylate, amide-aliphatic-amine-aliphatic-sulfonate, or amide-aliphatic-thiol; p is an integer selected from zero to 5; q is an integer selected from zero or 1; and each of a and b independently is an integer selected from 1 to 200; and a biomolecule, a drug, or a combination thereof. In some embodiments, the core further comprises a dopant, a shell, or both. In some or both of these embodiments, the dopant is a metal selected from Cu, Ag, Au, Mn, Zn, or combinations thereof.

In any or all of the above embodiments, the shell is a ZnS or a chloride shell.

In any or all of the above embodiments, the biomolecule is conjugated to the composite.

In any or all of the above embodiments, the biomolecule is chemically conjugated to the composite through the zwitterionic polymeric coating.

In any or all of the above embodiments, the biomolecule is chemically conjugated to the composite through a carboxylate group of the zwitterionic polymeric coating. In some embodiments, the carboxylate group of the zwitterionic polymeric coating is further chemically bound to a linker, wherein the linker is also chemically bound to the biomolecule.

In any or all of the above embodiments, the biomolecule is selected from chlorotoxin, avidin, biotin, folic acid, arginylglycylaspartic acid, or combinations thereof.

In any or all of the above embodiments, the drug is encapsulated within the zwitterionic polymeric coating.

In any or all of the above embodiments, the drug is doxorubicin, daunorubicin, epirubicin, idarubicin, or a combination thereof.

Also disclosed herein are embodiments of methods for making a composite, comprising: combining, to form a mixture, a solution comprising one or more magnetic nanoparticles, one or more quantum dots, or a combination thereof with a solution of a zwitterionic polymer having a structure satisfying a formula

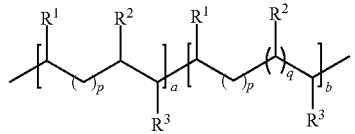

wherein each $R^1$ independently is selected from hydrogen or aliphatic; each $R^2$ is —C(O)Z, wherein Z is selected from hydroxyl, ether, amine, thiol, or thioether; each $R^3$ independently is selected from amide-aliphatic-amine, amide-aliphatic-amine-aliphatic-carboxylate, amide-aliphatic-amine-aliphatic-sulfonate, or amide-aliphatic-thiol; p is an integer selected from zero to 5; q is an integer selected from zero or 1; and each of a and b independently is an integer selected from 1 to 200; dispersing the mixture into water using sonication to form a dispersed composition; and isolating the composite from the dispersed composition.

In any or all of the above embodiments, the method further comprises centrifuging the dispersed composition to remove non-composite by-products.

Also disclosed herein are embodiments of methods for making a quantum dot, comprising: combining a Group 11 metal precursor with a Group 13 metal precursor, one or more ligands, a solvent, or a combination thereof to form a precursor mixture; and heating the precursor mixture to a temperature sufficient to facilitate formation of the quantum dot.

In any or all of the above embodiments, the Group 11 metal precursor is a copper-containing precursor, a silver-containing precursor, or a combination thereof.

In any or all of the above embodiments, the Group 11 metal precursor is copper acetate, silver acetate, or a combination thereof.

In any or all of the above embodiments, the Group 13 metal precursor comprises indium.

In any or all of the above embodiments, the Group 13 metal precursor is indium acetate.

In any or all of the above embodiments, a metal molar ratio of Ag:In of 1:2 or a metal molar ratio of Cu:In of 1:2 is used.

In any or all of the above embodiments, the temperature ranges from 150° C. to 200° C.

In any or all of the above embodiments, the temperature is 170° C.

In some embodiments, the methods comprise combining copper acetate, silver acetate, or a combination thereof with indium acetate, oleic acid, and dodecanethiol to form a precursor mixture; and heating the precursor mixture to a temperature ranging from 160° C. to 180° C. to facilitate formation of a CuInS$_2$ quantum dot, an AgInS$_2$ quantum dot, or a combination thereof.

Embodiments of methods of imaging cells also are disclosed herein, with such methods comprising: contacting a cell with an imaging amount of the composite having a core comprising one or more magnetic nanoparticles, one or more quantum dots, or a combination thereof and a zwitterionic polymeric coating comprising a zwitterionic polymer having a structure satisfying a formula

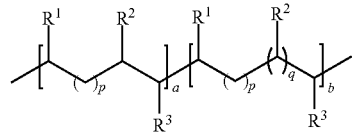

wherein each $R^1$ independently is selected from hydrogen or aliphatic; each $R^2$ is —C(O)Z, wherein Z is selected from hydroxyl, ether, amine, thiol, or thioether; each $R^3$ independently is selected from amide-aliphatic-amine, amide-aliphatic-amine-aliphatic-carboxylate, amide-aliphatic-amine-aliphatic-sulfonate, or amide-aliphatic-thiol; p is an integer selected from zero to 5; q is an integer selected from zero or 1; and each of a and b independently is an integer selected from 1 to 200; or a composition comprising the composite and a biomolecule, a drug, or both; and detecting cellular update and/or the location of the composite in the cell.

In any or all of the above embodiments, detecting the location of the composite comprises exposing the cell to a stain and visually imaging the cell to detect cellular uptake of the composite.

In any or all of the above embodiments, detecting the location of the composite comprises analyzing the cell using photoluminescence spectroscopy to determine the photoluminescent intensity of the composite.

Also disclosed herein are embodiments of a method of delivering a therapeutic drug to a subject, comprising: contacting the subject with a therapeutically effective amount of a composition comprising the therapeutic drug and a composite having a core comprising one or more magnetic nanoparticles, one or more quantum dots, or a combination thereof and a zwitterionic polymeric coating comprising a zwitterionic polymer having a structure satisfying a formula

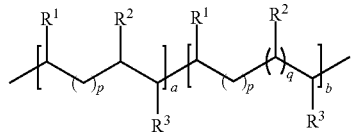

wherein each $R^1$ independently is selected from hydrogen or aliphatic; each $R^2$ is —C(O)Z, wherein Z is selected from hydroxyl, ether, amine, thiol, or thioether; each $R^3$ independently is selected from amide-aliphatic-amine, amide-aliphatic-amine-aliphatic-carboxylate, amide-aliphatic-amine-aliphatic-sulfonate, or amide-aliphatic-thiol; p is an integer selected from zero to 5; q is an integer selected from zero or 1; and each of a and b independently is an integer selected from 1 to 200.

In any or all of the above embodiments, therapeutic drug is encapsulated within the zwitterionic polymeric coating.

In any or all of the above embodiments, the drug is doxorubicin, daunorubicin, epirubicin, idarubicin, or a combination thereof.

VII. Examples

Materials

Poly(maleic anhydride-alt-1-octadecene (PMAO, average $M_n$ 30000-50000), 3-(dimethylamino)-1-propylamine (DMAPA, 99%), N,N-diisopropylethylamine (DIPEA, 99.5%), β-propiolactone (Grade II, ≥90%), gelatin, and poly-D-lysine (PDL) were purchased from Sigma-Aldrich. 1,3-propanesultone (99%) was purchased from Alfa Aesar. Tetrahydrofuran (THF, >99%), ethanol (>99%), methanol (>99%), dichloromethane and chloroform (>99.9%) were purchased from Pharmco-AAPER. U-87 MG (HTB-14) and HEK-293 cells (CRL-1537) were ordered from the American Type Culture Collection (ATCC). RPMI-1640, MEM and DMEM media were from Corning Cellgro. Paraformaldehyde, Dulbecco's phosphate buffered saline (DPBS), and phosphate buffered saline (PBS) were from Fisher Scientific. Heat-inactivated fetal bovine serum (FBS) and stempro accutase were from Gibco. Bovine serum albumin (BSA) was from MP Biomedicals. Chlorotoxin (CTX) was purchased from Alomone Labs. Fluorescein diacetate (FDA), propidium iodide (PI), 4',6-diamidino-2-phenylindole (DAPI) were was from Pierce. All chemicals or reagents were used as received without further purification.

The infrared (IR) spectra were acquired using a Perkin-Elmer Frontier FT-IR spectrometer equipped with Spectrum 10 software and Universal ATR sampling accessory. The nuclear magnetic resonance (NMR) spectra were obtained on Varian VNMRS operating at 500 MHz ($^1$H) and 298K. For the zwitterionic magnetofluorescent nanoparticle preparation, a probe-type Misonix Ultrasonic Liquid Processor (QSonica) was used. Transmission electron microscope (TEM) images and Energy-dispersive X-ray (EDX) spectra were acquired using a JEOL analytical transmission electron microscope (model JEM 2100F) operated with a 200 kV acceleration voltage and equipped with an Oxford Energy-Dispersive X-ray (EDX) spectrometer. The optical characteristics of zwitterionic magnetofluorescent nanoparticles including ultraviolet-visible (UV-Vis) and photoluminescence spectra were collected using Shimadzu UV-2450 spectrometer and Shimadzu RF-5301PC spectrofluorometer. The hydrodynamic sizes were measured in $H_2O$ using a Malvern Zetasizer Nano ZS dynamic light scattering (DLS) instrument equipped with a HeNe laser operating at 632.8 nm and a scattering detector at 173 degrees. For iron content assay and colloidal stability embodiments, a Perkin-Elmer microplate reader was used. Cell viability or cytotoxicity were estimated using a BD Biosciences SORP LSR II flow cytometer with 4 lasers (405 nm, 488 nm, 561 nm and 640 nm) and 18 fluorescence detectors. Magnetic resonance imaging was performed on a Bruker BioSpec 7T horizontal bore system. Fluorescent cellular images were taken using Leica TCS SP8 (DM 6000 CS) confocal scanning microscope.

Preparation of Zwitterionic Amphiphiles

Generally, the synthesis of zwitterionic amphiphilic polymer PMAO-carboxybetaine-sulfobetaine involved two steps. In the first step, PMAO anhydride rings were opened by the primary amine groups of DMAPA leading to the presence of terminal carboxyl and tertiary amine groups on the polymer backbone. In the second step, tertiary amines reacted with β-propiolactone and 1,3-propanesultone to form carboxybetaine and sulfobetaine groups, respectively. To avoid possible ring-opening polymerization of β-propiolactone and/or 1,3-propanesultone, the second-step reaction was started in ice-bath and the total molarity of both β-propiolactone and 1,3-propanesultone was controlled to be slightly higher than that of tertiary amines (if all anhydride rings in PMAO were opened). Of note, although the molar ratio between β-propiolactone and 1,3-propanesultone can be tuned, in this embodiment an 1:1 ratio of them was used to demonstrate the proof of concept on PMAO-carboxybetaine-sulfobetaine. The synthesis is simple, and its production yield is >80%.

In one example, PMAO-DMAPA was first prepared by stirring the mixture of 2.02 g PMAO and 1.1 mL DMAPA in 25 mL $CH_2Cl_2$ over ice-bath for 3 hours followed by precipitation of the product by adding acetone. The white precipitate was collected by filtration and then washed 3 times (with sonication) by dissolving in ~15-20 mL $CHCl_3$ and precipitating with acetone (3 times volume excess). The product was dried under vacuum overnight resulting in 2.03 g (~77% yield) of PMAO-DMAPA. For the synthesis of PMAO-DMAPA-carboxybetaine-sulfobetaine, the mixture of 0.50 g PMAO-DMAPA, 192 μL DIPEA, 38.4 μL of β-propiolactone, and 68.2 mg 1,3-propanesultone in 5 mL $CH_2Cl_2$ was stirred over ice-bath for ~3 hours and then at room temperature overnight. The resulting lightly cloudy mixture was pipetted into centrifuge tubes and washed (>5 times) by dissolving in ~1 mL $CHCl_3$-MeOH (1:1, v/v), precipitating with acetone (3-5 times volume) and collecting the precipitate by centrifugation. The white solid was dried under vacuum overnight giving 0.54 g of product (~88% yield).

The synthesized PMAO derivatives were characterized by FTIR, as shown in FIG. 2. PMAO-DMAPA spectrum showed the disappearance of anhydride C=O at around 1857 $cm^{-1}$ and 1776 $cm^{-1}$ and the appearance of new peaks at around 1713 $cm^{-1}$ for carboxyl C=O, around 1649 $cm^{-1}$ for amide C=O, and around 1560 $cm^{-1}$ for amide N—H, which indicates the addition of DMAPA to PMAO. In the spectrum of PMAO-carboxybetaine-sulfobetaine, the peaks from PMAO-DMAPA are represented and some new peaks at around 1175 $cm^{-1}$ and 1035 $cm^{-1}$ are observed. As shown in FIG. 3, the peaks at around 1175 $cm^{-1}$ and 1035 $cm^{-1}$ are also observed in the FTIR spectrum of amidosulfobetaine-16 (ASB-16) which is an alkyl chain with a sulfobetaine head. These two peaks represent S=O in the sulfo group. The spectrum comparison and analysis indicates the formation of sulfobetaine after the reaction of the tertiary amines of PMAO-DMAPA with 1,3-propanesultone. Peaks associated with carboxybetaine in PMAO-carboxybetaine-sulfobetaine are not significant for observation, probably because the peaks for the additional carboxyl C=O from the formed carboxybetaine groups in PMAO-carboxybetaine-sulfobetaine are overlapping with those of the existing carboxyl C=O in PMAO-DMAPA. However, a slight distortion at around 1590 $cm^{-1}$ in the spectrum of PMAO-carboxybetaine-sulfobetaine (not marked but close to the mark line at 1560 $cm^{-1}$) is still distinguishable. Considering there is a significant peak at around 1590 $cm^{-1}$ for N-Dodecyl-N,N-(dimethylammonio)butyrate (DDMAB) which is an alkyl chain with a carboxybetaine head (as shown in FIG. 1), this minor distortion may suggest the addition of carboxybetaine to PMAO.

Figure 5:
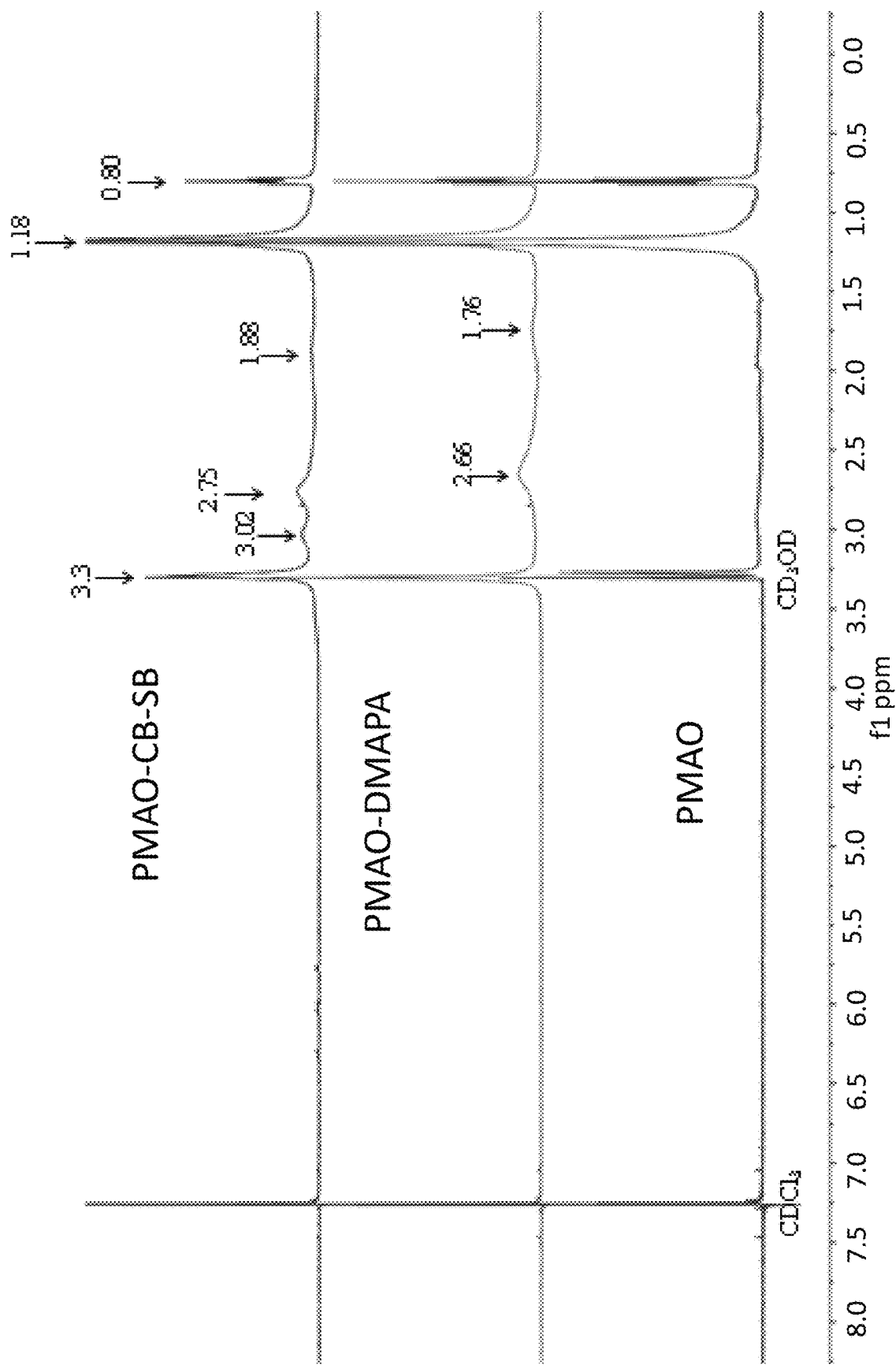
FIG. 5 is a combined $^1$H-NMR spectrum illustrating NMR spectra of a representative polymer precursor ("PMAO"), a representative polymer intermediate ("PMAO-DMAPA"), and a zwitterionic polymer ("PMAO-CB-SB").

The synthesized PMAO derivatives dissolved in a mixture of $CDCl_3$ and $CD_3OD$ were further characterized using NMR. All NMR spectra were presented in FIG. 5. For all samples, the hydrophobic alkyl chain ($C_{18}$) of the polymer was observed at 0.80 ppm for —$CH_3$ and 1.18 ppm for —$CH_2$. For PMAO-DMAPA, two additional peaks are presented at 2.66 ppm and 1.76 ppm. In literature, the following peaks have been reported for the attachment of DMAPA to polymer backbones: C(O)NHCH$_2$ at 3.2-3.3 ppm, CH$_2$N(CH$_3$)$_2$ at 2.36 ppm, N(CH$_3$)$_2$ at 2.2 ppm, CH$_2$CH$_2$N(CH$_3$)$_2$ at 1.6 ppm. The observed peaks due to the addition of DMAPA to PMAO appear in the chemical shift range as reported in the literature for the same chemical group. For PMAO-carboxybetaine-sulfobetaine, it has two peaks at 1.88 ppm and 2.75 ppm (similar to these of PMAO-DMAPA), but have an additional peak at around 3.02 ppm. Literature has reported the following peaks due to the carboxybetaine addition to polymer backbones: C(O)NHCH$_2$ at 2.75-3.48 ppm, C(O)NHCH$_2$CH$_2$ at 1.55-2 ppm, CH$_2$N$^+$(CH$_3$)$_2$ at 2.75-3.48 ppm, N$^+$(CH$_3$)$_2$ at 2.9-3.3 ppm, CH$_2$CH$_2$COO$^-$ at 3.4-3.55 ppm, CH$_2$COO$^-$ at 2.25-2.75 ppm; and the follow peaks due to the sulfobetaine addition to polymer backbones: C(O)NHCH$_2$ at 3.2 ppm, C(O)NHCH$_2$CH$_2$ at 1.9 ppm, CH$_2$N$^+$(CH$_3$)$_2$ at 3.3 ppm, N$^+$(CH$_3$)$_2$ at 3.05-3.1 ppm, CH$_2$CH$_2$CH$_2$SO$_3^-$ at 3.4 ppm, CH$_2$CH$_2$SO$_3^-$ at 2.15 ppm, and CH$_2$CH$_2$SO$_3^-$ at 2.89 ppm. The peaks for PMAO-carboxybetaine-sulfobetaine match with what were reported.

For the synthesis of PMAO-DMAPA-CBSB, PMAO-DMAPA (0.50 g) was first dissolved in 5 mL of anhydrous $CHCl_3$ and then cooled over ice-$H_2O$ bath. Then, DIPEA (192 μL, 1.1 mmole) was added and the mixture stirred for 5 minutes before adding β-propiolactone (38.4 μL, 0.55 mmole), and 1,3-propanesultone (67.9 g, 0.55 mmole). The reaction mixture was stirred over ice-$H_2O$ bath for 3 hours and then at room temperature overnight. The resulting lightly cloudy mixture was pipetted into centrifuge tubes and washed (7×) by dissolving in ~1 mL $CHCl_3$-MeOH (1:1, v/v), precipitating with acetone (3-5× volume) and collecting the precipitate by centrifugation. The white solid was dried under vacuum overnight giving 0.54 g of product.

For the alternative approach for the introduction of carboxybetaine group, PMAO-CBtBu was first prepared by stirring the mixture of PMAO-DMAPA (0.50 g), DIPEA (0.40 mL, 2.3 mmol), and tert-butyl bromoacetate (0.52 mL, 3.4 mmole) in 5 mL of anhydrous $CHCl_3$ at room temperature overnight. The clear reaction mixture was poured into 50 mL anhydrous $Et_2O$ to precipitate the product. The white precipitate was collected and washed with 15 mL $Et_2O$ (3×) and dried under vacuum giving 1.0 g of product. As the product weighed more than expected, it was re-washed with 10 mL acetone (3×), but much less solid was isolated and the product was found to have dissolved in acetone, as solids were collected after rotary evaporation of the acetone filtrate (0.96 g). The product isolated from evaporation of acetone was used without further purification for the next reaction. It was stirred with 1.2 mL TFA under Argon for 1 h to hydrolyze the tert-butyl ester group. The product (PMAO-CB) was precipitated and washed with anhydrous $Et_2O$, and then dried under vacuum (0.63 g) and further washed with acetone giving 0.55 g of white solid after drying.

In some embodiments, amino intermediates comprising CB and SB units can be made and then used to open maleic anhydride-containing polymers. The primary amine of DMAPA was first protected by reaction with di-tert-butyl dicarbonate (Boc anhydride) to obtain Boc-DMAPA. The reaction of Boc-DMAPA with β-propiolactone (or 1,3-propanesultone) was followed by acid treatment to remove the protecting group and obtain the corresponding acid salt of amino-CB (or amino-SB). The obtained intermediates were characterized by $^1H$ NMR spectroscopy and confirmed by comparison with literature data when available.

The obtained Boc-DMAPA was reacted with 1,3-propanesultone, which was followed by acid hydrolysis of Boc protecting group to get the corresponding acid salt of amino-SB. The $^1H$ NMR of the product showed the disappearance of the signal at 1.44 ppm (compared with Boc-DMAPA) which indicates the removal of the Boc protecting group. The proton peaks were also assigned as indicated below. The products/intermediates for the synthesis of amino-SB were also characterized by FTIR spectroscopy. The addition of 1,3-propanesultone to Boc-DMAPA is indicated by the more prominent peaks at 1163 $cm^{-1}$ (overlapping with C—N vibration) and 1033 $cm^{-1}$ for S=O of the sulfonic group. The removal of the Boc protecting group is confirmed by the disappearance of the peaks at 1694 $cm^{-1}$ and 1528 $cm^{-1}$ from the C=O and N—H, respectively, of Boc-DMAPA.

The amino-CB was alternatively prepared from the reaction between Boc-DMAPA and tert-butyl bromoacetate, which is eventually followed by acid hydrolysis of the tert-butyl groups to give the corresponding acid salt of amino-CB. The $^1H$ NMR spectrum of the product showed the disappearance of the tert-butyl groups at 1.54 and 1.45 ppm, indicating the deprotection (removal of Boc and tert-butyl ester groups) by acid hydrolysis.

The isolated products/intermediates for amino-CB were also characterized by FTIR spectroscopy. For the reaction of Boc-DMAPA and t-butyl bromoacetate, the appearance of overlapping peaks at 1740 $cm^{-1}$ and 1691 $cm^{-1}$ are for the C=O of butyl ester and the C=O of Boc group, respectively. The peaks at 1249 $cm^{-1}$ and 1152 $cm^{-1}$ are for the C—O vibration of the t-butyl ester group which disappeared after removal of the protecting groups via HCl hydrolysis, along with the peak at 1691 $cm^{-1}$ from removal of Boc protecting group. The C=O for amino-CB (acid salt) is found to have shifted to 1740 $cm^{-1}$ corresponding to that for carboxylic acid. The broad peak at 2800 $cm^{-1}$, aside from containing the C—H, also represents the O—H from the carboxylic group.

The protection of the primary amine of DMAPA was done by stirring (under Ar) the solution of DMAPA (5 mL, 39.3 mmole) in 21 mL anhydrous MeOH and di-tert-butyl dicarbonate (Boc anhydride, 9.6 mL, 41.4 mmole) over ice/$H_2O$ bath for at least 1 hour and then allowing mixture to reach room temperature and continued stirring overnight. Bubbling (from formation of $CO_2$) occurred during the addition of Boc anhydride. The resulting clear, colorless solution was concentrated by rotary evaporation, dissolved in 30 mL $H_2O$, and then washed with EtOAc (25 mL×5). The combined EtOAc washes was dried over anhydrous $Na_2SO_4$, filtered to remove the drying agent, and the filtrate concentrated by rotary evaporation. The residue was dried under vacuum giving 5.64 g (71% yield) of colorless oil.

To synthesize the sulfobetaine intermediate, Boc-DMAPA (2.51 g, 12.4 mmole) was dissolved in 15 mL of anhydrous DMF and then 1.56 mL (2.13 g, 17.4 mmol) of 1,3-propanesultone (1.56 mL, 17.4 mmole) was added. The clear, colorless solution was stirred at room temperature for 2 days. The resulting clear reaction mixture was added to 100 mL of anhydrous $Et_2O$ to precipitate the product, which came out as viscous material. After cooling the mixture in the freezer for 1 hour, the lightly cloudy supernatant was decanted. The wash was repeated (2 more times) by dissolving the residue in MeCN, adding $Et_2O$, cooling in the freezer, and decantation of the supernatant. The viscous residue was transferred into a pre-weighed flask using MeCN, concentrated by rotary evaporation, and dried under vacuum overnight giving 4.51 g (112% yield) of white, foamy residue. The sample was re-washed using MeCN and $Et_2O$ (3×) resulted to 4.39 g (109% yield) of foamy residue after drying. Although the sample weighed more than expected, it was used as is for the acid hydrolysis of the Boc protecting group using aqueous HCl. Boc-DMAPA-SB (4.15 g, 12.8 mmole) was dissolved in 11 mL of $H_2O$ and 5.3 mL of concentrated HCl (~5× excess) was added, during which bubbling occurred. The mixture was stirred (loosely stoppered) at room temperature overnight. The sample was concentrated by rotary evaporation (remaining HCl/$H_2O$ was co-evaporated with 10 mL $Et_2O$ (3×)) and the residue dried under vacuum giving 4.21 g of viscous residue. The product was re-stirred with 30 mL of 4 M HCl in MeOH for 4 hours, concentrated with rotary evaporation (with $Et_2O$ co-evaporation) and then dried under vacuum giving 4.67 g of faintly yellow oil. The sample was used as is for reaction with PMAO. For the remaining sample, several trials were done to isolate the HCl salt as a solid. Eventually, the sample (3.34 g) was dissolved in 10 mL MeOH and $CH_2Cl2$/iPrOH/MeOH (10:5:1, volume ratio) was added in portions (used 45 mL) at which a solid mass collected at the bottom of the flask. The sample was washed with $CH_2Cl2$/iPrOH/MeOH (10:5:1, volume ratio) and after drying under vacuum a white solid was obtained. The sample was transferred into a fitted funnel by repeatedly washing with $CH_2Cl_2$/iPrOH/MeOH (10:5:1, volume ratio) (with sonication), and after drying under vacuum, 2.04 g of white solid was obtained.

For the synthesis of the carboxybetaine intermediate, Boc-DMAPA (1.26 g, 6.23 mmole) was dissolved in 6 mL anhydrous MeCN and then tert-butyl bromoacetate (1.31 mL, 8.72 mmole) was added. The mixture was stirred at 50° C. (oil bath temperature) for 24 hours. After cooling to room temperature, the reaction mixture was added to $Et_2O$ to precipitate the product, which came out as viscous residue. The mixture was cooled in the freezer for 1 hour and the supernatant was decanted. The wash was repeated (2 more times) by dissolving the residue in MeCN and adding $Et_2O$. The residue was transferred into a pre-weighed flask using MeCN, concentrated by rotary evaporation, and then dried under vacuum overnight giving 2.32 g of white, foamy residue. The product was used as is for the next reaction, which is the acid hydrolysis of Boc and t-Bu ester groups using aqueous HCl. Boc-DMAPA-CB-tBuester (2.17 g) was dissolved in 10 mL of $H_2O$ and 4.6 mL of concentrated HCl (~5× excess) was added, during which bubbling occurred. The mixture was stirred (loosely stoppered) at room temperature for 2 hours. The mixture was concentrated by rotary evaporation (with $Et_2O$ co-evaporation) and then dried under vacuum giving 1.58 g of viscous residue. The NMR spectrum showed that the Boc and t-Bu groups were gone. In the attempt to recover the product as a solid, the sample was re-stirred with 15 mL of 4M HCl in MeOH for 2 hours, concentrated by rotary evaporation (with $Et_2O$ co-evaporation), and rinsed with acetone. After drying under vacuum, solid sample was obtained. The sample was transferred into a fritted funnel by repeated washing (with sonication) with $Et_2O$ and then $CH_2Cl_2$/iPrOH/MeOH (10:5:1, volume ratio) and then dried under vacuum giving 0.99 g of white solid.

For the synthesis of PMAO-CBSB, PMAO (100 mg, 2.5 μmole, ~285 μmole anhydride) was dissolved in 5 mL anhydrous $CHCl_3$. In a separate container, amino-SB (HCl salt, 42 mg) and amino-CB (HCl salt, 33 mg) were mixed with 500 μL anhydrous MeOH (some undissolved solid present). DIPEA (300 μL) was added to convert the intermediates to the free base form, resulting in a clear, colorless solution. The solution of amino-SB and amino-CB was added to PMAO and the mixture stirred at room temperature for 24 hours. The reaction mixture was concentrated by rotary evaporation and the residue dissolved in $CHCl_3$-MeOH (1:1, v/v). The product was precipitated by adding acetone and collected by centrifugation. The dissolution in $CHCl_3$-MeOH and precipitation with acetone was repeated 2 more times and the residue dried under vacuum giving 144 mg of white solid.

Preparation of Zwitterionic Magnetofluorescent Nanoparticles

Figure 4:
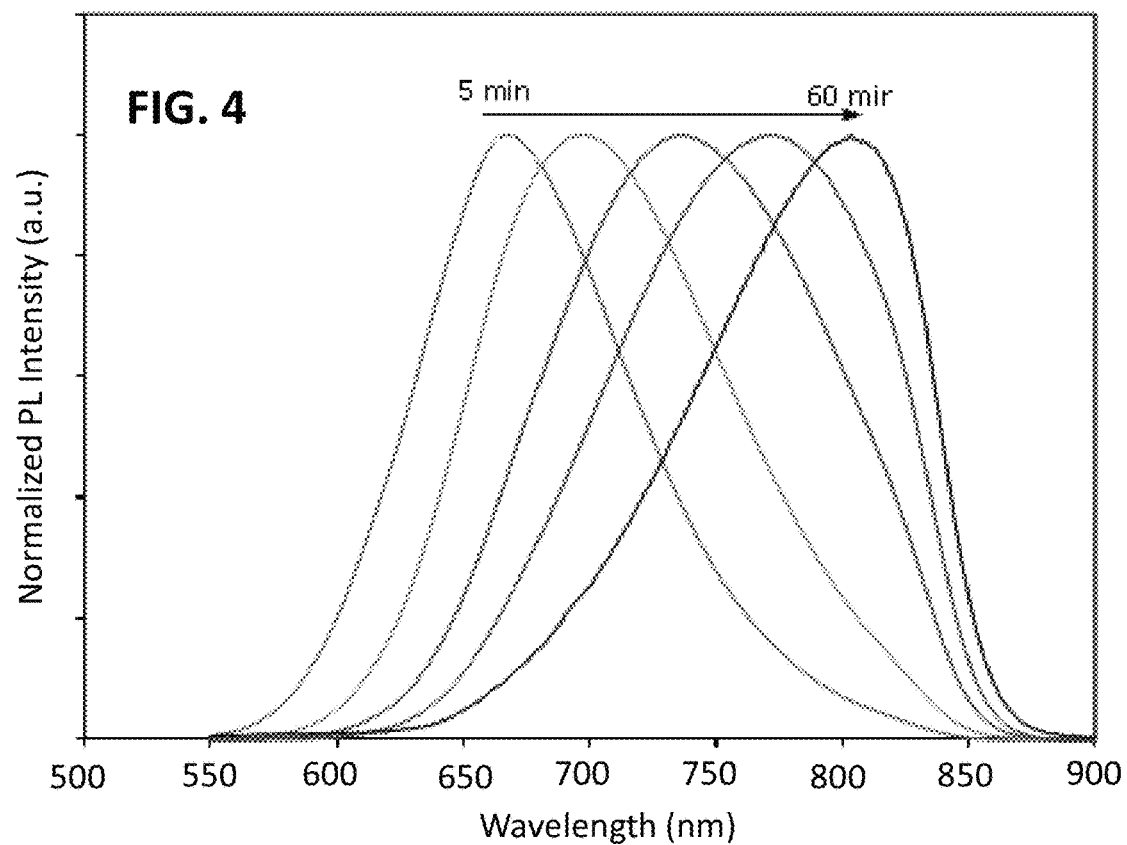
FIG. 4 is a graph of normalized photoluminescence intensity (a.u.) as a function of wavelength (nm) illustrating representative and normalized photoluminescence intensity of CIS quantum dots in the time course of growth at 240° C.

On the basis of the synthesized PMAO-carboxybetaine-sulfobetaine, zwitterionic magnetofluorescent nanoparticles integrating small $MnFe_2O_4$ magnetic nanoparticles and $CuInS_2$/ZnS quantum dots in the micellar cores were fabricated. Magnetic nanoparticles and quantum dots were around 5 nm. Using the disclosed methods to produce composites comprising quantum dots, the quantum dot photoluminescence can be tuned from 650 nm-800 nm (FIG. 4). In one example, $CuInS_2$ quantum dots with around 720 nm photoluminescence emission were prepared, and after ZnS shell growth the $CuInS_2$/ZnS quantum dots emit photoluminescence at around 685 nm. A solution of 0.6 mg $MnFe_2O_4$ magnetic nanoparticles and 2.4 mg $CuInS_2$/ZnS quantum dots in THF (900 μL) and 1.7 mg PMAO-carboxybetaine-sulfobetaine in $CHCl_3$-MeOH (~50 μL) was layered on top of cold water in a glass vial. The mixture was ultrasonicated using the Misonix Ultrasonic Liquid Processor with a 5 W output power for 1 minute. After sonication, the organic solvents were removed by rotary evaporation at room temperature and the sample filtered through a 0.2 μm syringe filter. Empty micelles or single-nanoparticle based micelles were removed by centrifugation at 18,000 rpm for 25 min (twice). The collected zwitterionic magnetofluorescent nanoparticles were dispersed in 400 μL of water, and stored at 4° C. until further use.

Figure 6A:
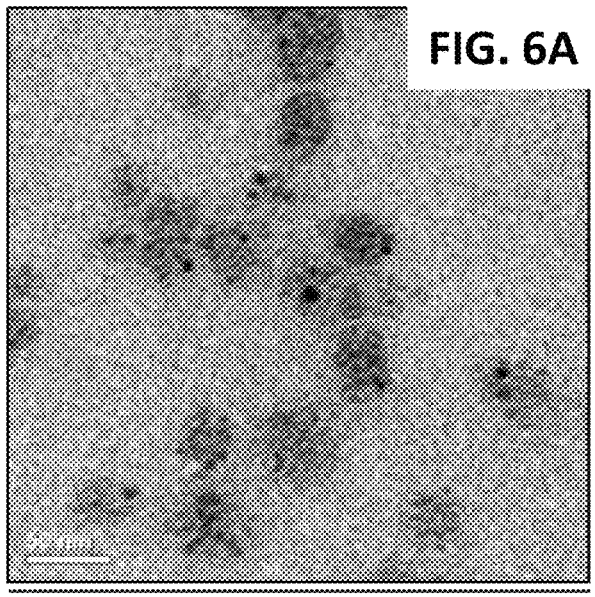
FIGS. 6A-6C illustrate TEM and EDX images of representative composite cores.
Figure 6B:
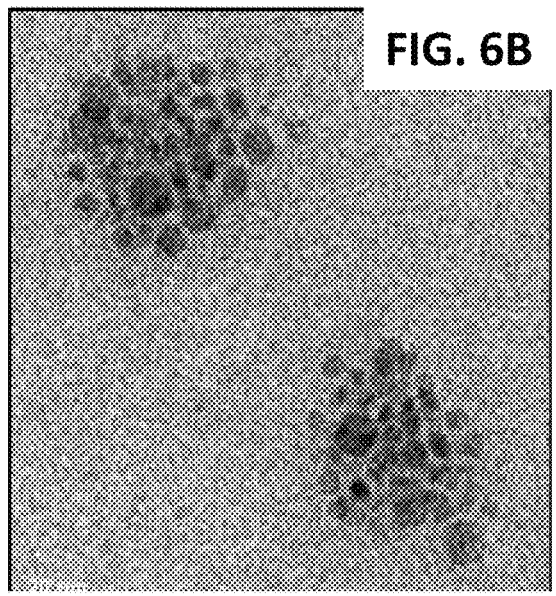
Figure 6C:
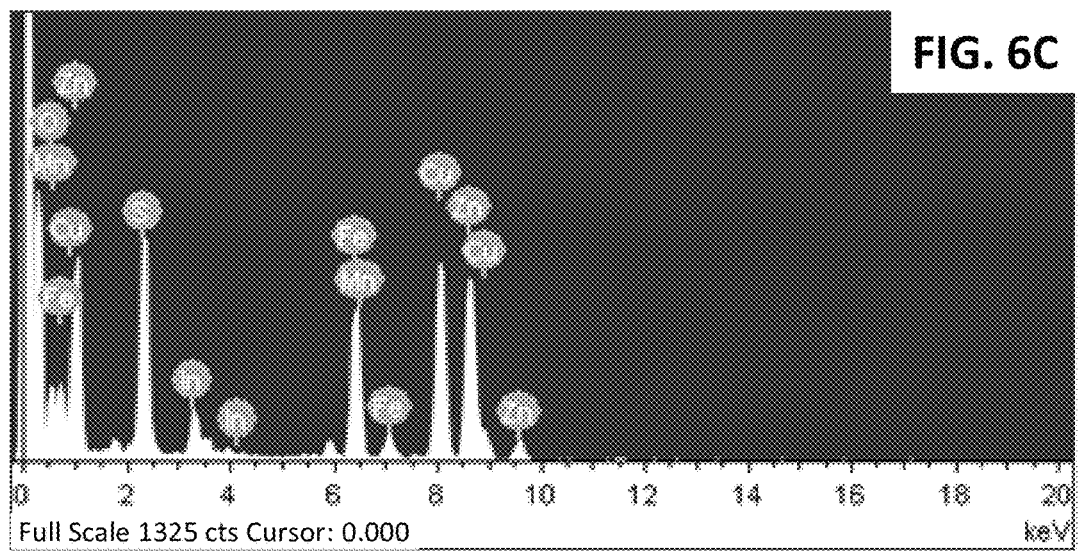

The fabricated zwitterionic magnetofluorescent nanoparticles were characterized using TEM and EDXS. FIGS. 6A and 6B present TEM images of zwitterionic magnetofluorescent nanoparticles, and the images indicate the sizes of zwitterionic magnetofluorescent nanoparticles in around 50~60 nm. On the basis of TEM imaging, the overall size of zwitterionic magnetofluorescent nanoparticles mostly distributed over a range of 20~150 nm was observed. EDX analysis in FIG. 6C further demonstrates that zwitterionic magnetofluorescent nanoparticles are composed of Mn, Fe, O, Cu, In, Zn and S elements. In addition to TEM, DLS data of zwitterionic magnetofluorescent nanoparticles have been collected and presented in Table 1. The hydrodynamic sizes of zwitterionic magnetofluorescent nanoparticles are 99 nm with a standard deviation at 60 nm. The zwitterionic magnetofluorescent nanoparticle hydrodynamic sizes mainly are contributed by the micelle hydrophobic core (imaged by TEM), the polymer shell, and the hydration layer caused by zwitterions on the polymer shell. The (Mn+Fe) content in zwitterionic magnetofluorescent nanoparticles was also quantified on the basis of the iron content determination of zwitterionic magnetofluorescent nanoparticles using thiocyanate colorimetry. Table 1 also shows that the (Mn+Fe) recovery rate for 0.6 mg magnetic nanoparticles input to zwitterionic magnetofluorescent nanoparticles is as high as around 60%.

TABLE 1

Hydrodynamic sizes and (Mn + Fe) recovery rates of zwitterionic magnetofluorescent nanoparticles and zwitterionic magnetic nanoparticles

| Particles | Hydrodynamic sizes (nm) | (Mn + Fe) recovery rates (%) |
|---|---|---|
| zwitterionic magnetofluorescent nanoparticles | 99 ± 60 | 62 ± 1 |
| zwitterionic magnetic nanoparticles | 133 ± 69 | 60 ± 4 |

Figure 8A:
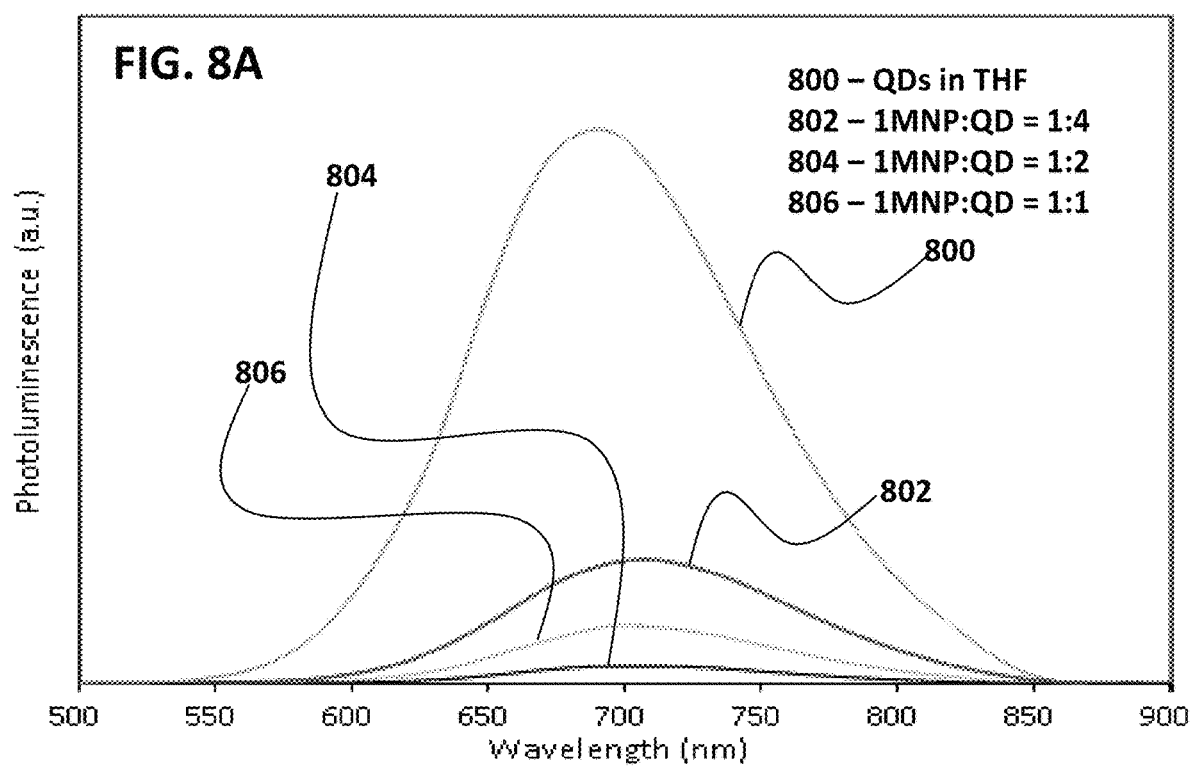
FIGS. 8A and 8B illustrate results obtained from analysis of representative composites.
Figure 8B:
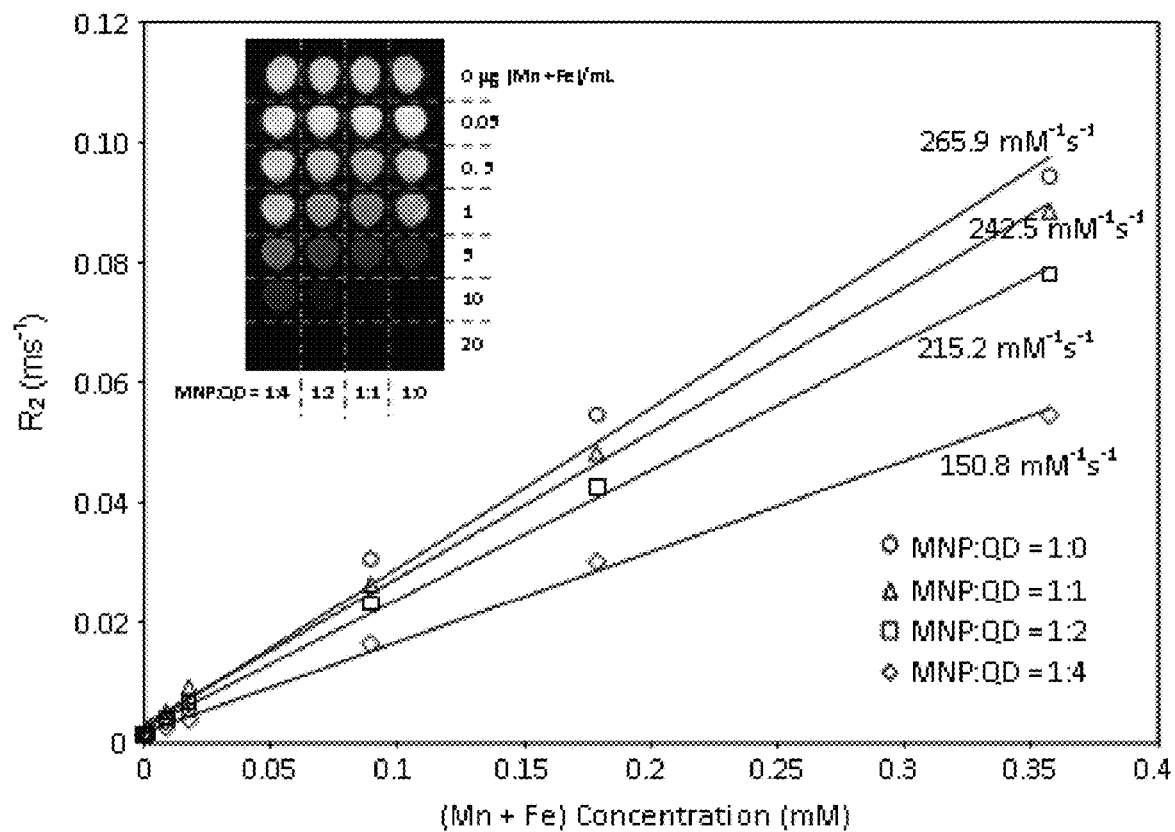
Figure 9:
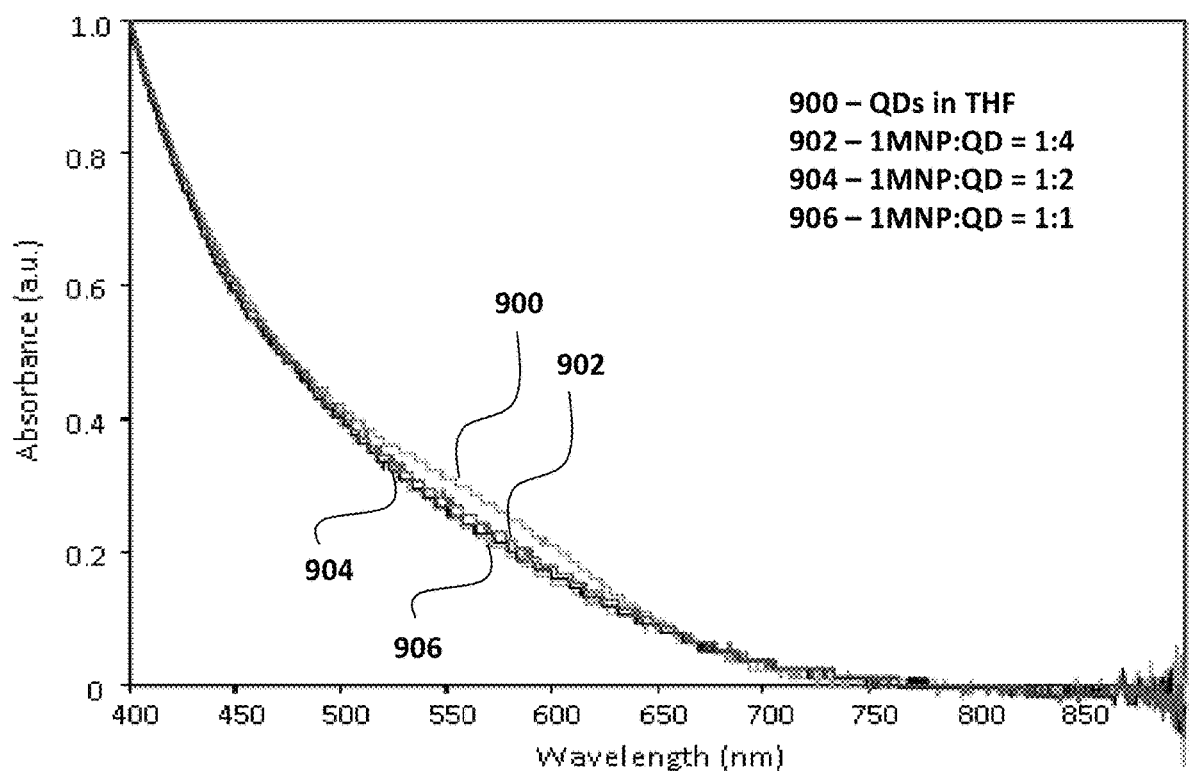
FIG. 9 illustrates the UV-Vis absorbance spectra of quantum dots in THF and representative water-soluble composites.

The photoluminescence spectrum of zwitterionic magnetofluorescent nanoparticles is shown in FIG. 7A, compared to that of quantum dots in organic solvents. The photoluminescence intensities are scaled by the quantum yield of zwitterionic magnetofluorescent nanoparticles relative to that of hydrophobic quantum dots in THF (the measured quantum yields of zwitterionic magnetofluorescent nanoparticles are <10%). It can be seen that the photoluminescence of zwitterionic magnetofluorescent nanoparticles is significantly quenched. The quenching may be caused by the MNP absorption on quantum dot emissions, or by the reduction of quantum dot excitation/emission surfaces due to the blocking effect of surrounding magnetic nanoparticles. FIGS. 7A and 7B also show that the overall photoluminescence property of zwitterionic magnetofluorescent nanoparticles are tunable by adjusting the MNP:quantum dot mass ratio in the fabrication process. Additional embodiments are illustrated in FIGS. 8A and 8B. The absorbance of the prepared zwitterionic magnetofluorescent nanoparticles was characterized using a UV-Vis spectrophotometer, as shown in FIG. 9. No significant difference on UV-Vis absorbance curves was observed for all fabricated zwitterionic magnetofluorescent nanoparticles.

The magnetic imaging features of magnetofluorescent nanoparticles were characterized using a magnetic resonance imaging (MRI) instrument (Bruker BioSpec). The MR images of zwitterionic magnetofluorescent nanoparticles were acquired with a conventional spin echo acquisition (TR=6000 ms) with TE values ranging from 9.5 ms to 190 ms. $T_2$ parameter (or $R_2$ parameter, $R_2=1/T_2$) of zwitterionic magnetofluorescent nanoparticles was extracted by fitting the exponential decay of the signal waveform and measuring the signal intensity at a series of different TE values. FIG. 7B presents $R_2$ parameter (or $1/T_2$) of zwitterionic magnetofluorescent nanoparticles vs (Mn+Fe) concentration. The relaxivity ($r_2$) of zwitterionic magnetofluorescent nanoparticles was calculated as the slope of the $R_2$ curve. The relaxivity $r_2$ value of zwitterionic magnetofluorescent nanoparticles is around 150 mM$^{-1}$s$^{-1}$. $R_2$ parameter of zwitterionic magnetic nanoparticles (using magnetic nanoparticles and the synthesized zwitterionic amphiphiles but not containing any quantum dots) also was measured as a comparison. The relaxivity $r_2$ of zwitterionic magnetic nanoparticles is around 266 mM$^{-1}$s$^{-1}$. In literature, $T_2$ parameter of agglomerated nanomagnet clusters has been formulated and discussed. Briefly, for agglomerated nanomagnets, $1/T_2=16f_a\Delta\omega^2\tau_D/45$ with $f_a$ being the volume fraction occupied by the agglomerated nanomagnets, $\Delta\omega=\mu_o M\gamma/3$ (where $\mu_o$ is the vacuum magnetic permeability, M is the particle magnetization, and γ is the proton gyromagnetic ratio), and $\tau_D$ is the translational diffusion time around the cluster ($\tau_D=R_a^2/D$ where $R_a$ being the cluster radius and D being the water diffusion coefficient). Although the formula of $T_2$ parameter discussed for the agglomerated system is built only on small magnetic nanoparticles, it can be applicable to zwitterionic magnetofluorescent nanoparticles with a mixture of quantum dots and magnetic nanoparticles. Specifically, $f_a$ probably can be re-defined as the volumic fraction occupied by magnetic nanoparticles in zwitterionic magnetofluorescent nanoparticles. Considering zwitterionic magnetofluorescent nanoparticles and zwitterionic magnetic nanoparticles have the similar size ranges (as shown in Table 1), the increase of quantum dots over magnetic nanoparticles in the fabrication may cause the decrease of $f_a$, which further result in the total net magnetization (M) of zwitterionic magnetofluorescent nanoparticles to drop. Thus, quantum dots involved in the fabrication cause $R_2$ and thus $r_2$ decrement of zwitterionic magnetofluorescent nanoparticles. In spite of the $R_2$ or $r_2$ drop, the relaxivity value for zwitterionic magnetofluorescent nanoparticles is still comparable to many reported ones. Of note, the fabricated zwitterionic magnetic nanoparticles also can be considered as excellent contrasts for MRI because of their high magnetic relaxivity and (Mn+Fe) recovery rate.

Cell Cytotoxicity of Magnetofluorescent Nanoparticles

Figure 10:
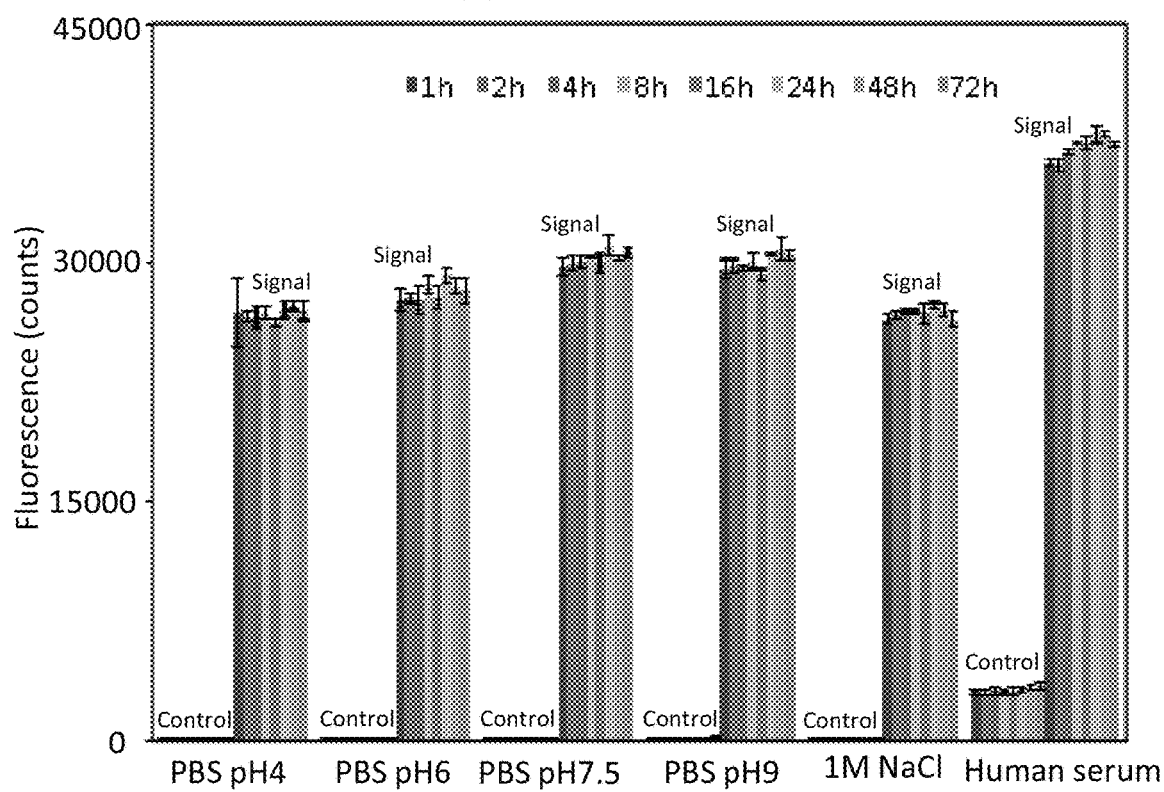
FIG. 10 is a bar graph of fluorescence stability of representative composites in PBS solutions at pH values ranging from 4-9, which illustrates the colloidal stability of the composites in aqueous solutions.
Figure 11:
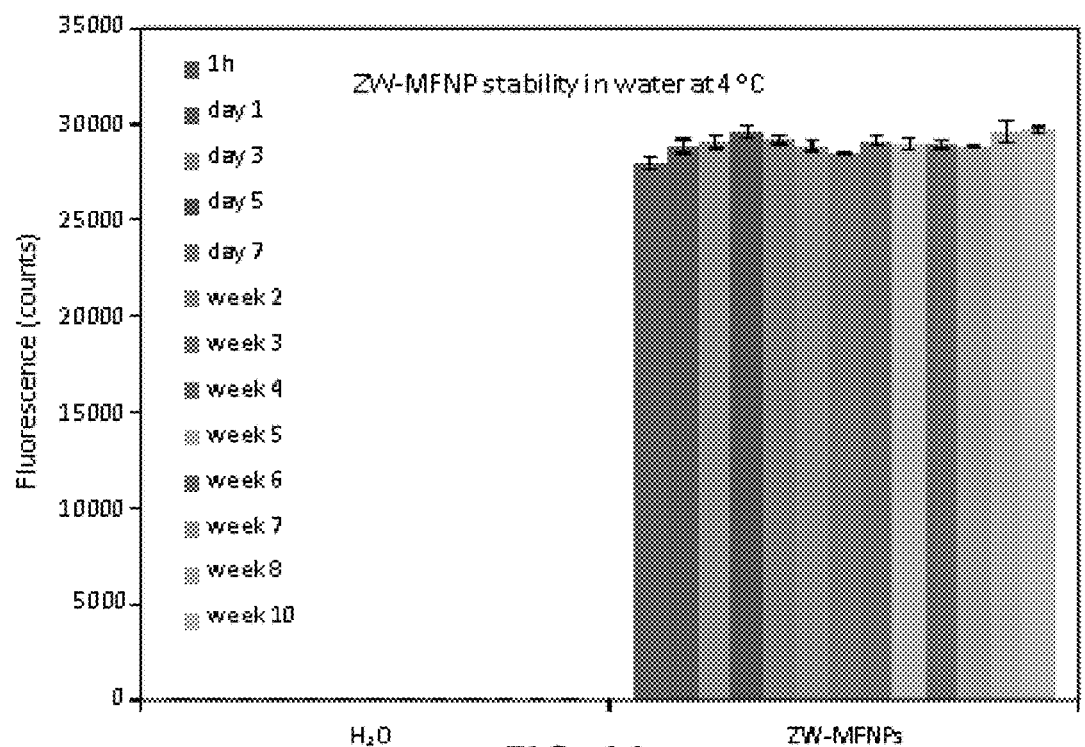
FIG. 11 is a bar graph of fluorescence stability of representative composites in water at 4° C.
Figure 12:
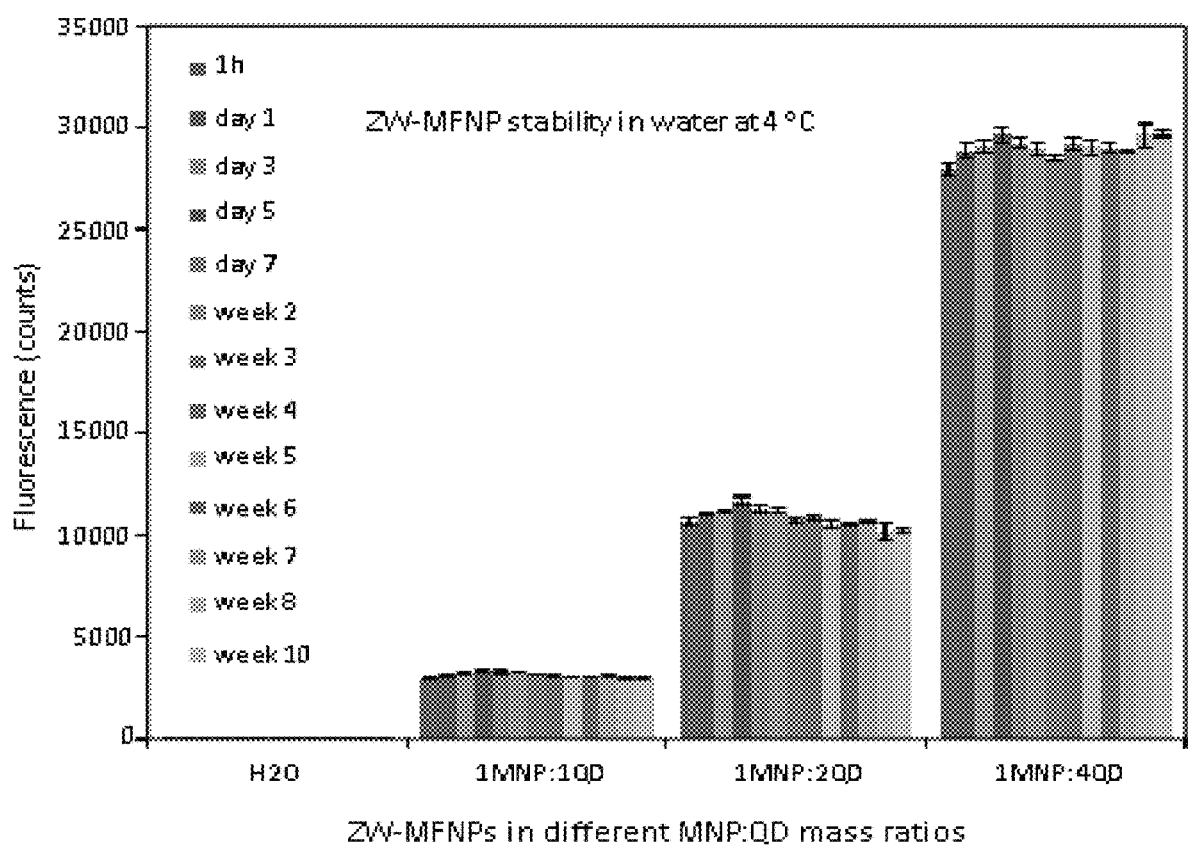
FIG. 12 is a bar graph of long-term stability of representative composites in water at 4° C.

In biosensing/imaging applications, aggregation of zwitterionic magnetofluorescent nanoparticles will cause the degradation or even loss of their physiochemical and biological functionalities, and thus zwitterionic magnetofluorescent nanoparticles are expected to have excellent colloidal stability. The photoluminescence intensity of zwitterionic magnetofluorescent nanoparticles dispersed in PBS-5% FBS with pH 4-9, a 1 M NaCl-5% FBS and human serum was monitored over 72 hours at 37° C. using a microplate reader, and presented in FIG. 10. With reference to FIG. 10, the different time periods included in the legend correspond to different bars present for each pH value shown on the graph, as read from left to right for the time and for each bar. That is, each group of bars for each pH value is ordered by increasing time period from left to right. For example, the left-most bar of each pH bar set corresponds to 1 hour and the right most bar of each pH bar set corresponds to 72 hours. The photoluminescence intensity and hence stability of these zwitterionic magnetofluorescent nanoparticles was maintained in all these conditions. Moreover, no precipitates or significant photoluminescence intensity decreases were observed over one week at 37° C. Stored at 4° C., the zwitterionic magnetofluorescent nanoparticles were also found to be stable in water at over at months (FIGS. 11 and 12). As with FIG. 10, each group of bars shown in FIGS. 11 and 12 includes one bar for each different time period provided by the legend, and time periods are organized in increasing order so that each bar from left to right corresponds to an increased time period (e.g., the left-most bar of each group represents a time period of 1 hour and the right-most bar of each group represents week 10). The excellent stability of these zwitterionic magnetofluorescent nanoparticles in these conditions especially in a solution with pH4, a solution with 1M salinity, and serum, is very attractive. Carboxybetaine groups and sulfobetaine groups coated on the surface of zwitterionic magnetofluorescent nanoparticles should be attributed to this stability. These zwitterions facilitate a hydration layer coating on zwitterionic magnetofluorescent nanoparticles, and the hydration layer is very stable and almost remains unperturbed under harsh conditions such as high/low pH values, high salinity, and complex matrix. The stability of zwitterionic magnetofluorescent nanoparticles offers a great deal of flexibility for their biomedical applications.

Figure 14:
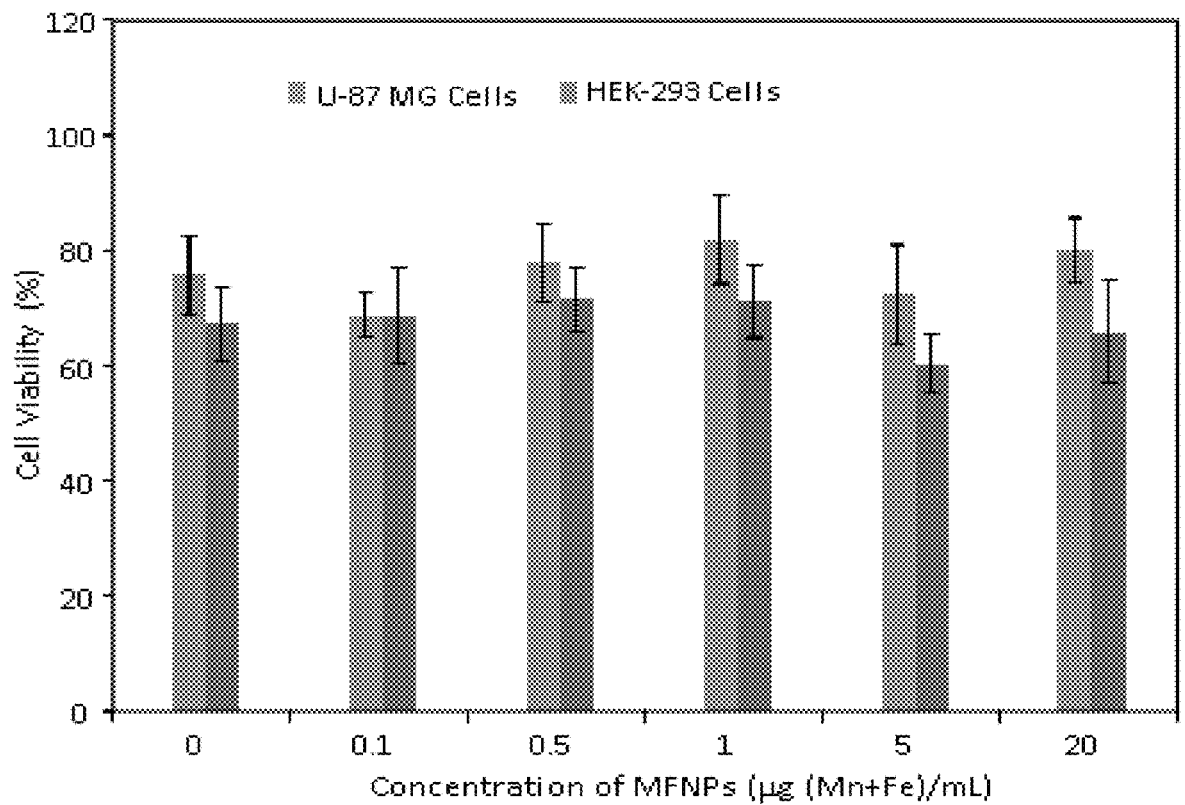
FIG. 14 is a graph illustrating cell viability of U-87 MG cell and HEK-293 cells treated with representative composites at difference concentrations over 24 hours.

The cytotoxicity of the zwitterionic magnetofluorescent nanoparticles was studied using human primary glioblastoma cells (U-87 MG) and human embryonic kidney 293 cells (HEK-293). U-87 MG and HEK-293 represent tumor cells and normal cells, respectively. FIGS. 13A and 13B show the measured cell viabilities for U-87 MG and HEK-293 after 24-hour incubation with zwitterionic magnetofluorescent nanoparticles under different concentrations, respectively. With reference to FIGS. 13A and 13B, each bar of the different bar groups represents a different MNP:quantum dot ratio, with each left-most bar representing an MNP:QD of 1:1, each middle bar representing an MNP:QD of 1:2, and each right-most bar representing an MNP:QD of 1:4. An additional embodiment is illustrated in FIG. 14. With reference to FIG. 14, the left-most bar of each bar group represents the data for U-87 MG cells, and the right-most bar of each bar group represents the data for HEK-293 cells. It can be seen that the cell viabilities under different particle concentrations are comparable to controls, and thus the zwitterionic magnetofluorescent nanoparticles are biocompatible and their cytotoxicity is minimal.

In one example, A U-87 MG human brain glioblastoma cell line was cultured (37° C., 5% $CO_2$) on 24-well plastic plates in MEM medium with 10% FBS overnight. The human embryonic kidney cell line HEK-293 was cultured (37° C., 5% $CO_2$) on 24-well plastic plates in RPMI-1640 medium with 10% FBS overnight. For the zwitterionic magnetofluorescent nanoparticle cytotoxicity examples, cells were incubated with zwitterionic magnetofluorescent nanoparticles in growth medium at various concentrations. After 24-hour incubation, cells were gently rinsed with DPBS and released from well bottom using stempro accutase, and then stained with FDA and PI to determine live versus dead cells. Dead cells (red staining by PI) and live cells (green staining by FDA) were counted using a BDBiosciences SORP LSR II flow cytometer. The cell viability was calculated as the ratio of live cells over the sum of live cells and dead cells.

Conjugation of Composites with Neutravidin for Avidin-Biotin Binding Assay

Figure 15:
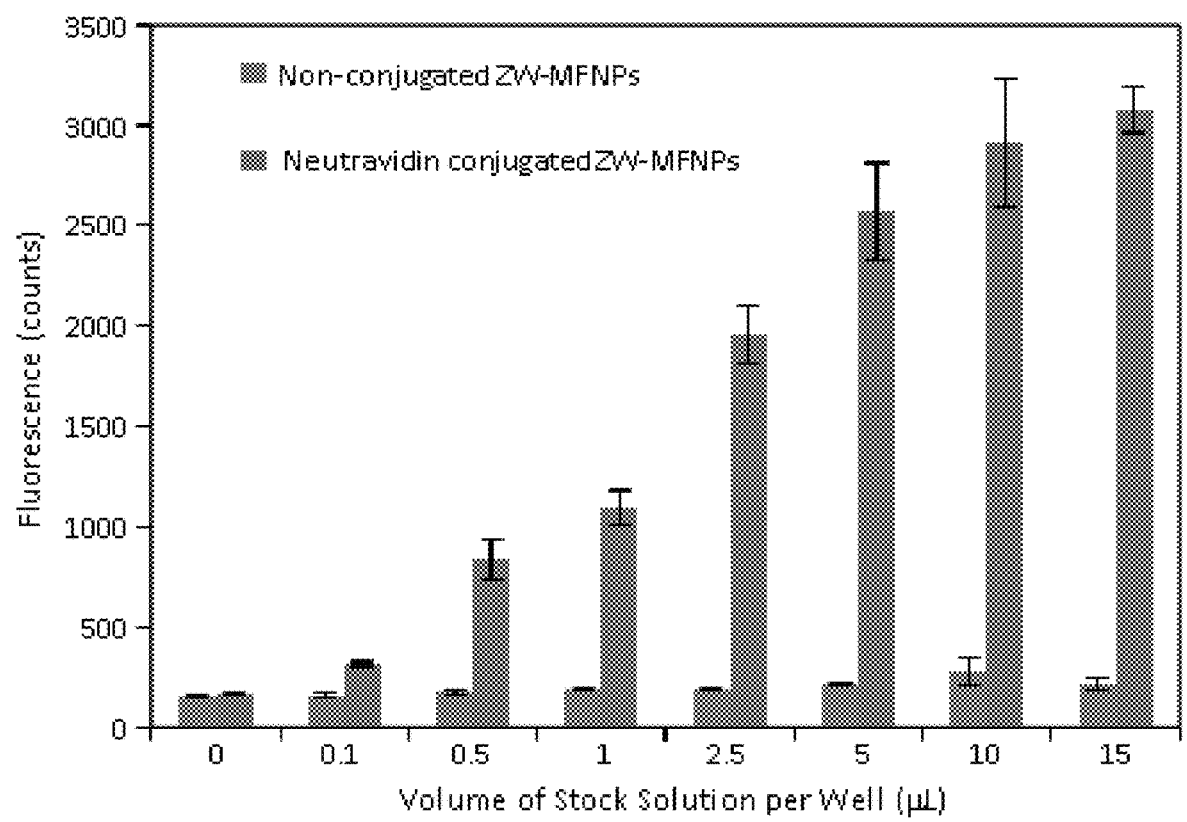
FIG. 15 is a bar graph illustrating the fluorescence responses to biotinylated magnetic microbeads after incubation with serial dilutions of non-conjugated and Neutravidin-conjugated composites from their stock suspensions.

To verify that zwitterionic magnetofluorescent nanoparticles are capable for bioconjugation, zwitterionic magnetofluorescent nanoparticles with a MNP:quantum dot mass ratio at 1:4 were fabricated and conjugated with Neutravidin using regular EDC/NHS cross-linker. The conjugated zwitterionic magnetofluorescent nanoparticles were then incubated with biotinylated magnetic microbeads (~4 µm in diameter). After incubation, microbeads were washed and their fluorescence was measured. FIG. 15 shows the fluorescence responses of the microbeads after their incubation with serial dilutions of Neutravidin-conjugated zwitterionic magnetofluorescent nanoparticles (FIG. 15, right-most bars of each bar group) from the stock suspension (or with different concentrations). As controls, the fluorescence responses of the biotinylated magnetic microbeads after their incubation with non-conjugated zwitterionic magnetofluorescent nanoparticles (FIG. 15, left-most bars of each bar group) under the same dilutions were measured. For each dilution or concentration, the fluorescence response for non-conjugated zwitterionic magnetofluorescent nanoparticles is clearly lower than that of conjugated zwitterionic magnetofluorescent nanoparticles. Thus, zwitterionic magnetofluorescent nanoparticles can be covalently conjugated with biomolecules. In addition, the assay result indicates that the nonspecific binding (NSB) of non-conjugated zwitterionic magnetofluorescent nanoparticles to microbeads is very low. The low NSB may be attributed to the nature of zwitterion (for example, the hydration layer of zwitterions makes zwitterionic magnetofluorescent nanoparticles more hydrophilic and minimizes the electrostatic or hydrophobic absorption of zwitterionic magnetofluorescent nanoparticles on the reaction surface).

In one example, zwitterionic magnetofluorescent nanoparticles with the MNP:quantum dot mass ratio at 1:4 were prepared and suspended in 200 µL $H_2O$. A 50-µL portion of the zwitterionic magnetofluorescent nanoparticles was mixed with 7.2 µg EDC (37.5 nmole in PBS pH 7.4), 8.1 µg sulfo-NHS (37.5 nmole in PBS pH 7.4), 13.6 µL Neutravidin (1.13 nmole in $H_2O$), and the total volume brought to 100 µL with PBS pH 7.4. The mixture was incubated for 2 hours at room temperature. After incubation, the magnetofluorescent nanoparticles were washed by centrifugation using PBS pH 7.4 (3×). The residue was dispersed in 200 µL PBS pH 7.4.

Three µL of biotinylated magnetic microbeads (4.5 µm diameter, 4×10⁸ beads/mL) were placed in each well of a microplate. Different volumes of the conjugate stock solution were loaded into wells, and PBS pH 7.4 buffer was used to bring the total volume in each well to 50 µL. The unconjugated zwitterionic quantum dot stock solution under the same dilutions was used as controls. The microplate was vortexed at room temperature for 1 hour, and then the magnetic microbeads in each well were washed using PBS pH 7.4 with 1% BSA and dispersed in 50 µL of PBS pH 7.4. The fluorescence signals of the suspended microbeads in wells were measured using a microplate reader at the excitation wavelength of 405 nm and the emission wavelength of 655 nm. The examples were performed in triplicates.

Figures 16A, 16B, 16C, 16D, 16E:
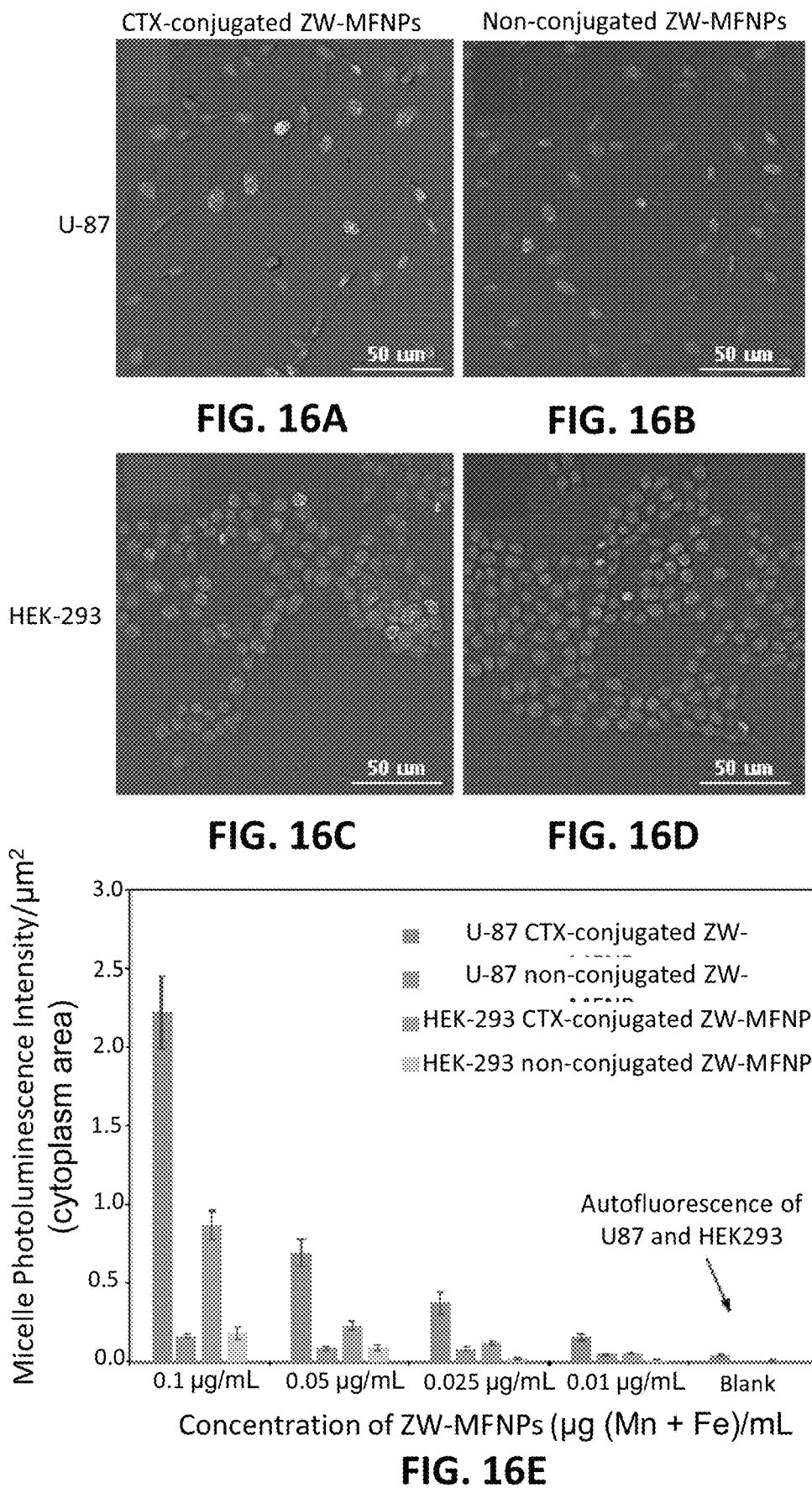
FIGS. 16A-16E illustrate results obtained for representative composites disclosed herein.
Figure 17A:
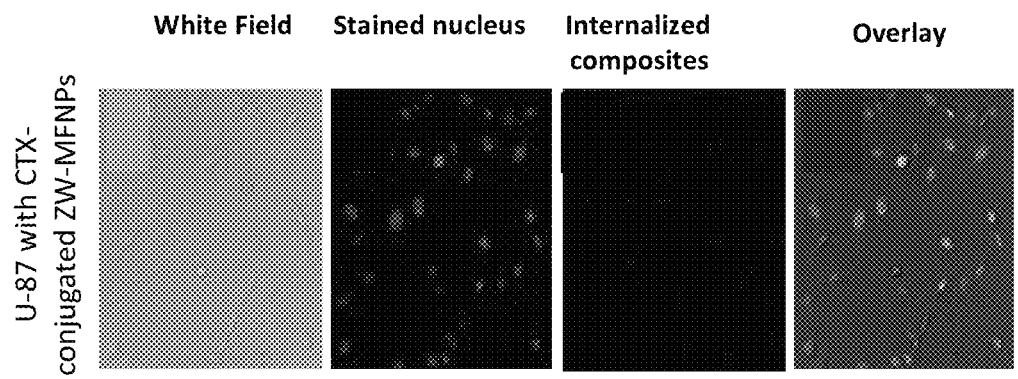
FIGS. 17A-17D are confocal images at different channels and their overlays demonstrating the cellular uptake/internalization of CTX-conjugated composites by U-87 (FIG. 17A) and HEK-293 (FIG. 17C) and non-conjugated composites under the same concentration of particles by U-87 (FIG. 17B) and HEK-293 (FIG. 17D).
Figure 17B:
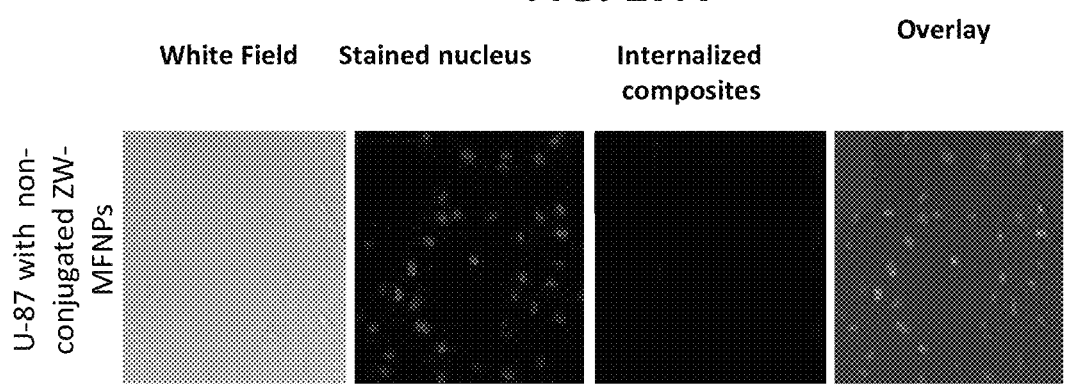
Figure 17C:
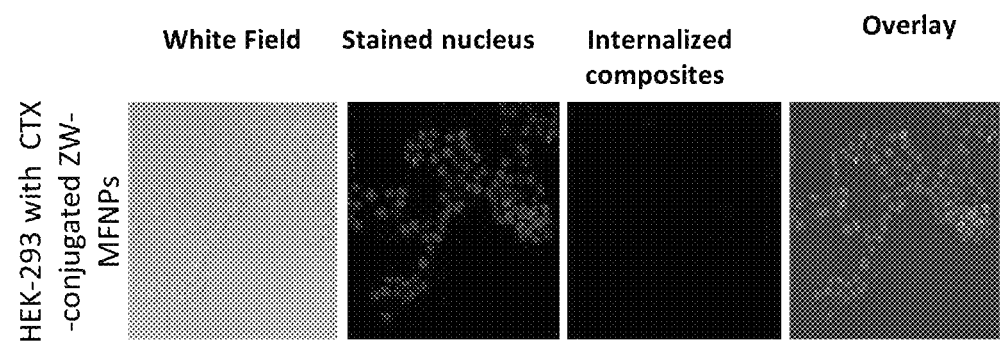
Figure 17D:
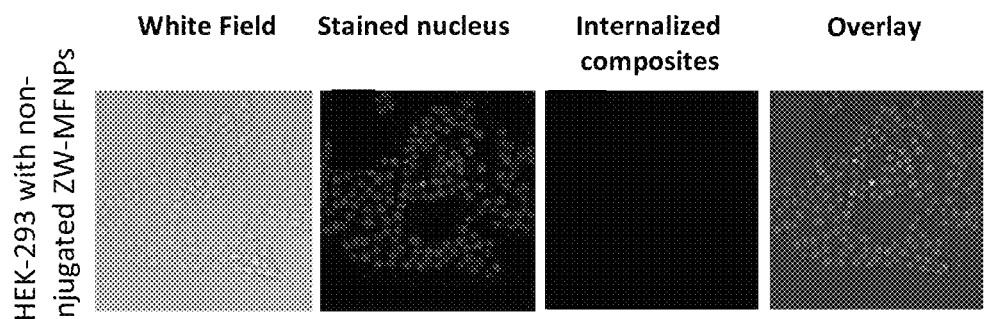

Tumor Cell Targeting Using Peptide Conjugated Zwitterionic Magnetofluorescent Nanoparticles For cellular imaging studies, CTX was used as a targeting ligand. CTX is a 36-amino acid peptide that specifically binds to matrix metalloproteinase II (MMP-2) present on the surface of glioma cells with high affinity. The specific binding results in loss of gelatinase activity, disruption in chloride channel currents, reduction in both MMP-2 and chloride channel expressions, and internalization of chloride channels. U-87 is a human primary glioblastoma cell line expressing MMP-2 receptors, and CTX can specifically bind to and be internalized into U-87. To investigate whether CTX-conjugated zwitterionic magnetofluorescent nanoparticles can be specifically targeted to and internalized into U-87, a nonmalignant cell line human embryonic kidney 293 (HEK-293) was used as a control. FIGS. 16A-16D present the representative overlaid confocal images demonstrating the cellular uptake/internalization when each type of cells were incubated with CTX- and non-conjugated zwitterionic magnetofluorescent nanoparticles under the same concentration of particles (i.e., 0.1 µg (Mn+Fe)/mL). Corresponding to each overlaid image in FIGS. 16A-16D, FIG. 17 shows the associated confocal images at different channels. FIG. 16E shows fluorescence intensity per unit cytoplasm area (counting>200 cells) under a series of zwitterionic magnetofluorescent nanoparticle concentrations. It can be seen that U-87 cells do internalize more CTX-conjugated zwitterionic magnetofluorescent nanoparticles than HEK-293, and non-conjugated zwitterionic magnetofluorescent nanoparticles produce no significant cellular uptake by both cell lines. Through this comparison, it can be concluded that CTX-conjugated zwitterionic magnetofluorescent nanoparticles are specific to U-87. It was also observed that HEK-293 did internalize some CTX-conjugated zwitterionic magnetofluorescent nanoparticles at high concentrations. It is believed that the cellular uptake of CTX-conjugated micelles may involve pinocytosis mechanisms in high concentration ranges.

In one example, zwitterionic magnetofluorescent nanoparticles were conjugated with CTX via EDC/sulfo-NHS mediated reaction. Briefly, 60 µL of the collected zwitterionic magnetofluorescent nanoparticles were reacted with 50 µg CTX with the assistance of EDC/sulfo-NHS in PBS for 2~3 hours. The CTX-conjugated zwitterionic magnetofluorescent nanoparticles were washed using centrifuge, suspended in 250 µL PBS, and stored at 4° C. before use. A U-87 MG human brain glioblastoma cell line was cultured (37° C., 5% $CO_2$) on glass coverslip coated with gelatin in MEM medium with 10% FBS until 50-80% confluency was achieved. The human embryonic kidney cell line HEK-293 was cultured (37° C., 5% $CO_2$) on glass coverslip coated with PDL (poly-D-lysine) in RPMI-1640 medium with 10% FBS until 50~80% confluency was achieved. For the zwitterionic magnetofluorescent nanoparticle tumor cell targeting examples, cells were incubated with CTX conjugated zwitterionic magnetofluorescent nanoparticle in DMEM with 2% BSA at various concentrations. As control, cells were also incubated with non-conjugated zwitterionic magnetofluorescent nanoparticles. After 2 hours of incubation, cells were gently rinsed three times with PBS, fixed with 4% PFA in PBS solution for 20 minutes and washed three times with PBS. For cellular nuclei staining, cells were incubated with DAPI, washed three times with PBS, and then mounted on glass slides. Cells were imaged using a Leica confocal microscope and images were analyzed using ImageJ. The statistical significance (p<0.05) was determined by the single-tailed student t test.

Methods of Making Quantum Dots Using Thermal Decomposition

Silver Acetate (99%), Indium (III) Acetate (99.99%), Zinc Stearate (ZnO: 12.5-14%), and Paraformaldehyde (97%) were purchased from Alfa Aesar. Sulfur (>99.99%), Trioctylphosphine (TOP, 90%), 1-Dodecanethiol (98%), 1-Octadecene (ODE, 90%), Oleic Acid (99%), Methanol (99.93%), and 1,10-Phenanthroline (99%) were purchased from Sigma Aldrich. Tetrahydrofuran (THF, >99%), Ethanol (>99%), Chloroform (>99.9%), and Hexane (95%) were purchased from Pharmco-AAPER. Methoxy poly(ethylene glycol)-b-poly(lactide-co-glycolide) (PEG-PLGA) (MW~5000:5000 Da) and maleimide-PEG-PLGA (MW~5000:5000 Da) were purchased from Akina, Inc. Dulbecco's Phosphate Buffered Saline (DPBS), Phosphate Buffered Saline (PBS), Ethylenediaminetetraacetic Acid (EDTA), Acetonitrile (99.96%) and Traut's Reagent were from Fisher Scientific. Heat-inactivated Fetal Bovine Serum (FBS) was from Gibco. U-87 MG and HEK-293 cells were ordered from the American Type Culture Collection (ATCC). RPMI-1640, MEM and DEMEM media were from Corning Cellgro. 7-Aminoactinomycin D dye (7-AAD, excitation at 488 nm and emission at 647 nm) for cell nucleic acid staining was from Invitrogen. Chlorotoxin (CTX) was purchased from Alomone Labs. Bovine Serum Albumin (BSA) was from MP Biomedicals. Zeba spin desalting columns (MWCO 7k) were from Pierces.

The ultraviolet and visible (UV-Vis) spectra of materials were obtained with a UV-Vis spectrometer (UV-2450 from Shimadzu). Photoluminescence spectra of quantum dots in organic-phase and aqueous-phase were acquired using a spectrophotometer (RF-5301PC from Shimadzu) Photoluminescence intensity of quantum dots in various buffers was obtained using a microplate reader (PerkinElmer 2030 equipped with a 535 nm emission filter and a 405 nm excitation filter). Transmission electron microscope (TEM) images and Energy-dispersive X-ray (EDX) spectra were acquired using a JEOL analytical transmission electron microscope (model JEM 2100F operated with a 200 kV acceleration voltage) equipped with an Oxford Energy-Dispersive X-ray (EDX) spectrometer. X-ray Diffraction (XRD) data was collected by a coupled Theta:2-Theta scan on a Rigaku Ultima-III diffractometer equipped with Copper X-ray tube with Ni beta filter, parafocusing optics, computer-controlled slits, and D/Tex Ultra 1D strip detector. The hydrodynamic sizes of micelles were measured using a dynamic light scattering (DLS) instrument (Malvern Zetasizer Nano ZS) equipped with a HeNe laser operating at 632.8 nm and a scattering detector at 173 degrees. Probe sonication was performed with a Misonix ultrasonic processor (QSonica S-4000) equipped with a microtip. Infrared (IR) spectra of materials were collected using a Fourier transform infrared (FT-IR) spectrometer (Perkin-Elmer Frontier) with Spectrum 10 software and the Universal ATR Sampling Accessory. Cells were imaged using a Leica confocal microscope and images were analyzed using ImageJ.

Quantum yields of quantum dots were calculated according to the following equation, using standard references including Rhodamine 6G (emission peak at 556 nm, QY=95% in ethanol) and Oxazine 170 (emission peak at 640 nm, QY=63% in methanol), $$QY_S = QY_R \times (I_S/I_R) \times (A_R/A_S) \times (n_S/n_R)^2$$

where $QY_S$ and $QY_R$ are the quantum yields of sample and a standard reference, respectively; $I_S$ and $I_R$ are the integrations of fluorescence emissions of sample and a standard reference, respectively; $A_S$ and $A_R$ are the corresponding absorbance of sample and a standard reference, respectively; and $n_S$ and $n_R$ are the refractive indices of the corresponding solvents.

During quantum yield measurements, the absorbance of each sample or each standard reference deviated by less than 0.1. For each sample, the standard reference with the most similar absorption and/or luminescence characteristics was chosen for quantum yield measurements.

AIS/ZnS Quantum Dot Synthesis

For a typical synthetic reaction, silver acetate (0.1 mmol), Indium (III) acetate (0.2 mmol), DDT (4 mL) and oleic acid (0.2 mmol, 63.5 µL) were added in a three-necked round bottom flask equipped with a condenser and magnetic stir bar. This mixture was degassed under vacuum for 20 minutes at 130° C. until the solution became clear. The solution temperature was then increased to 170° C. under a flow of Argon. As the temperature was increased, the color of the reaction solution changed gradually from yellow to orange, indicating the nucleation and growth of AIS quantum dots. Small amounts of the reaction solution (0.1-0.2 mL) were collected using a syringe at different time intervals and injected into hexane in clean vials to terminate growth of quantum dots. All solutions collected from the studies were diluted in a quartz cuvette with hexane for UV-Vis absorbance and photoluminescence measurements. After the reaction was complete, the solution was cooled to room temperature. The crude quantum dots solution was purified repeatedly with the solvent combinations of hexane/ethanol and chloroform/acetone by centrifugation and dried under vacuum.

For ZnS shell growth, the Zn precursor was prepared by mixing zinc stearate (1.6 mmol) and ODE (4 mL) in a round-bottom flask. The mixture was gradually heated to ~100° C. with stirring under vacuum until no vigorous bubbling was observed. The temperature was increased to 160° C. under argon until a clear solution was obtained. The sulfur precursor was prepared by dissolving sulfur (1.6 mmol) in DDT (3.2 mL) and TOP (0.8 mL). The ZnS shell coating of AIS quantum dots was carried out in situ without purification of the core. 4 mL ODE was added to the crude AIS solution. This core solution was degassed under vacuum at 130° C. for 30 min and then to 210° C. under Argon. Both zinc and sulfur precursors were injected in sequence 5 times to the core growth solution at 210° C. in 0.5 mL portions at 15 min intervals. After reactions were complete, mixtures were cooled down to room temperature and AIS/ZnS quantum dots were purified using hexane/ethanol and chloroform/acetone, and dried under vacuum. It is possible to collect around 40 mg AIS quantum dots and around 100 mg AIS/ZnS quantum dots per reaction.

Figure 18:
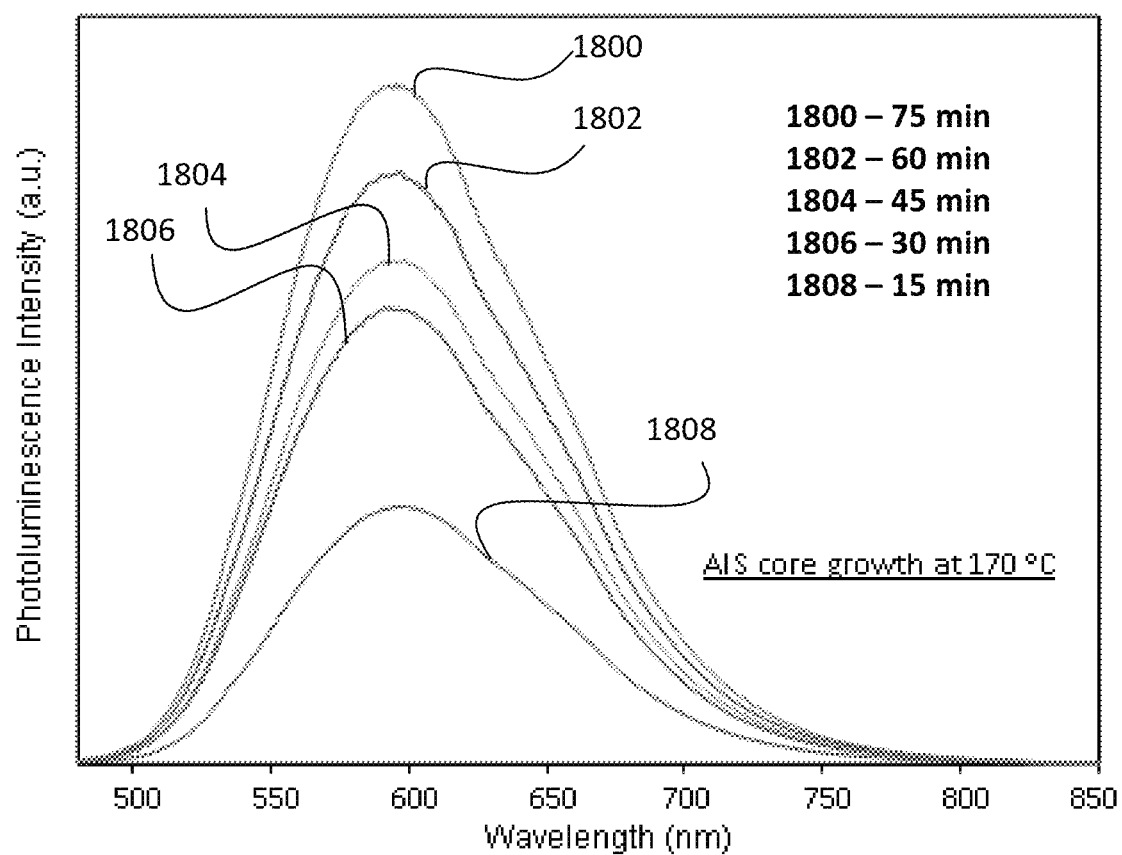
FIG. 18 illustrates the evolution of the photoluminescence spectra of a representative quantum dot used in composites described herein during the time course of growth at 170° C.

FIG. 18 shows photoluminescence spectra of AIS quantum dots during the time course of growth at 170° C. It can be seen that the quantum yield of AIS quantum dots is enhanced during growth reaching 13% at 75 min. The quantum yield enhancement over time is likely caused by a reduction of quantum dot core defects during heat treatment. Nevertheless, the photoluminescence spectral shift is not significant or sensitive to growth time. This optical characteristic suggests that AIS growth is very slow. The slow growth of AIS quantum dots is probably due to the relatively mild reaction temperature. When using a higher reaction temperature (230° C.), typically for CIS quantum dots, it was found that the products of the AIS synthetic system are hard to solubilize in chloroform and hexane, and thus hard to characterize optically.

Characterization of Quantum Dots

Figure 19A:
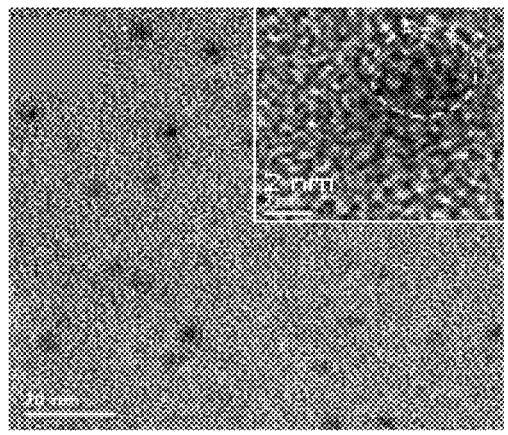
FIGS. 19A-19C are images illustrating results obtained from TEM and EDX analysis of representative quantum dots made using methods described herein.
Figure 19B:
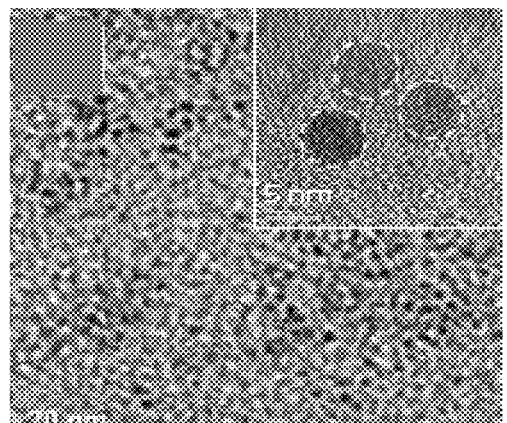
Figure 19C:
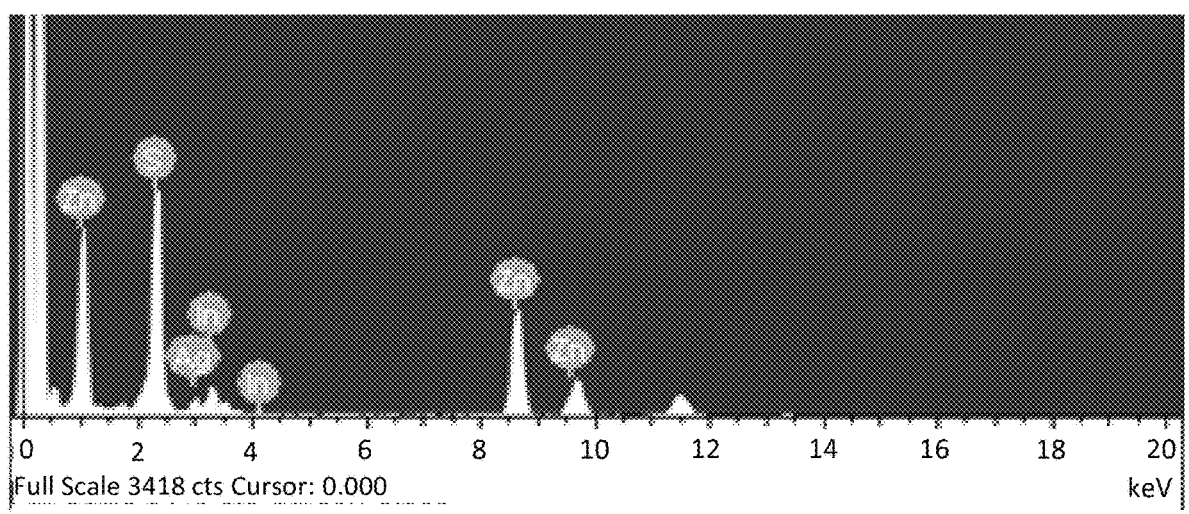
Figure 20:
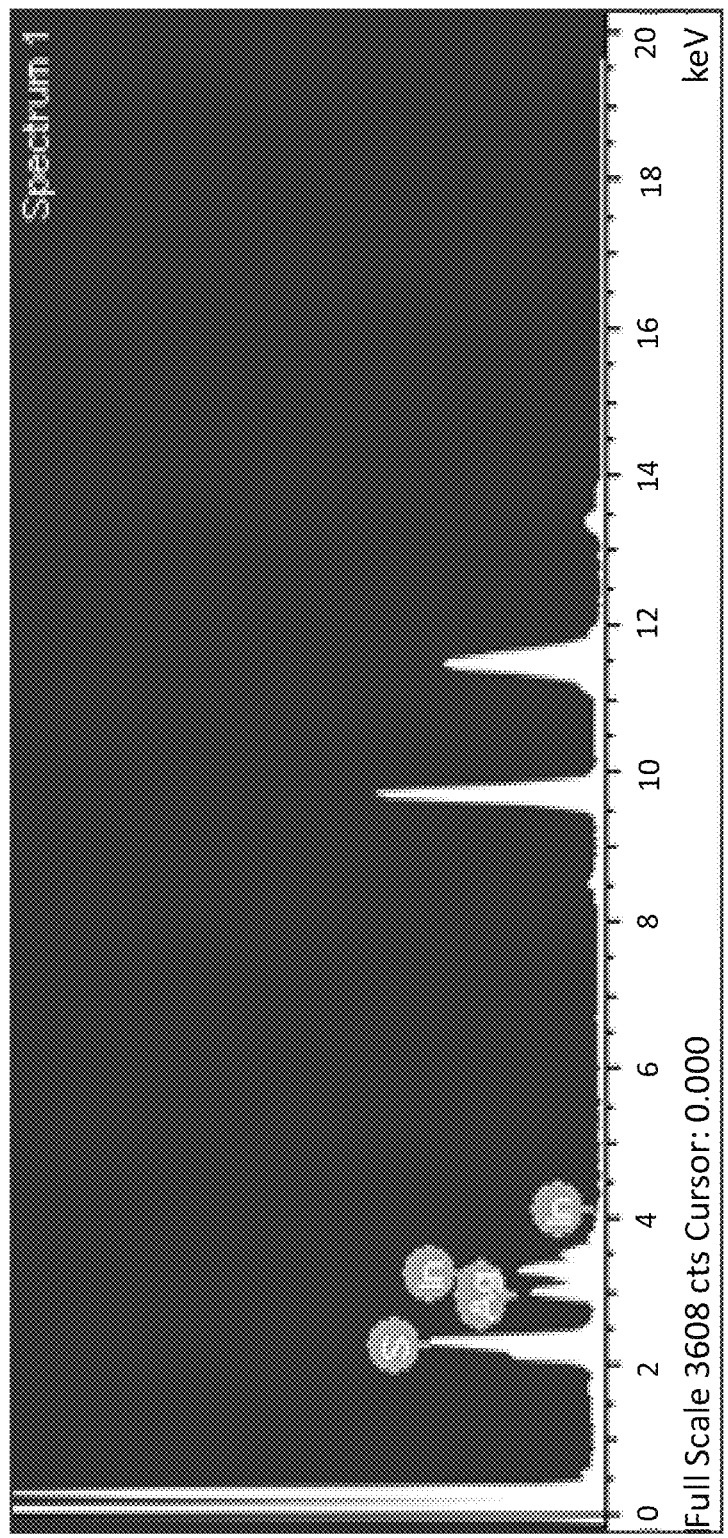
FIG. 20 is an EDX spectrum of a representative quantum dot made using a thermal decomposition synthesis embodiment.
Figure 34A:
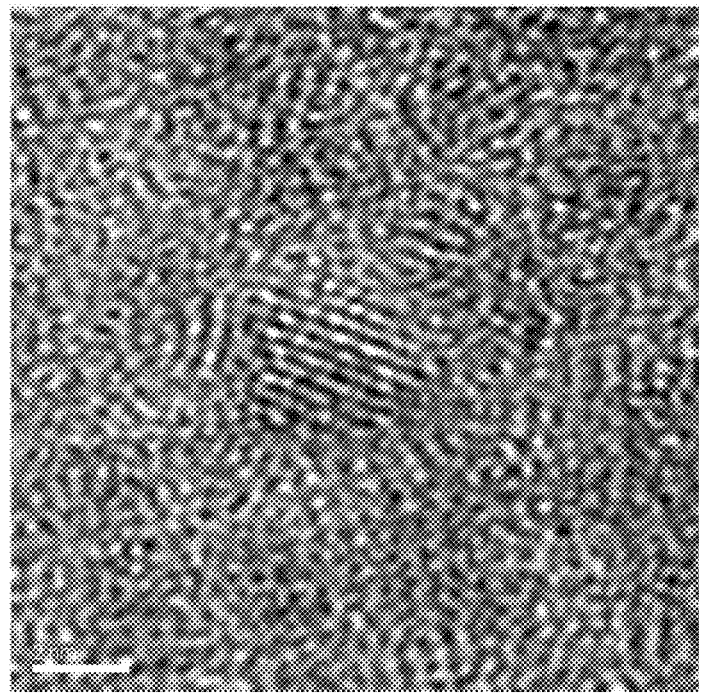
FIGS. 34A and 34B each are TEM images of a representative quantum dot made using a disclosed thermal decomposition method embodiment.
Figure 34B:
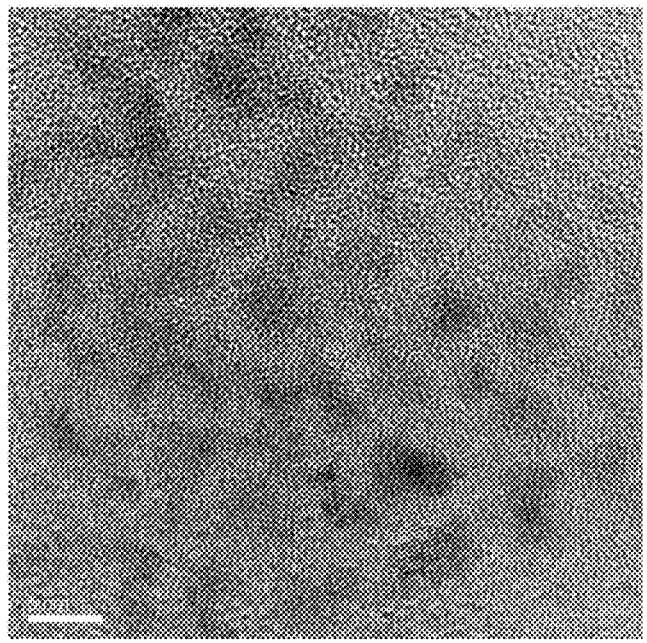

AIS quantum dots and AIS/ZnS quantum dots were further characterized using TEM. FIGS. 19A and 19B present TEM and high resolution TEM (HRTEM) images of AIS and AIS/ZnS quantum dots, respectively. TEM images of CIS quantum dots made using thermal decomposition method embodiments disclosed herein are shown in FIG. 34A (normal resolution) and 34B (high resolution). The HRTEM images reveal crystalline patterns and sizes (~4.5 nm for AIS and ~6 nm for AIS/ZnS) of both quantum dots, indicating that the synthesized particles to be nanocrystals. Energy-dispersive X-ray (EDX) spectra confirm that AIS/ZnS quantum dots are composed of Ag, In, Zn, and S (FIG. 19C) and AIS quantum dots are composed of Ag, In and S (FIG. 20). More specifically, Table 1 shows the elemental atomic ratios of AIS and AIS/ZnS quantum dots. For AIS quantum dots, the atomic ratio between Ag and In is close to 1:1 with the atomic percentage of In slightly higher. For AIS/ZnS quantum dots, the atomic percentages of Ag and In drop off but the Ag percentage is reduced to a greater extent, and the atomic percentages of Zn and S are increased. The significant reduction of Ag atomic percentage in AIS/ZnS is probably due to Zn etching to replace Ag during the ZnS shell growth. It is generally agreed that cation exchange between Zn ions (from Zn precursor) with Ag (or Cu) in AIS (or CIS) causes photoluminescence blue shift and quantum yield enhancement. As shown in FIG. 1, both effects were observed after growing ZnS shell on AIS cores. EDX analysis demonstrates a good match of the observed photoluminescence blue shift and quantum dot brightness enhancement of AIS/ZnS quantum dots compared to AIS quantum dots.

Figure 21:
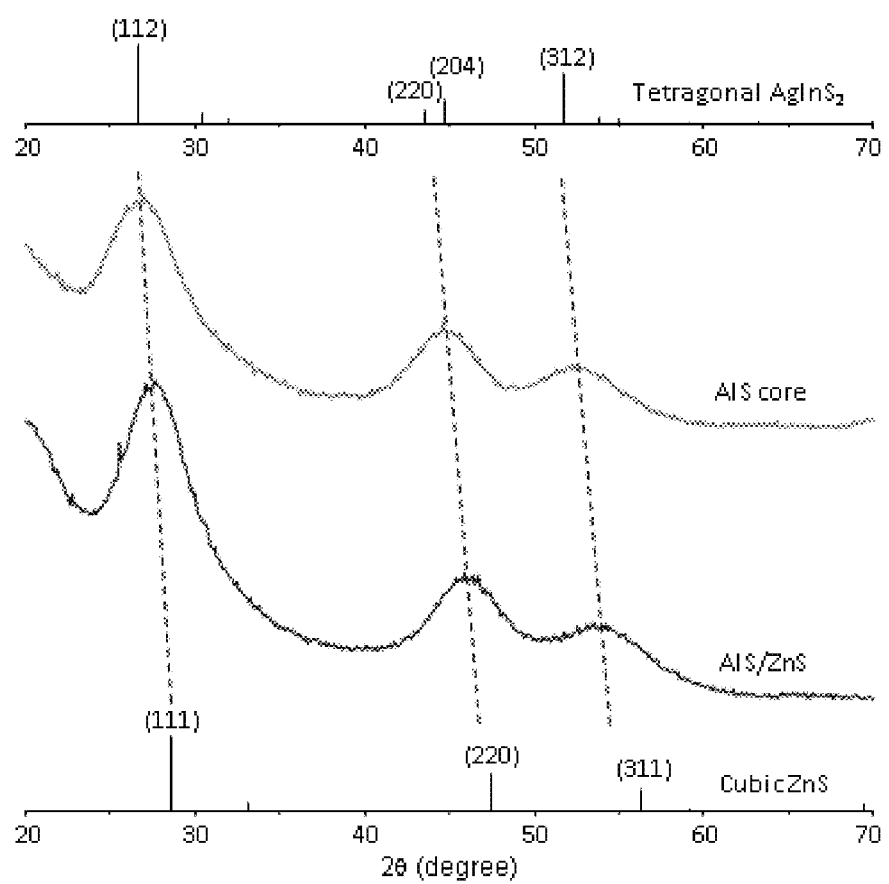
FIG. 21 illustrates XRD patterns for representative shell-coated and shell-free quantum dots; diffraction peaks of tetragonal $AgInS_2$ and cubic ZnS are shown as references.

The crystal phase of the AIS and AIS/ZnS quantum dots was examined by X-ray powder diffraction (XRD), as shown in FIG. 21. The XRD pattern of AIS quantum dots shows three broad peaks at 2θ=26.8°, 44.6° and 52.2°, which can be assigned respectively to the diffractions of the (112), (204) and (312) planes of the tetragonal $AgInS_2$. No other phases or impurities were observed. The AIS/ZnS quantum dots diffraction pattern shows a similar profile to that of the AIS quantum dots with three right-shifted peaks at 2θ of 27.7°, 46.0° and 54.0°. These peaks can be seen at positions intermediate between the diffractions of (112), (204), and (312) planes of tetragonal $AgInS_2$ and the diffractions of (111), (220), and (311) planes of cubic ZnS, suggesting that Zn atoms were deposited on or diffused into the surface of the AIS cores.

Figure 22:
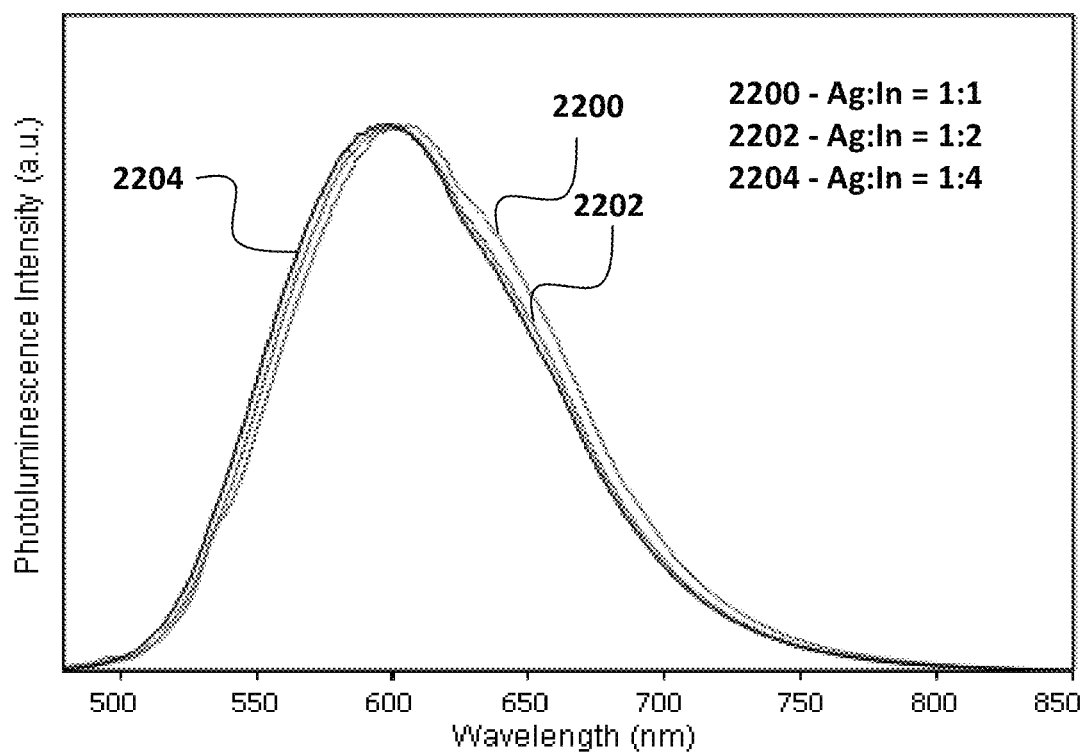
FIG. 22 illustrates photoluminescence spectra of representative quantum dots made using a disclosed thermal decomposition method embodiment.
Figure 23:
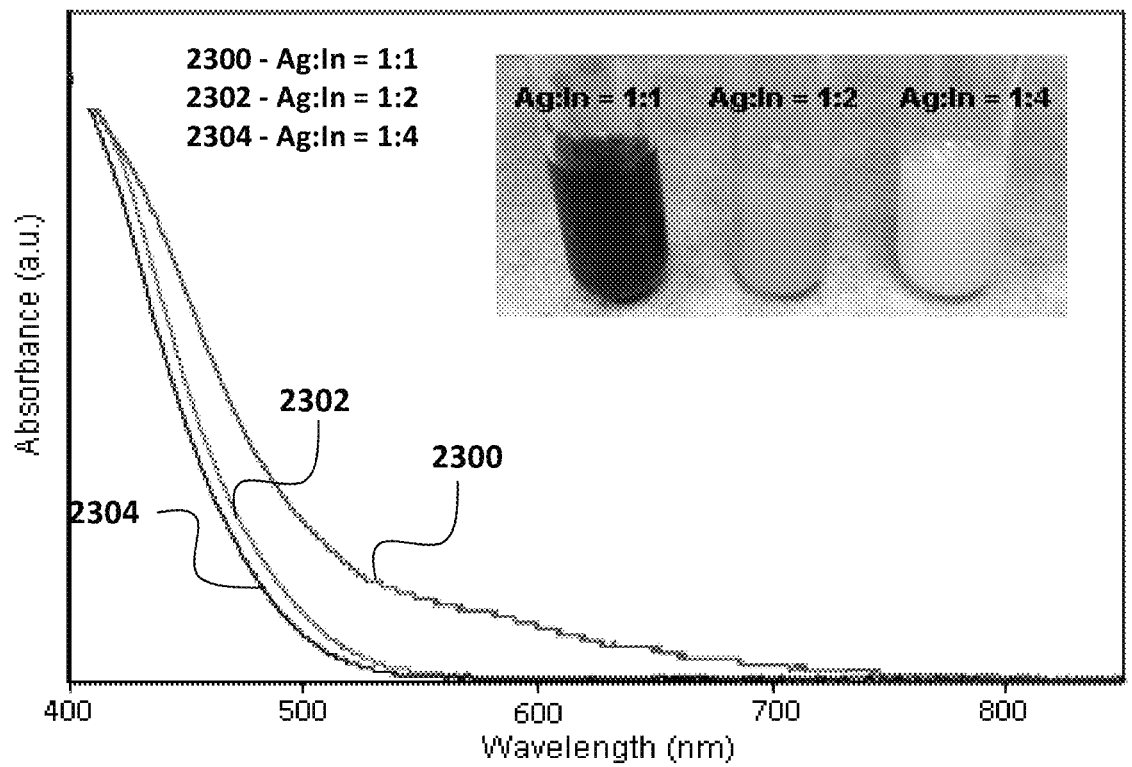
FIG. 23 illustrates UV-Vis absorption spectra representative quantum dots synthesized at different ratios (1:1, 1:2 and 1:4), wherein the inset provides digital photograph of the quantum dots under room lights.
Figure 24A:
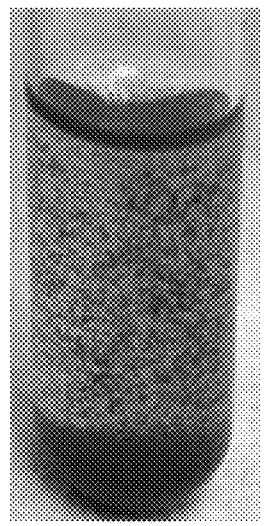
FIGS. 24A and 24B are digital photographs of representative quantum dots made using a disclosed thermal decomposition method embodiment.
Figure 24B:
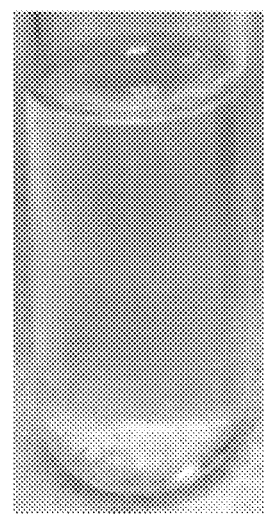

It should be noted that all characterized materials MS and AIS/ZnS quantum dots were synthesized with an original Ag:In precursor molar ratio of 1:2. This ratio can be used to avoid possible side products or black precipitates in reactions. AIS quantum dots were synthesized at different Ag:In precursor molar ratios (Ag:In=1:1, 1:2, and 1:4) without changing other conditions. The collected AIS samples were diluted in hexane and their photoluminescence and UV-Vis absorbance spectra were measured. As shown in FIG. 22, all samples have similar photoluminescence spectra without obvious shifts. However, as illustrated in FIG. 23, AIS quantum dots synthesized with Ag:In=1:1 have a wider absorbance wavelength range than the other two samples. Moreover, the AIS quantum dot solution (Ag:In=1:1) is a dark brown color, as illustrated in the inset of FIG. 23. This suggests that there is something else (possibly $Ag_2S$) produced during the reaction with Ag:In=1:1 at 170° C. but particles are not large enough to precipitate. The AIS quantum dot solution (Ag:In=1:1) was further used to grow the ZnS shell on AIS quantum dots and as shown in FIG. 24A, the resultant product includes both a green solution and black precipitates. However, after the ZnS shell growth of AIS quantum dots (Ag:In=1:2), the resultants are clear (FIG. 24B). These observations lead to the molar ratio of Ag:In=1:2 used in the synthesis. AIS synthesis using Ag:In=1:4 was not performed, because this ratio does not significantly shift quantum dot photoluminescence and excess In precursors in the reaction increase synthesis cost.

Figure 25A:
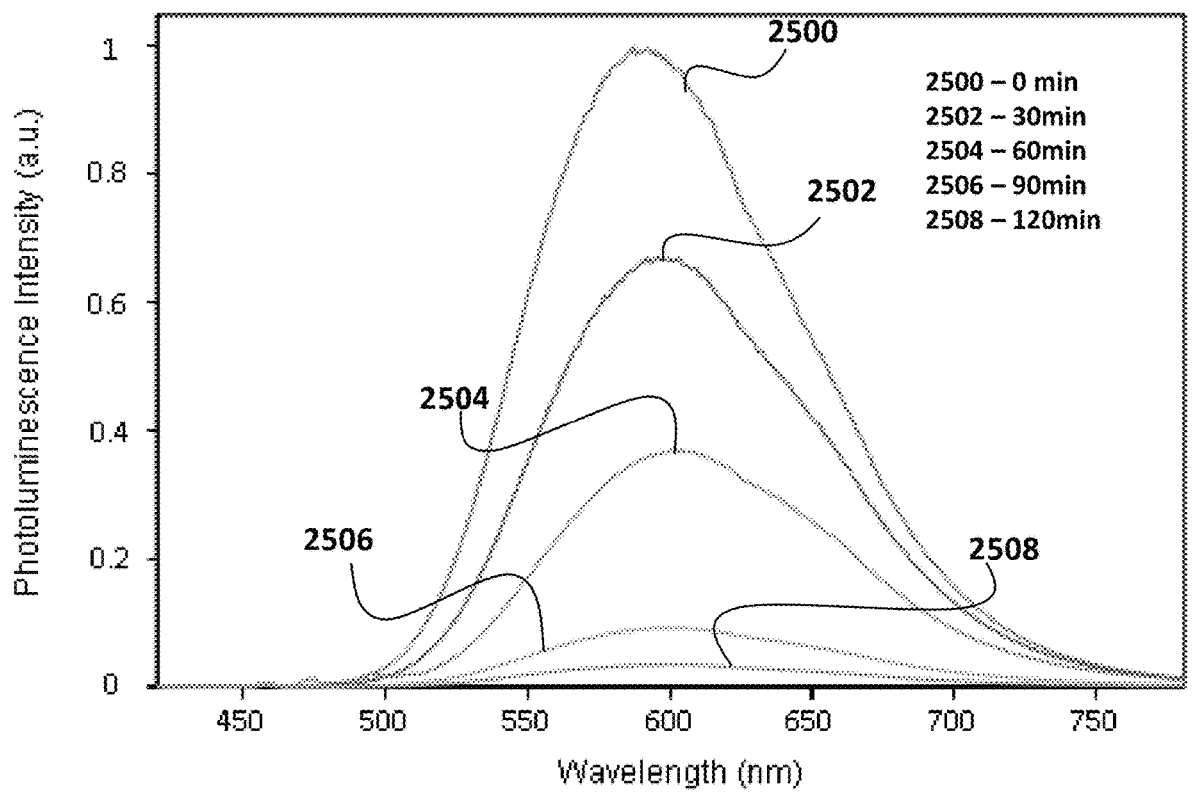
FIGS. 25A and 25B are graphs illustrating the photostability of AIS quantum dots (FIG. 25A) and AIS/ZnS quantum dots (FIG. 25B), wherein quantum dots in organic solvents were under continuous exposure of a 365 nm UV lamp for 120 minutes and their photoluminescence was measured every 30 minutes.
Figure 25B:
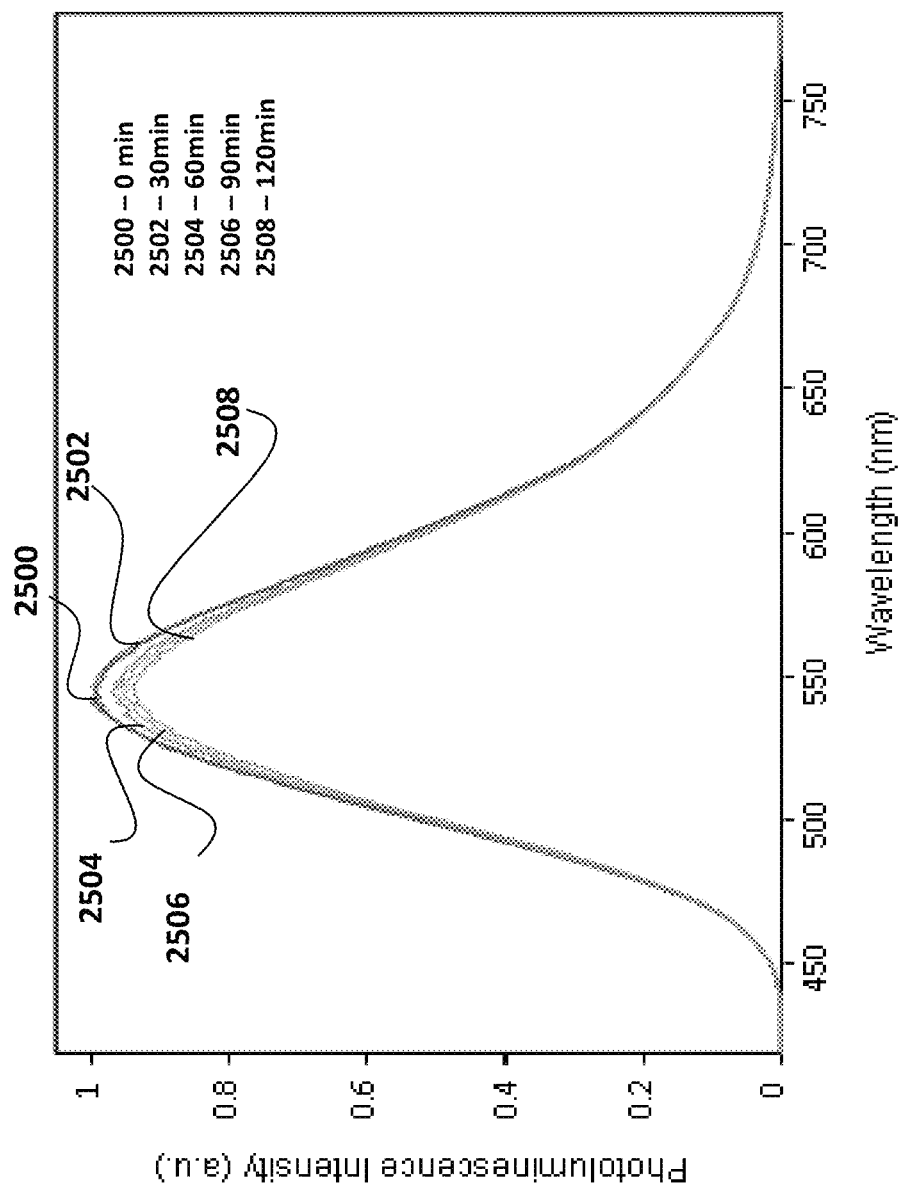

In the proposed thermal decomposition approach, indium acetate and silver acetate could initially react with DDT to form intermediate compounds of $Ag(SC_{12}H_{25})_x$ and $In(SC_{12}H_{25})_x$ upon heating and are dissolved in DDT. As the reaction temperature is raised to 170° C., the intermediate compounds could act as precursors and further are decomposed into Ag—S and In—S to form Ag—In—S particles. Considering that there are some unexpected materials produced in the reaction with a molar ratio of Ag:In at 1:1, it is possible that $Ag(SC_{12}H_{25})_x$ compounds are decomposed faster than $In(SC_{12}H_{25})_x$ compounds and thus Ag—S are excess to form dark $Ag_2S$ particles. This could explain why 1:2 molar ratio of Ag:In is good for the reaction. Of note, the photostability of the produced AIS and AIS/ZnS quantum dots were tested and presented in FIGS. 25A and 25B. It can be seen that AIS/ZnS quantum dots remain their photostability but AIS quantum dots are significantly photobleached. The photobleaching of AIS quantum dots could be caused by complex UV-induced chemical reactions at the interface between AIS and organic solvents. For example, electrons excited from AIS react with organic solvents to form free radicals which could further etch the AIS surface and quench the AIS photoluminescence. The photostability of AIS/ZnS quantum dots is believed to benefit from the protection of AIS core by its ZnS shell.

Figure 26:
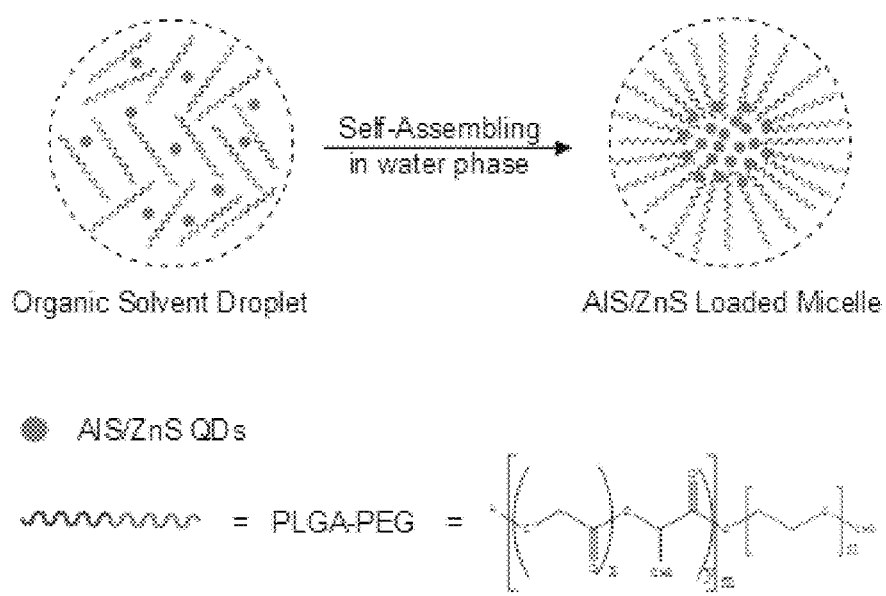
FIG. 26 is a schematic illustration of quantum dot-loaded micelles comprising quantum dots made using thermal decomposition method embodiments disclosed herein.
Figure 27:
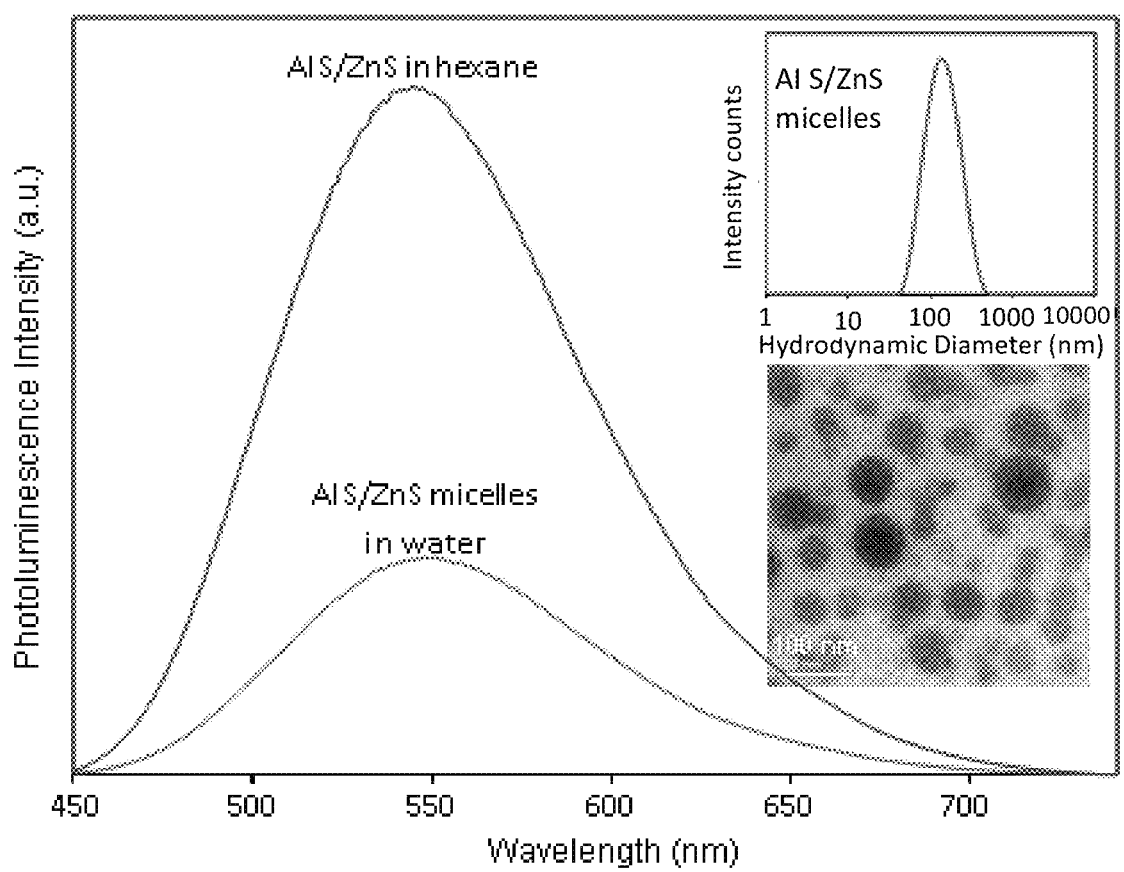
FIG. 27 illustrates photoluminescence spectra of representative quantum dots in hexane and quantum dot micelles in water, wherein the insets are the hydrodynamic size distribution of the resulting quantum dot-micelles measured by DSL (top) and the corresponding TEM image of the quantum dot-micelles.
Figure 28A:
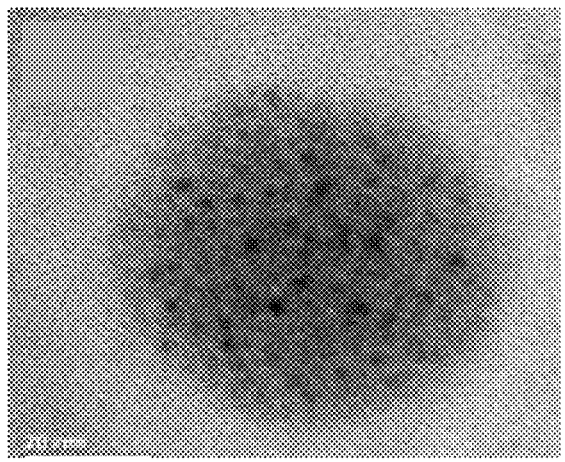
FIGS. 28A-28C are TEM and EDX images obtained for representative quantum dots.
Figure 28B:
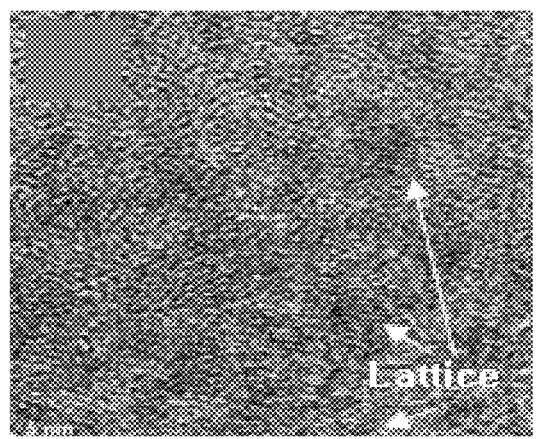
Figure 28C:
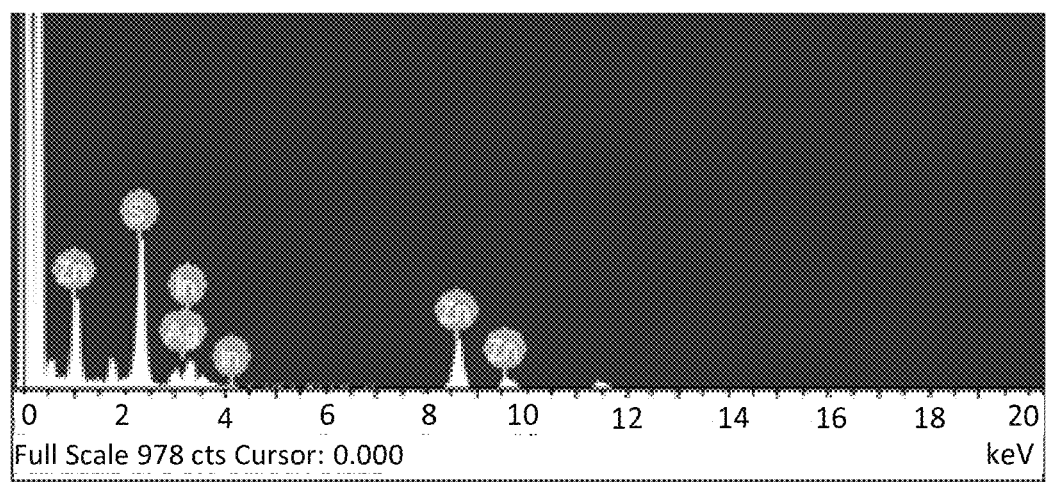

To demonstrate potential biomedical applications of the produced AIS/ZnS quantum dots, these quantum dots were loaded into the core of PLGA-PEG based micelles to form quantum dot-micelles. The quantum dot-micelle preparation is schematically illustrated in FIG. 26. Briefly, AIS/ZnS quantum dots were mixed with amphiphilic polymers of PLGA-PEG in organic solvents, and then dispersed them into water with sonication. During the vacuuming or water-replacement of organic solvents, the hydrophobic portion (PLGA) of the polymers and quantum dots are self-associated into a semi-solid core, and the hydrophilic portion (PEG) of the polymers forms a coronal layer. Photoluminescence spectra of AIS/ZnS quantum dots before and after water transfer via micelles were measured and are shown in FIG. 27. It can be seen that the quantum dot-micelles show a slight red-shift in photoluminescence spectra and remain around 30% quantum yield compared to quantum dots suspended in organic solvents. The red-shift and the quantum yield drop after the phase transfer is believed to be caused by a compact quantum dot cluster in micelle cores. In the compact cluster, the emission photons from smaller quantum dots are absorbed by larger quantum dots to emit at longer wavelengths (a Förster resonance energy transfer process). Moreover, the cluster reduces the total excitation and emission surface area of quantum dots, resulting in a quantum yield drop. In spite of quenching, the quantum dot-micelles are still adequate for optical imaging applications. The insets of FIG. 27 show the hydrodynamic sizes (126 nm±53 nm) of the quantum dot-loaded micelles measured by DLS and the TEM image of quantum dot-micelles, respectively. FIGS. 28A and 28B show the TEM image and high resolution TEM image of an individual micelle. It can be seen that some dots are presented in a single micelle, and with further zooming into the micelle crystal lattices of dots are observed. Further EDS analysis on micelles (FIG. 28C) shows that silver, indium, zinc and sulfur elements are presented in micelles, which are the composites of AIS/ZnS quantum dots.

Preparation of AIS/ZnS Micelles

The solution of 2.4 mg AIS/ZnS quantum dots and 9.6 mg PEG-PLGA (50% PEG-PLGA and 50% maleimide-PEG-PLGA) in THF/acetonitrile was layered on the top of cold water in a glass vial. The mixture was ultrasonicated using the Misonix Ultrasonic Liquid Processor with a 3 W output power for 1 minute. After sonication, THF/acetonitrile was removed by rotary evaporation at room temperature and the sample filtered through a 0.2 µm syringe filter to remove large aggregates. Empty micelles or single-nanoparticle based micelles were removed by centrifugation at 18,000 rpm for 15 minutes. The collected micelles were then re-filtered through a 0.2 µm syringe filter, concentrated using a centrifugal filter, dispersed in 400 µL of water, and stored at 4° C. until further use.

Cell Culture, Cellular Uptake/Internalization of AIS/ZnS Micelles, and Cellular Imaging A U-87 MG human brain glioblastoma cell line (ATCC HTB-14) was maintained in Minimum Essential Media (MEM, Corning Cellgro) supplemented with 10% FBS at 37° C. and 5% $CO_2$. The human embryonic kidney cell line HEK-293 (ATCC CRL-1537) was maintained in RPMI-1640 medium (Corning Cellgro) supplemented with 10% FBS at 37° C. and 5% $CO_2$.

For the quantum dot-micelle cellular uptake assay, U-87 and HEK-293 cells were plated on 24-well plastic plates and allowed to propagate for 2-3 days until they reached 50-80% confluency. The cells were incubated with CTX-conjugated or non-conjugated AIS/ZnS quantum dot-micelles in cell culture medium with 2% BSA for 2 hours at 37° C. After incubation, the solution was removed and the cells were washed three times with cold PBS buffer (pH 7.4). Then cells were fixed with 4% paraformaldehyde in PBS at room temperature for 20 minutes, followed by cell nucleus staining with 7-Aminoactinomycin D (7-AAD) for 45 minutes. The cells were examined by a laser scanning confocal microscope (LSCM, Leica, TCS SP8, Germany). The statistical significance ($p<0.05$) was determined by the single-tailed student t test.

To demonstrate potential biomedical or biological applications of AIS/ZnS quantum dots, these quantum dots were loaded into the core of PLGA-PEG (5 kDa:5 kDa) based micelles to form the AIS/ZnS quantum dot-micelles and further investigated their specific-targeting functionality as cellular imaging probes or contrasts. With functional groups such as maleimide on PEG heads, the quantum dot-micelles were conjugated with chlorotoxin (CTX), a ligand that specifically binds to U-87 brain tumor cells. Cellular imaging studies showed that the quantum dot-micelles conjugated with CTX are specifically internalized into the brain tumor cells. Since the hydrophobic core of micelles can be loaded with both drugs and image contrasts, the specific cellular internalization suggests that the quantum dot-micelle structures could be important and versatile nanoplatforms for cell- or tissue-based diagnosis and therapy. Moreover, loading multiple quantum dots in the hydrophobic cores could avoid the blinking effect of single quantum dot and therefore facilitate continuous image tracking. Notably, the common surface modification approaches using thiolated ligands to exchange hydrophobic ligands capped on quantum dots (CdSe or CdS) are less favorable for AIS/ZnS quantum dots. This is because quantum dots, including AIS/ZnS quantum dots, are usually capped with the strong coordinating ligand dodecanethiol which is hard to displace by other foreign thiols. Although some groups have reported the use of amphiphilic polymers to encapsulate quantum dots (CdSe or CdS), they need an overnight air-dry process followed by a heated film hydration, or a 24-hour dialysis to remove organic solvents or excess amphiphilic polymers. The heated hydration or the prolonged dialysis may be incompatible with certain functional groups (e.g., maleimide) on polymers for bioconjugation. Moreover, these studies used cadmium-based quantum dots, which have been concerns for biomedical applications and environments. Loading cadmium-free AIS/ZnS quantum dots into PLGA-PEG based micelles for biomedical applications is simple and fast and effectively avoids these potential limitations.

For CTX conjugation, the thiolation of CTX was completed by dispersing 12.5 nmol of CTX in 100 µL of PBS (pH8, 5 mM EDTA) with 125 nmol of Traut's reagent in 9 µL of PBS (pH 8, 5 mM EDTA) for 1 hour at room temperature. A volume of 87 µL of the prepared micelles in PBS (pH 6.7) was incubated with the thiolated CTX for 2-3 hours at room temperature. The resultant CTX-AIS/ZnS micelle product was purified using Zeba spin desalting columns (MWCO 7k) equilibrated with PBS, resuspended in 400 µL of PBS as a stock solution and stored at 4° C. before use. AIS/ZnS micelles without CTX conjugation were used as controls.

Figure 29:
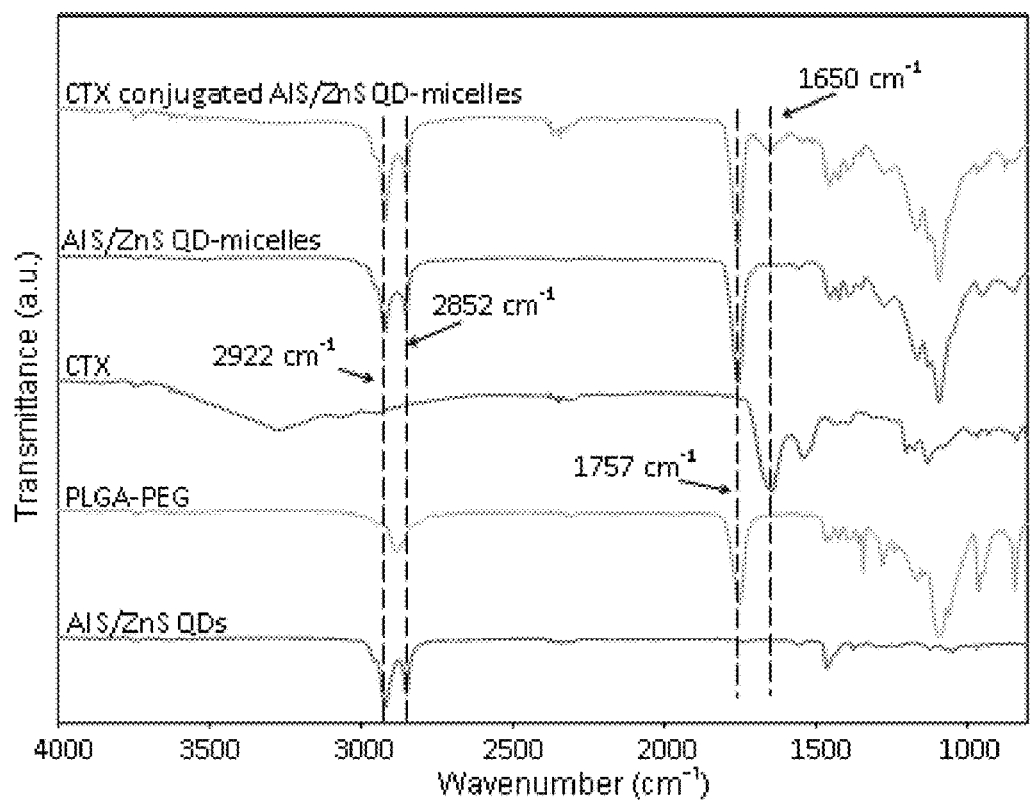
FIG. 29 illustrates FT-IR spectra of representative quantum dots, PLGA-PEG, CTX, quantum dot-micelles, and CTX-conjugated quantum dot-micelles.

For cellular imaging studies, CTX was used as a target ligand and used U-87 MG brain tumor cells as model cells. CTX is a 36-amino acid peptide that was originally isolated from scorpion venom, and specifically binds to tumors of neuroectodermal origin. Further studies have demonstrated that CTX is a specific matrix metalloproteinase II (MMP2) inhibitor and can bind with MMP2 present on the surface of glioma cells with high affinity. The specific binding results in loss of gelatinase activity, disruption in chloride channel currents, reduction in both MMP2 and chloride channel expressions, and internalization of chloride channels. Recent studies have also implicated annexin A2 (ANXA2) as a new recognition target of CTX in multiple tumor cell lines, which may activate similar uptake mechanisms as those of MMP2. U-87 is a human primary glioblastoma cell line expressing MMP2 receptors, and CTX can specifically bind to and be internalized into U-87. In this example, quantum dot-micelles were conjugated with CTX via a maleimide-thiol reaction. The CTX conjugation was confirmed by Fourier transform infrared spectroscopy, as shown in FIG. 29. The spectrum of the AIS/ZnS quantum dot-micelles exhibits the characteristics of both the alkyl chains in oleic acid and dodecanethiol from AIS/ZnS quantum dots, corresponding to the $CH_2$ stretching vibrations peaks at 2922 $cm^{-1}$ and 2852 $cm^{-1}$, and the ester carbonyl in PLGA from PLGA-PEG, corresponding to the C=O peaks at 1757 $cm^{-1}$. After CTX conjugation with the quantum dot-micelles, a new peak at 1650 $cm^{-1}$ corresponding to the N—H band of primary amines in lysine and arginine residues of CTX, appears in the spectrum of CTX-conjugated quantum dot-micelles. This appearance indicates the successful conjugation of CTX with the quantum dot-micelles.

In order to verify that (i) CTX conjugated quantum dot-micelles can be internalized into U-87 cells and (ii) the internalization is due to the CTX-MMP2 interaction, two sets of examples were performed. In the first, U-87 cells were incubated with CTX conjugated quantum dot-micelles spiked in DEME with 2% BSA for 2 hours. In the second, 400 µM 1,10-phenanthroline was added to DEME, keeping all other conditions same. 1,10-phenanthroline is a broad-spectrum MMP2 inhibitor and can disrupt the MMP2 activity by chelating and removing Zn ions from the catalytic domain of MMP2. As a result, 1,10-phenanthroline can block the interaction between CTX and MMP2 and thus the sequential cellular internalization process.

Figure 30A:
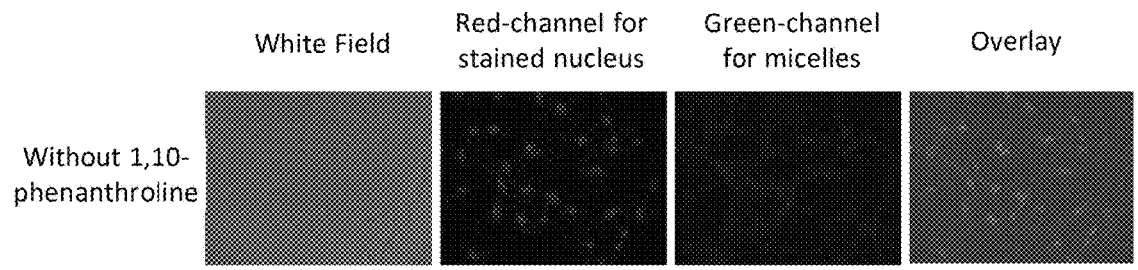
FIGS. 30A-30C illustrate results obtained from analysis of representative quantum dots made using a disclosed thermal decomposition method embodiment.
Figure 30B:
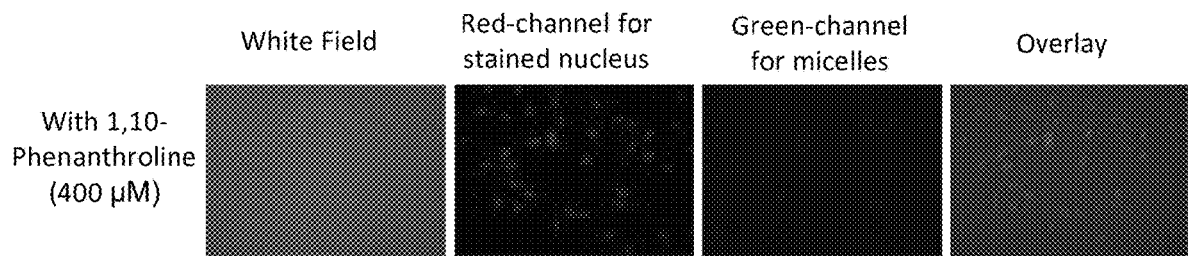
Figure 30C:
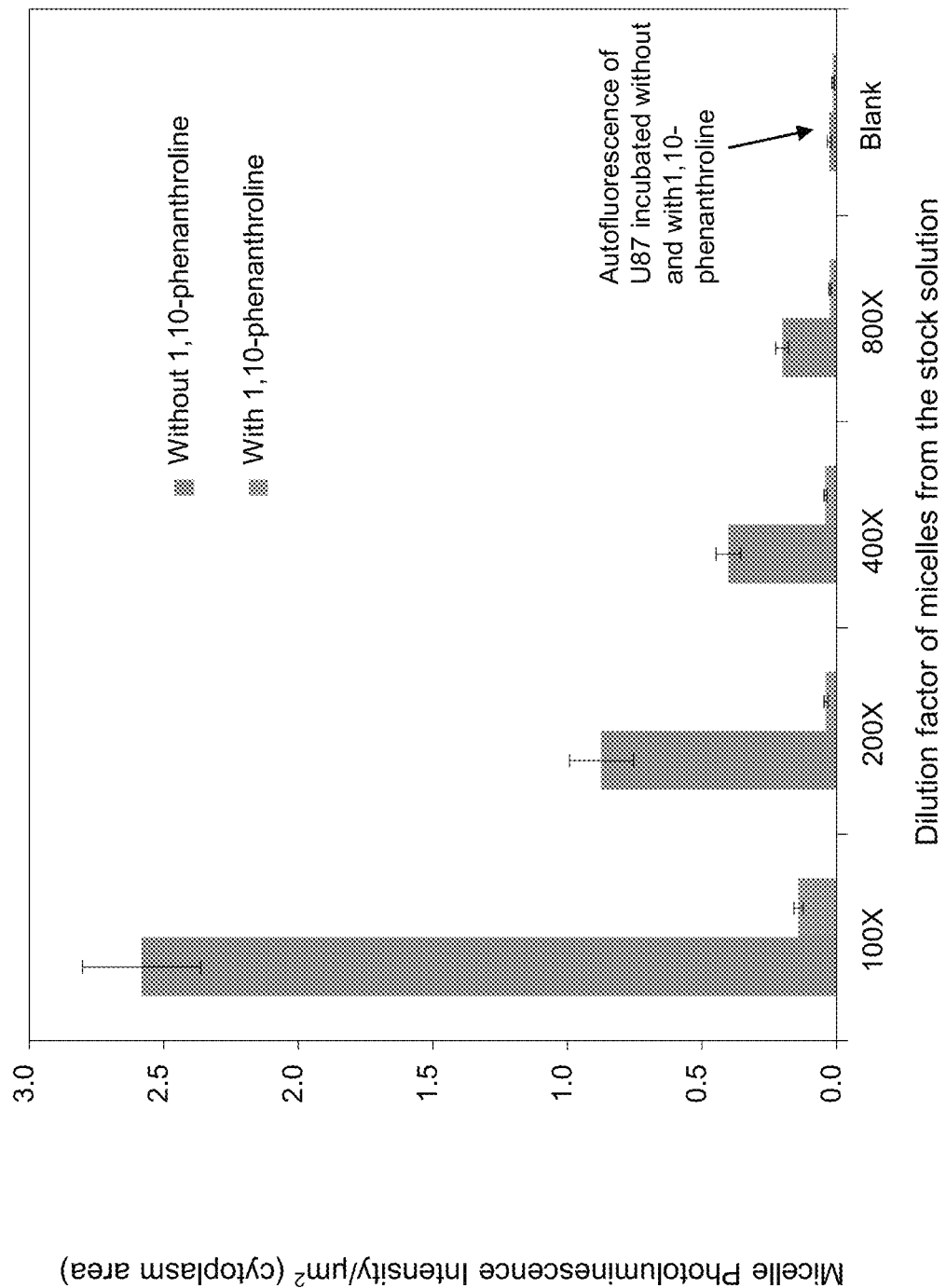

After incubation, the U-87 cells from two sets of examples were washed, fixed, stained and imaged. Representative confocal images shown in FIG. 30A demonstrates the cellular uptake/internalization of CTX-conjugated quantum dot-micelles by U-87 cells. The representative confocal images in FIG. 30B illustrate the quenching effect of 1,10-phenanthroline on uptake/internalization. FIG. 30C shows quantitative data (the fluorescence intensity from the internalized quantum dot-micelles per unit cytoplasm area counting>200 cells) comparing cellular uptake/internalization and the quenching effect under the different concentrations or dilutions of CTX-conjugated quantum dot-micelles (100-800 times dilution). These results demonstrate that the internalization of CTX-conjugated quantum dot-micelles into U-87 cells is caused by an interaction between CTX and MMP2.

Figure 31E:
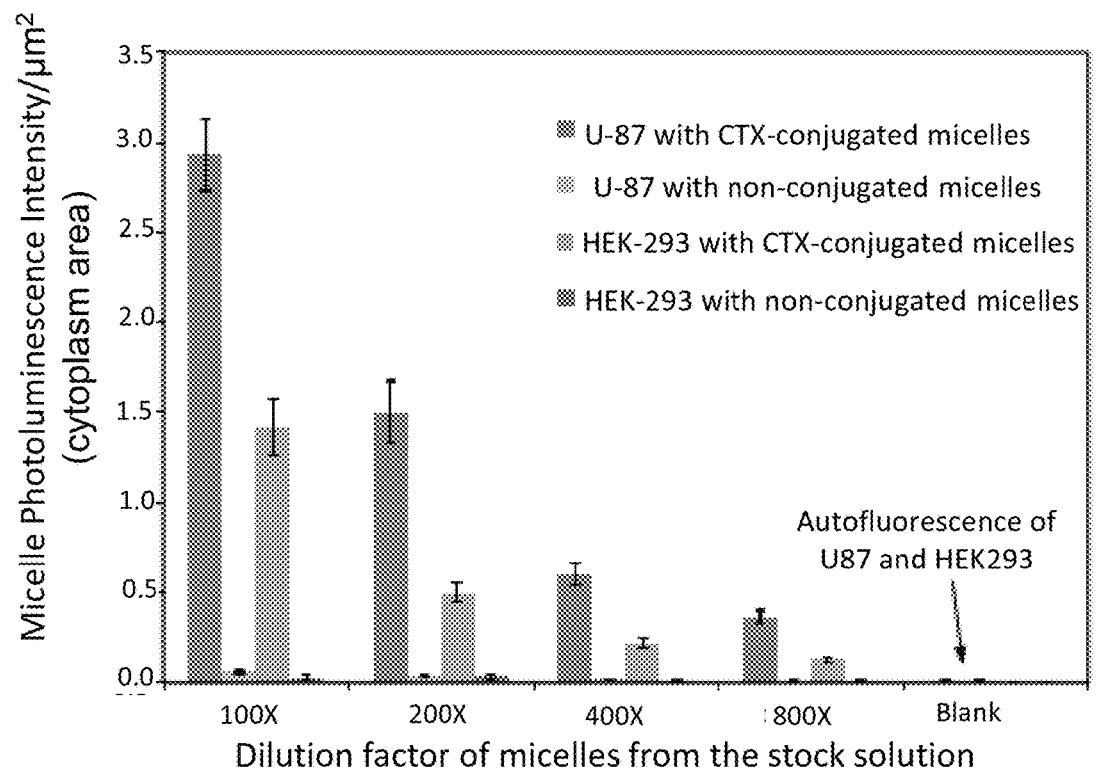

To further confirm that CTX-conjugated quantum dot-micelles is specific to U-87, human embryonic kidney 293 cells (HEK-293), a nonmalignant cell line that does not express MMP2 and ANXA2 on cell surfaces, was used as controls to examine their response to quantum dot-micelles conjugated with/without CTX and compared to those of U-87. FIGS. 31A and 31B and FIGS. 31C and 31D show the representative cellular uptake images (overlaid confocal images) for U-87 and HEK-293, respectively, under the same quantum dot-micelle concentration or dilution. FIG. 31E shows fluorescence intensity (from the internalized quantum dot-micelles) per unit cytoplasm area under a series of dilutions of quantum dot-micelles stock solutions. It can be seen that U-87 cells do internalize more CTX-conjugated quantum dot-micelles (FIG. 31E, left-most bar of each bar group) than HEK-293 (FIG. 31E, third bar from the left for each bar group), and non-conjugated quantum dot-micelles (FIG. 31E, second and fourth bars from the left for each bar group) produce no significant cellular uptake by both cell lines. Through this comparison, it can be concluded that CTX-conjugated quantum dot-micelles are specific to U-87. Interestingly, it was also observed that HEK-293 did internalize some CTX-conjugated quantum dot-micelles at a high concentration. Some pioneer work has reported that CTX can increase the rate of pinocytic internalization. The cellular uptake of CTX-conjugated micelles may involve pinocytosis mechanisms in high concentration ranges.

Using PLGA-PEG to wrap AIS/ZnS quantum dots is an effective approach for phase transfer and bio-applications. The AIS/ZnS quantum dot-micelles can be used as image contrasts or probes can be used to detect endogenous targets expressed on brain tumor cells, or more broadly to cell- or tissue-based diagnosis and therapy. Similar quantum dot-micelles also can be constructed using the zwitterionic polymeric coatings described herein.

Synthesis of Cu:AIS Quantum Dots

Ag(DDTC) (0.1 mmol), In(Ac)$_3$ (0.2 mmol) and DDT (4 mL) were added in a three-necked round bottom flask equipped with a condenser and magnetic stir bar. This mixture was degassed under vacuum for 30 min at 125° C. until the solution became clear. The solution temperature was then increased to 190~200° C. under a flow of argon and held at this temperature for 10 min to grow AIS cores. After the reaction was completed, the solution was cooled to room temperature, and 4 mL of ODE was added to the AIS core growth solution without any purification. Then the solution was heated to 120° C. under vacuum for 20 min and then to 190~200° C. under argon. Copper precursors prepared by dissolving CuI (0.2 mmol) in DDT (8 mL) were injected into the solution for the formation of Cu:AIS quantum dots. After 10 min growth, the solution was cooled to room temperature. The nanocrystal solution was purified repeatedly with the solvent combinations of hexane/ethanol and chloroform/acetone by centrifugation and then dried under vacuum. For the synthesis of Cu:AIS quantum dots with different Cu doping concentrations, the Cu initial concentrations ([Cu]/([Ag]+[In])) were changed in the range from 0~10 mol %. Small amounts of the reaction solution (0.1~0.2 mL) were collected using a syringe at different time intervals and injected into hexane in clean vials to terminate growth of quantum dots. All solutions collected from the example were diluted in a quartz cuvette with hexane for UV-Vis absorbance and photoluminescence measurements.

Synthesis of Cu:AIS/ZnS Quantum Dots

For ZnS shell growth, the zinc precursor was prepared by dissolving zinc stearate (0.4 mmol) in ODE (4 mL) at 140° C., and the sulfur precursor was prepared by dissolving sulfur (0.4 mmol) in DDT (3.2 mL) and TOP (0.8 mL). The growth of the ZnS shell on Cu:AIS quantum dots was conducted in situ without purification of the core solution. Once the growth of cores was completed, the nanocrystal solution was heated up to 210° C. under argon. Then both zinc and sulfur precursors were injected in sequence 3 times to the Cu:AIS growth solution in 0.5 mL portions at 15 min intervals. After the reaction was finished, mixtures were cooled down to room temperature and Cu:AIS/ZnS quantum dots were purified using hexane/ethanol and chloroform/acetone, and dried under vacuum.

Quantum yields of quantum dots were calculated according to the following equation, using standard references including Rhodamine 6G (emission peak at 556 nm, QY=95% in ethanol) and Oxazine 170 (emission peak at 640 nm, QY=63% in methanol), $QY_S=QY_R\times(I_S/I_R)\times(A_R/A_S)\times(n_S/n_R)^2$ where $QY_S$ and $QY_R$ are the quantum yields of sample and a standard reference, respectively; $I_S$ and $I_R$ are the integrations of fluorescence emissions of sample and a standard reference, respectively; $A_S$ and $A_R$ are the corresponding absorbance of sample and a standard reference, respectively; and $n_S$ and $n_R$ are the refractive indices of the corresponding solvents. In quantum yield measurements, the absorbance of each sample or each standard reference deviated by less than 0.1. For each sample, the standard reference with the most similar absorption and/or luminescence characteristics was chosen for quantum yield measurements.

Amphiphile-Encapsulated Cu:AIS/ZnS Composite Probes for Cellular Imaging 6.67% Cu:AIS/ZnS quantum dots were encapsulated using zwitterionic polymeric coatings using methods disclosed above. 2.4 mg Cu:AgInS$_2$/ZnS quantum dots in THF (900 μL) and 1.6 mg zwitterionic amphiphiles in CHCl$_3$-MeOH (64 μL) were dispersed into water under sonication. After sonication, the organic solvents were removed by rotary evaporation at room temperature and the sample was filtered through a 0.2 μm syringe filter. Empty micelles or single-nanoparticle based micelles were removed by centrifugation at 18 000 rpm for 25 min. The collected micelles were dispersed in 400 μL of water as the micelle stock.

60 μL of the micelle stock was reacted with 0.3 mg RGD in borate buffer for 2~3 hours after the activation of carboxyl groups on micelles' surface using EDC/Sulfo-NHS. The RGD-conjugated micelles were washed by centrifugation, suspended in 200 μL borate, and stored at 4° C. before use as the conjugate stock. The same reaction was done for the conjugation of micelles with RAD peptide, and the RAD-conjugated micelles were used as a negative control. Non-conjugated micelles were also used as a control. A U-87 MG human brain glioblastoma cell line was cultured (37° C., 5% $CO_2$) on glass coverslips coated with gelatin in MEM medium with 10% FBS until 50~80% confluency was achieved. The human embryonic kidney cell line HEK-293 was cultured (37° C., 5% $CO_2$) on glass coverslips coated with PDL (poly-D-lysine) in RPMI-1640 medium with 10% FBS until 50~80% confluency was achieved. For the specific cell targeting examples, cells were incubated with RGD-conjugated micelles in DMEM with 2% BSA at various concentrations or dilutions. As controls, cells were also incubated with RAD-conjugated micelles and non-conjugated micelles. After 3 h incubation, cells were gently rinsed three times with PBS, fixed with 4% PFA in PBS solution for 20 minutes and washed three times with PBS. For cellular nuclei staining, cells were incubated with DAPI, washed three times with PBS, and then mounted on glass slides. Cells were imaged using a confocal microscope. Two-way ANOVA was applied to detect the differences among two cell lines. SAS (Statistical Analysis Software) 9.4 was used for data analysis.

Figure 35A:
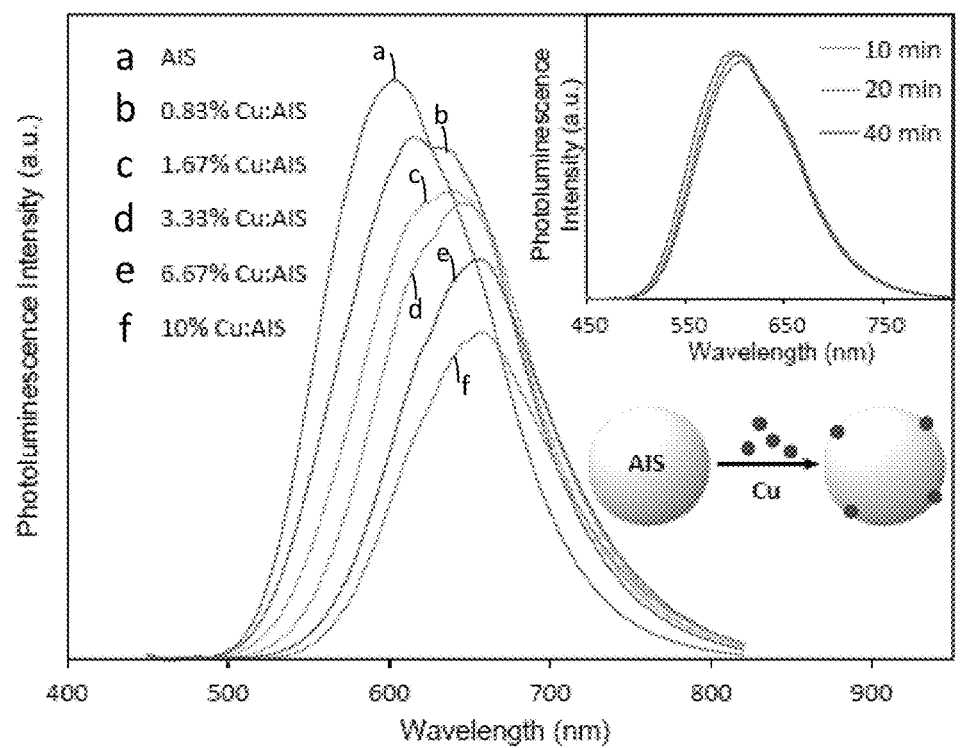
FIGS. 35A and 35B show results obtained from analyzing representative doped quantum dots.
Figure 35B:
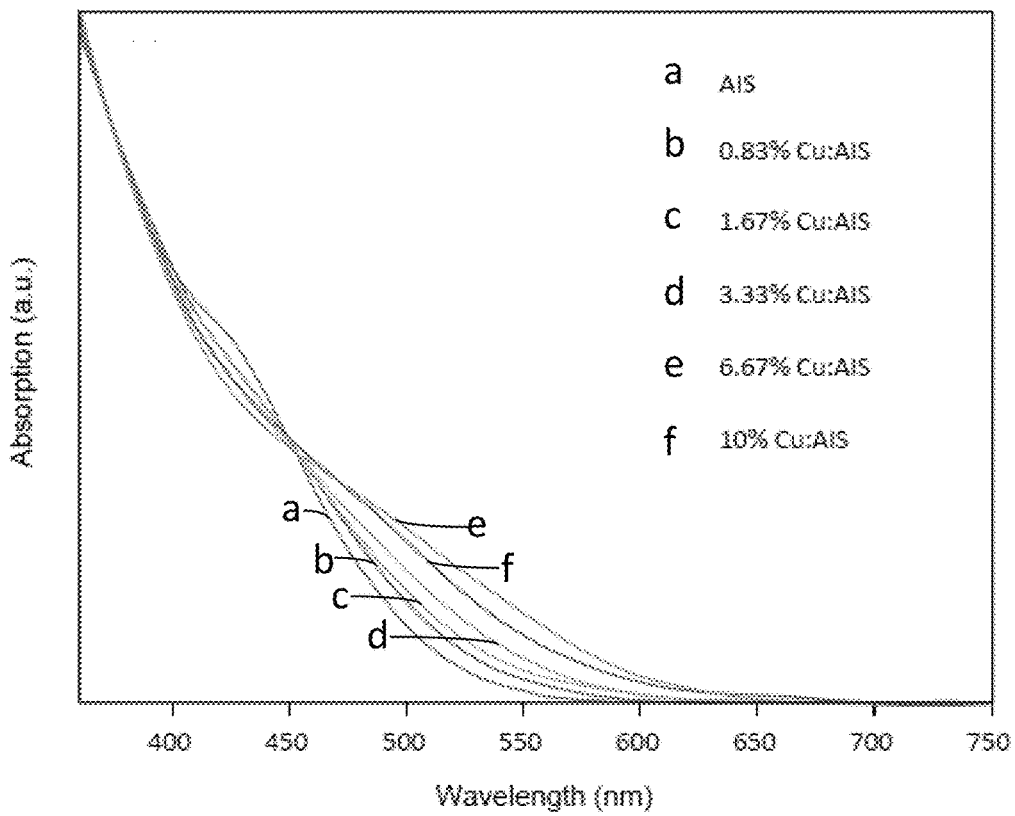

Cu atoms were doped into AIS composites through a surface doping strategy—AIS quantum dots were first grown via thermal decomposition and then Cu precursors were injected into the AIS NC solution to react with AIS quantum dots. FIG. 35A presents the effect of Cu concentrations on the photoluminescence spectra of Cu doped AIS quantum dots (Cu:AIS quantum dots). It can be seen that the photoluminescence peak wavelength shows a continuous red shift from around 600 to 660 nm as Cu concentration in reaction is increased from 0 to 6.67% (molar percentage), and the red shift is not significant for Cu concentration above 6.67% or at 10%. The corresponding UV-vis absorption spectra of these Cu:AIS quantum dots are shown in FIG. 35B As the Cu concentration increases, the absorbance edges of these samples are monotonously shifted to longer wavelength. The absorption edge of 10% Cu:AIS is similar to that of 6.67% Cu:AIS. This observation is consistent with their photoluminescence spectra. In FIG. 35A it can also be seen that quantum yields of Cu:AIS quantum dots decrease from around 30% to 20% with the increase of Cu concentrations from 0% to 6.67%. Quantum yield of 10% Cu:AIS quantum dots even decrease further even though the photoluminescence is not red shifted. Through further comparing the photoluminescence spectra of Cu:AIS quantum dots, it can be seen that their shapes are also affected by Cu concentrations. The shape dependence on Cu concentration implicates that Cu atoms are incorporated into NC lattices and cause some changes of the lattice energy band or contribute to NC photoluminescence mechanisms. Of note, as shown in the inset of FIG. 35A the photoluminescence of non-doped or pure AIS quantum dots prepared in the thermal decomposition is hard to be tuned by the NC growth time. It can be seen that Cu doping is an effective way to tune nanocrystal photoluminescence.

Figure 36A:
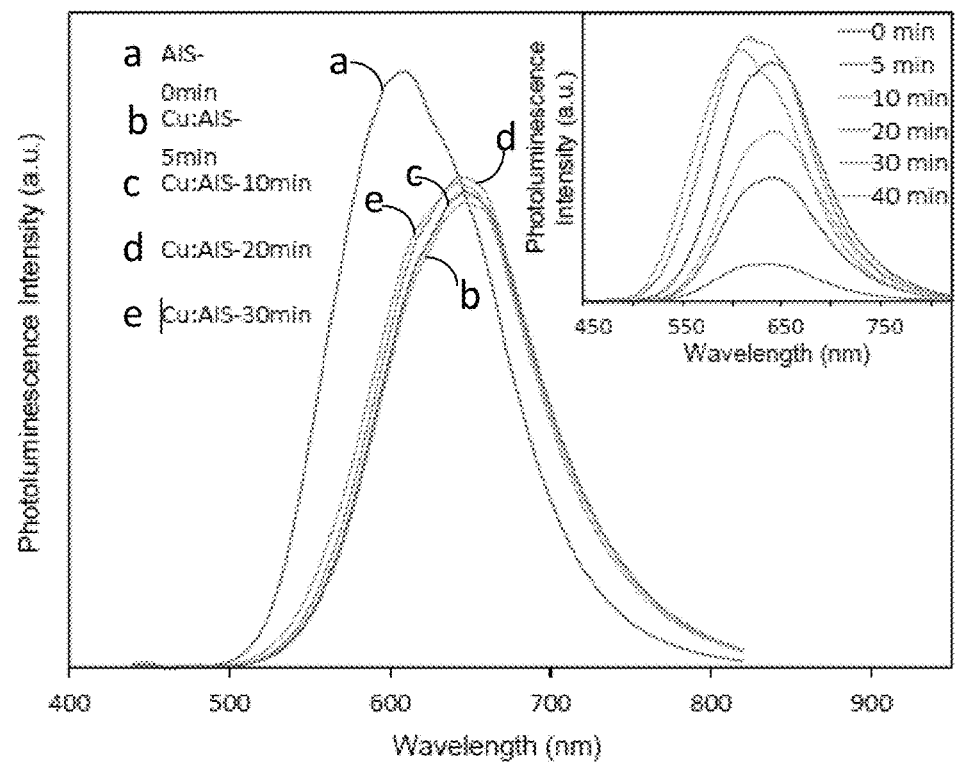
FIGS. 36A and 36B show results obtained from time course analysis of Cu-doped quantum dots.
Figure 36B:
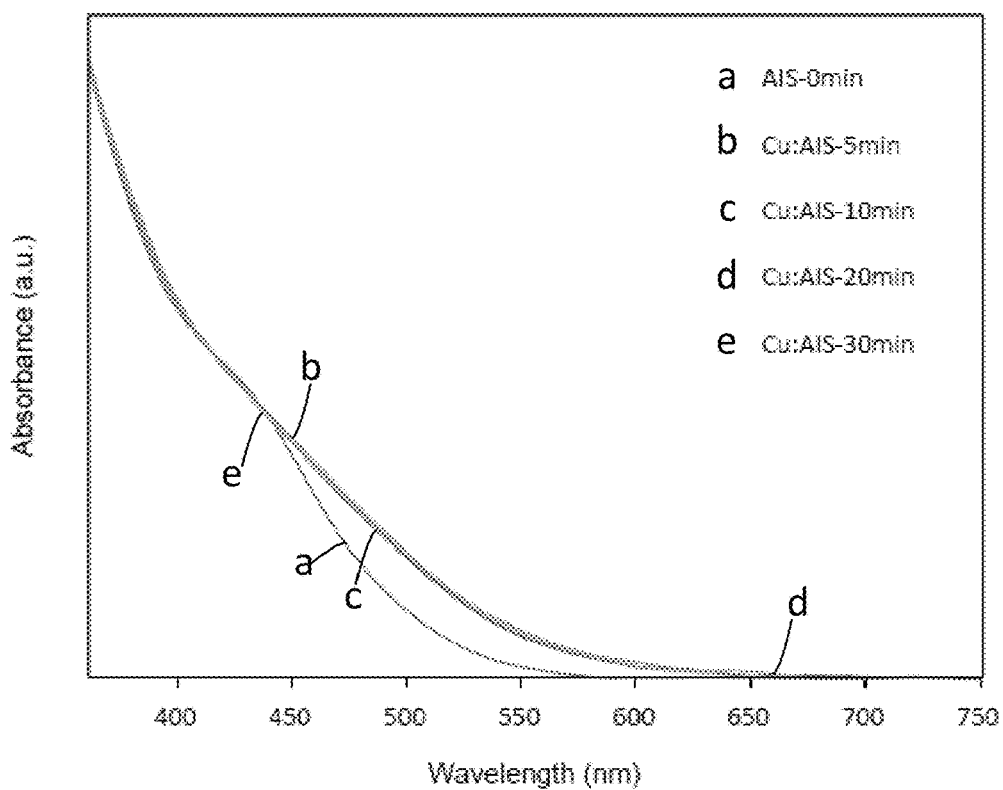

The reason to adopt surface doping is that the optical property of quantum dots is more controllable than that using homogenous doping. With 3.33% Cu:AIS quantum dots as a demonstration, FIG. 36A shows the evolution of their photoluminescence spectra in the time course of reaction through surface doping. It can be seen that around 45 nm red-shift occurs at 5 min after Cu injection. With further prolonged reaction time, no remarkable change in photoluminescence is observed with respect to peak wavelength and quantum yield. The similar observation is also noticed in their absorption spectra as shown in FIG. 36B This demonstrates that the Cu doping of AIS quantum dots is a fast and reliable process. However, with the same starting materials, if Cu precursor is mixed with silver and indium precursors in DDT for thermal decomposition, the photoluminescence of the produced quantum dots is observed to red shift to around 650 nm and then blue shift to around 600 nm, as shown in the inset of FIG. 36A. Moreover, the photoluminescence spectra become broader in the time course of reaction. It is possible that the final products could have both sub-populations of doped AIS quantum dots and non-doped (or intrinsic) AIS quantum dots. Clearly, surface doping is a better approach to control the NC optical property.

Figure 37A:
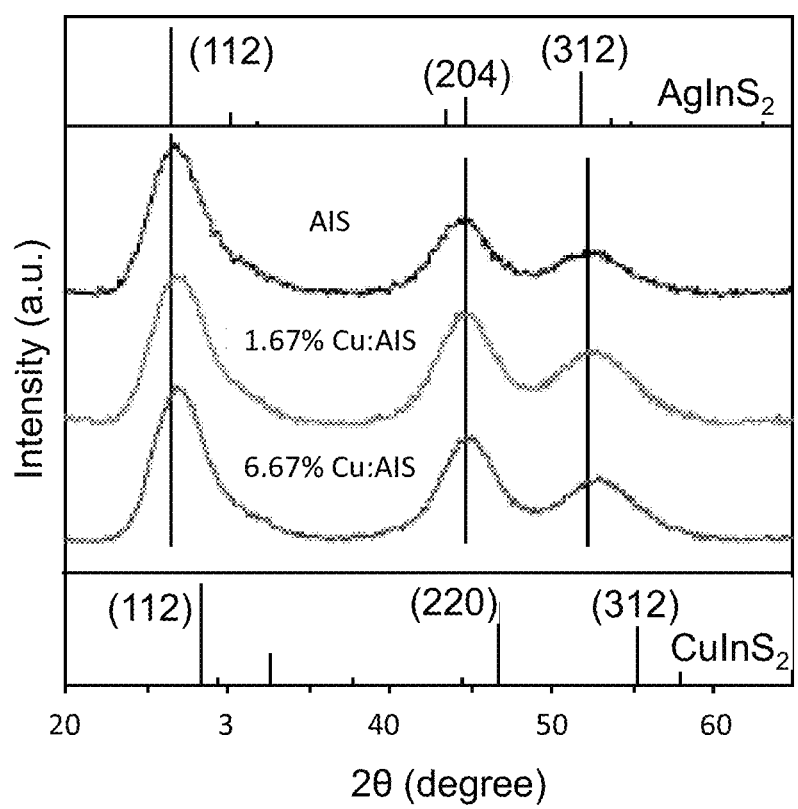

To further understand the optical property of Cu:AIS quantum dots, these quantum dots were first characterized using XRD, TEM and EDX. Three representative samples (pure AIS, 1.67% Cu:AIS and 6.67% Cu:AIS) were investigated. As shown in FIG. 37A, the XRD pattern of the pure AIS quantum dots can be indexed with a tetragonal $AgInS_2$ crystal. Three apparent diffraction peaks observed at 2θ=26.8, 44.7, and 52.6° can be assigned to diffractions from the (112), (204) and (312) planes of the tetragonal phase. Compared to the pure AIS quantum dots, diffraction patterns of Cu:AIS quantum dots slightly shifts to the higher angle side and approaches the 2θ values of the tetragonal $CuInS_2$ (CIS) along with the increase of Cu concentration. Since the ionic radius of Cu (0.74 nm) is smaller than that of Ag (1.14 nm), the observed shifts of the XRD patterns indicate the gradual replacement of Ag with Cu to form Cu:AIS quantum dots instead of forming individual CIS quantum dots. These three samples were further characterized using TEM. FIG. 37B-37D present their TEM and high-resolution TEM (HR-TEM) images. TEM images of AIS and Cu:AIS quantum dots show that their sizes are at 4~5 nm, indicating that the incorporation of Cu does not significantly influence the particle size. The HRTEM images show lattice plane spacings of 0.342, 0.340, and 0.332 nm for AIS, 1.67% Cu:AIS, and 6.67% Cu:AIS quantum dots, respectively. The values of these spacings are corresponding to (112) planes determined from diffraction peaks at around 26-28° of XRD patterns in FIG. 37A. Both HRTEM and XRD data reveal that the obtained Cu:AIS quantum dots are not a mixture of individual AIS and CIS phases, but a Cu:AIS crystal. The energy dispersive X-ray (EDX) spectra further confirms that AIS quantum dots are composed of Ag, In, and S and Cu:AIS quantum dots are composed of Cu, Ag, In and S. The resultant elemental compositions of AIS and Cu:AIS quantum dots are summarized in Table 1. For pure AIS quantum dots, the atomic ratio between Ag and In is close to 1:1. For Cu:AIS quantum dots, as Cu concentration is increased in the reaction, more Cu atoms are doped into quantum dots but the atomic percentage of Ag decreases. This observation indicates that Cu atoms enter the AIS structure and partially replace Ag atoms. The reason for the preferential substitution of Ag instead of In probably is that the Ag—S bond is weaker than the In—S bond. More Cu atoms doped into quantum dots could cause more structure or surface defects quenching the NC photoluminescence for lower quantum yields. The EDX analysis of 10% Cu:AIS quantum dots was also conducted and the result shows that the element atomic ratio of Cu:Ag:In:S is 5.1:16.4:27.3:51.2. Compared to the element atomic ratio for 6.67% Cu:AIS quantum dots (as shown Table 1), more Cu atoms are observed in 10% Cu:AIS quantum dots. It is possible that the Cu level in AIS quantum dots may get saturated for 6.67% Cu:AIS quantum dots, and thus with a higher Cu concentration in doping, additional Cu atoms may be absorbed on NC surface to quench photoluminescence but not affect the position of photoluminescence peak.

Figure 38A:
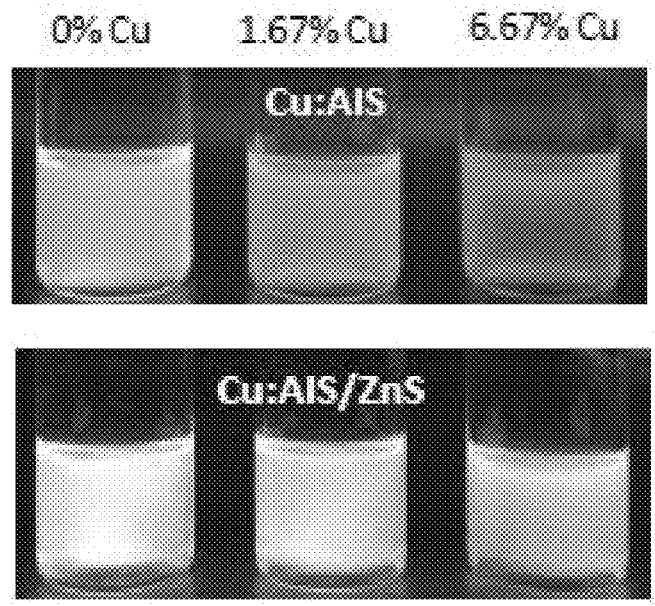
FIGS. 38A-38D show results obtained from characterization analysis of representative embodiments of Cu-doped core quantum dots and Cu-doped core/shell quantum dots.
Figure 38B:
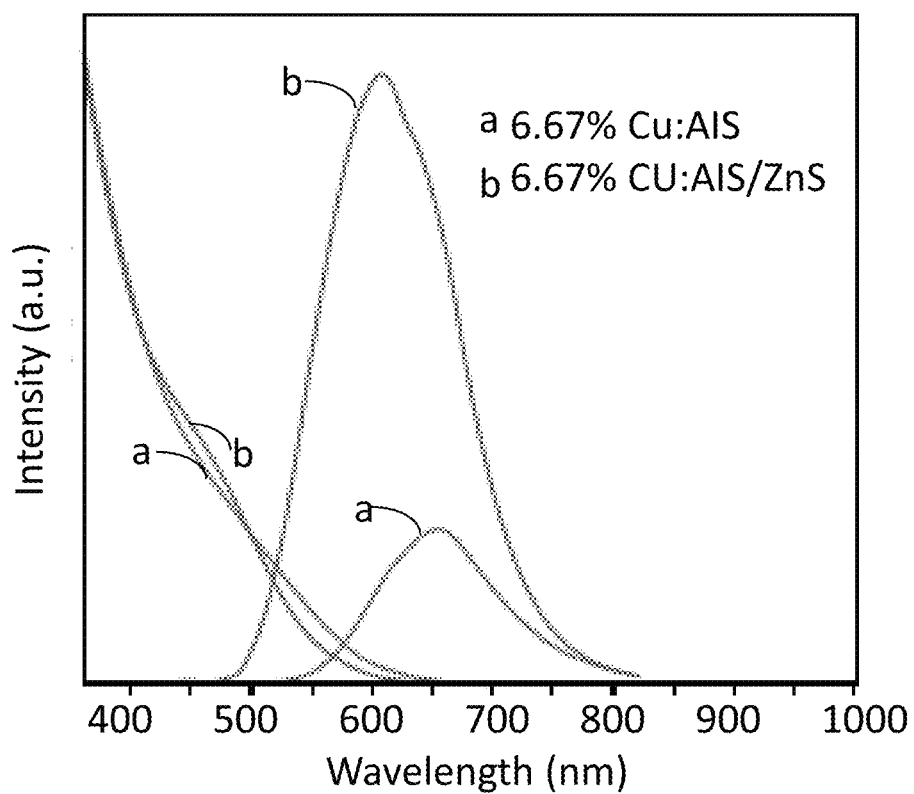
Figure 38C:
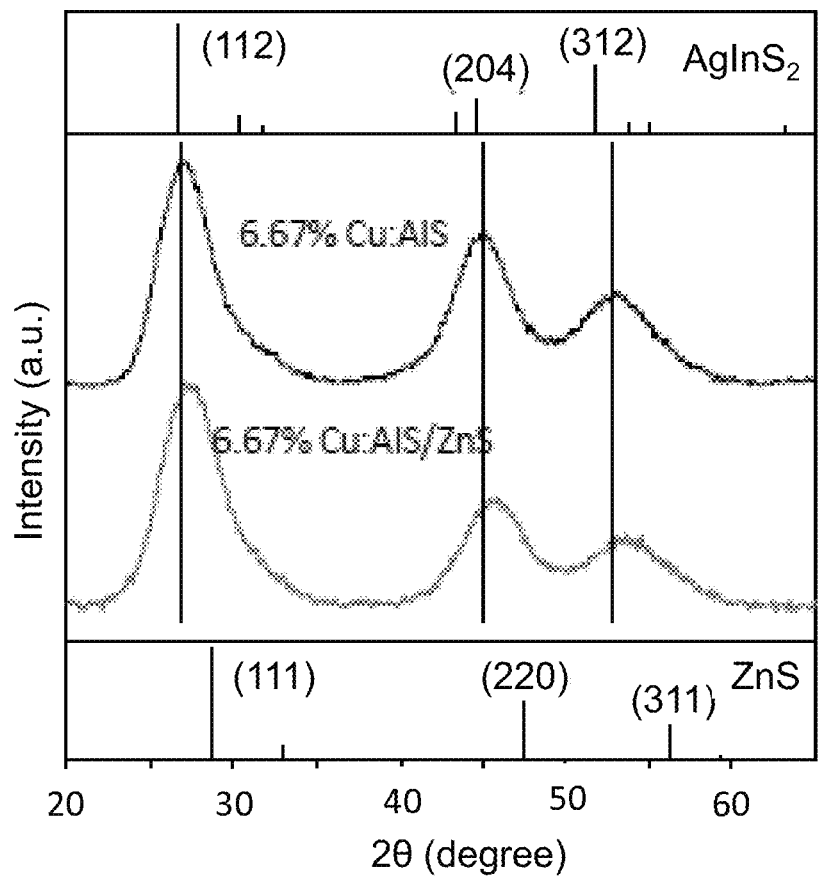
Figure 38D:
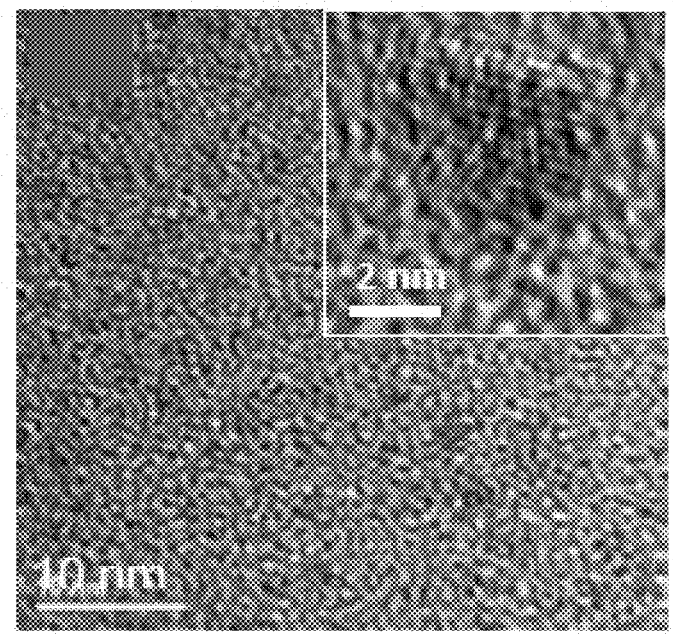

To enhance the photoluminescence quantum yield, AIS and Cu:AIS quantum dots were passivated with a shell of ZnS to form AIS/ZnS and Cu:AIS/ZnS quantum dots. The quantum yields of AIS/ZnS, 1.67% Cu:AIS/ZnS and 6.67% Cu:AIS quantum dots are around 52.6%, 52.6%, 56.5% quantum yields, respectively. All of them present 30~50 nm blue shift in their photoluminescence spectra after ZnS coating. FIG. 38A shows digital photographs of Cu:AIS and Cu:AIS/ZnS quantum dots suspended in organic solvents under a UV lamp. It can be seen that the emission colors of cores and core/shell structures are Cu-concentration dependent. FIG. 38B demonstrates the typical photoluminescence and absorption spectra of 6.67% Cu:AIS quantum dots before and after ZnS coating. FIG. 38C shows that the XRD diffraction pattern of the 6.67% Cu:AIS/ZnS quantum dots has a similar profile to that of 6.67% Cu:AIS cores, and shows a medium phase of Cu:AIS and ZnS crystals. The three main peaks shift to the high angle side and locate in the middle position of the pattern of Cu:AIS quantum dots and the standard pattern of cubic ZnS, which further suggests that Zn atoms are deposited or diffused to the surface of the Cu:AIS cores. FIG. 38D shows the corresponding TEM and HRTEM images. The HRTEM image also reveals that the quantum dots have a clear lattice fringe with a plane spacing of 0.310 nm. The lattice planet spacing is close to that of the (111) plane in cubic ZnS quantum dots. Similar to the core samples, Cu:AIS/ZnS quantum dots have a size around 4~5 nm. Probably, the ZnS coating is mainly dominated by zinc etching into core quantum dots. As confirmed by the EDX spectrum of 6.67% Cu:AIS/ZnS quantum dots, the elemental composition ratios of Cu, Ag, In, Zn, and S obtained from EDX analysis were 2.1%, 9.5%, 19.8%, 12.7%, and 55.8%, respectively. Both the atomic percentages of Ag and In decrease, however, the amount of Ag is reduced to a greater extent. At the same time, the atomic percentage of Zn is increased. The more reduction of Ag atomic percentage in Cu:AIS/ZnS quantum dots is probably due to Zn etching to preferentially replace Ag during the ZnS shell growth. The Cu concentration in the core/shell structures was observed to be is slightly lower than that of the Cu:AIS cores. Such results suggest that in the Cu doping process, a portion of Cu atoms may sit on the surface of AIS cores and be replaced by zinc atoms during ZnS coating or zinc etching, and another portion of Cu atoms may diffuse into an inner layer of AIS lattice which cannot be replaced by zinc but still affect the photoluminescence of core/shell quantum dots.

Figure 39A:
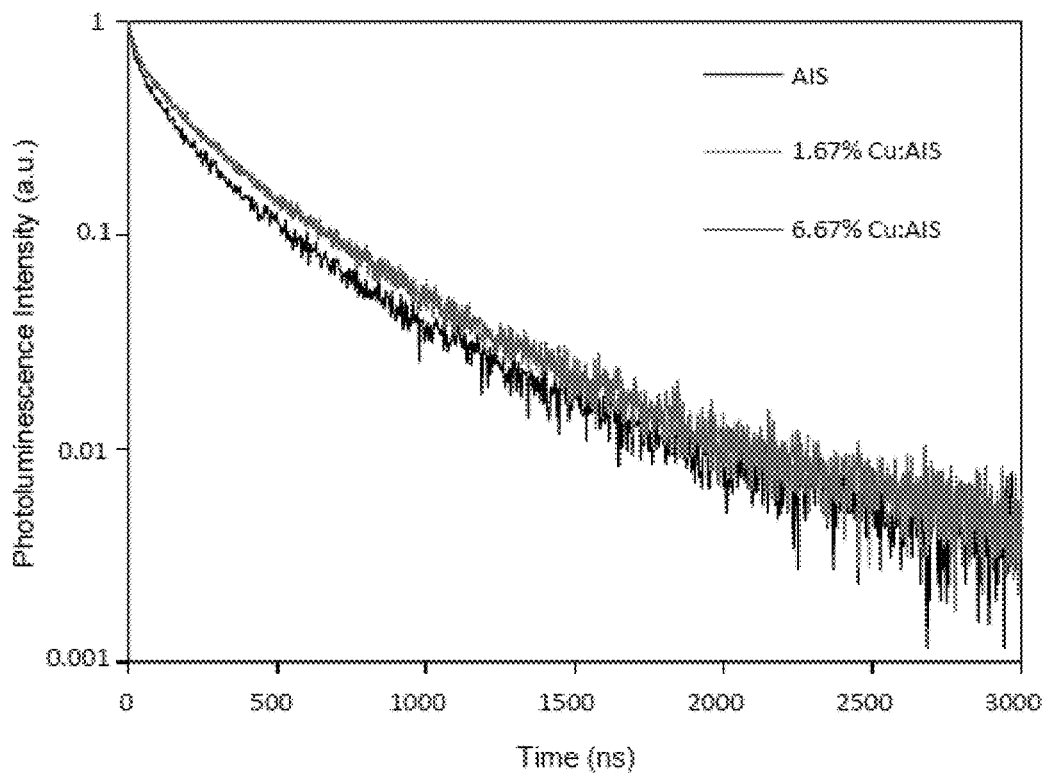
FIGS. 39A and 39B are photoluminescence decay curves showing the photoluminescence decay for representative Cu:AIS quantum dots (FIG. 39A) and Cu:AIS/ZnS quantum dots (FIG. 39B).
Figure 39B:
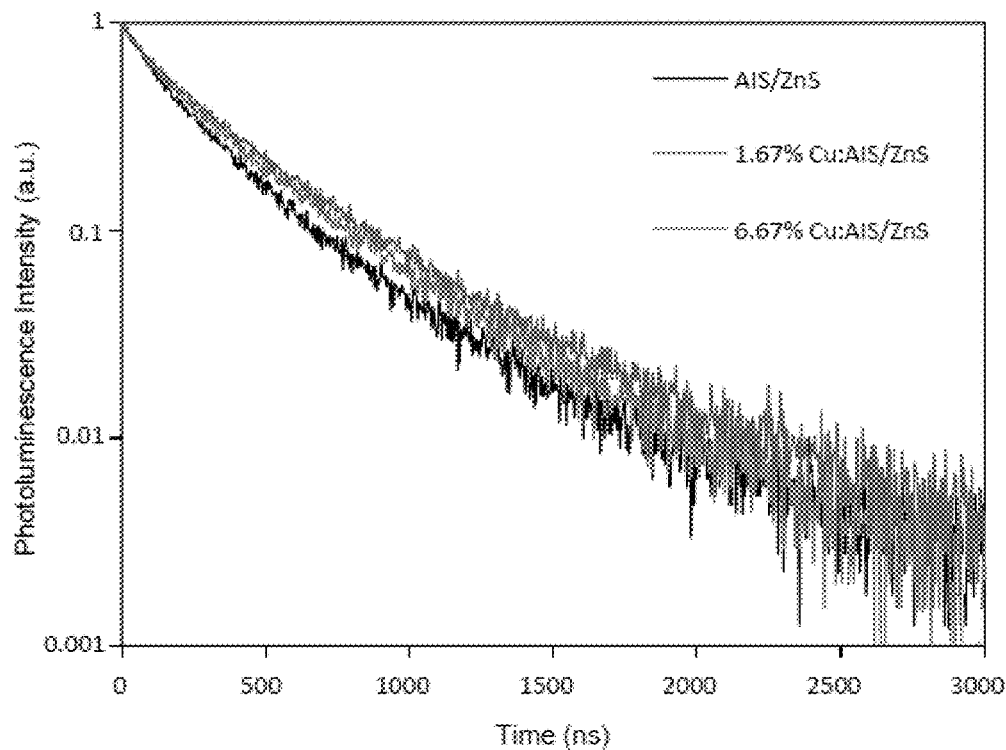

FIG. 39A shows the decay curves for AIS, 1.67% Cu:AIS, and 6.67% Cu:AIS quantum dots. FIG. 39B presents the decay curves for their corresponding core/shell structures. For each decay curve, a biexponential function $(l(t) = A1e^{-t/\tau 1} + A2e^{-t/\tau 2})$ was used to fit the curve. $\tau 1$ and $\tau 2$ are the short and long lifetime parameters, respectively. A1 and A2 are the amplitudes of the decay components at t=0. Table 2 lists the extracted characteristics parameters ($\tau 1$, $\tau 2$, A1, and A2) for all investigated samples. According to literature, the photoluminescence lifetime parameters of AIS quantum dots could be associated with different electron-hole recombination pathways or mechanisms. After light excitation, electrons will be relaxed from conduction bands to surface trap states and donor states. The short lifetime is be attributed to electron transition from surface trap states (caused by surface defects) to valence bands. The long lifetime is attributed to electron transition from donor states to acceptor states, which results in the broad emission peaks of AIS quantum dots. From Table 2, it is observed that upon comparing A1 parameter for each core and its corresponding core/shell structure, A1 parameter is decreased and $\tau 1$ is increased after ZnS shell growth. Considering the ZnS shell growth on each core causes quantum yield enhancement, it is reasonable to attribute the decrease of A1 to the minimization of surface defects. The prolonged $\tau 1$ of core/shell structures probably is associated with electron transition from near-surface trap states or deep trap states to valence bands. The near-surface trap states or deep trap states could be closer to the donor states in energy levels and thus have a relatively longer lifetime for electrons. Upon examining the effect of Cu concentrations on A1 and $\tau 1$ of AIS cores, it can be seen that A1 of Cu:AIS cores is decreased compared to that of non-doped AIS cores. According to the literature model, the A1 decrease should implicate the minimization of surface defects and thus the enhancement of quantum yield upon Cu doping. However, FIG. 35A show that Cu doping causes the decrease of quantum yields. Moreover, as shown in FIG. 35A with low Cu concentrations, a shoulder in the photoluminescence spectrum is presented at the right side of the main photoluminescence peak. As Cu concentration increases, the shoulder is shifted to the left side of the main photoluminescence peak. As shown in Table 2, Cu doping also prolongs the average photoluminescence lifetime of quantum dots. It seems that although the literature model can well explain the effect of ZnS coating as well as some phenomena of non-doped or intrinsic AIS quantum dots, a more sophisticated model or a different viewpoint is needed to explain the photoluminescence mechanisms of Cu:AIS quantum dots as well as the reason for the prolonged average photoluminescence lifetime upon Cu doping. According to literature, the decrease of quantum yields with the increase of Cu doping levels is probably due to two reasons: (i) more defects in Cu:AIS lattice are created; (ii) high doping concentration causes closer distance between Cu atoms and cause strong Cu—Cu interaction and photoluminescence quenching. The transition/change of the photoluminescence spectrum shape versus Cu concentration in doping may be caused by multiple electron-hole recombination paths. According to literature, Cu doping could introduce additional Cu $T_2$ states in the bandgap of AIS quantum dots. Meanwhile, our material characterization shows that Cu can etch and replace Ag in AIS host quantum dots, and the doped Cu could form a Cu—In—S(CIS) layer on AIS surface. The formed CIS layer could possess some nature of CIS bandgap, and new donor-acceptor pairs from CIS structures could be existing. The new CIS donor-acceptor pairs also are energy levels incorporated in the bandgap of AIS hosts. On the other hand, AIS also has its own donor-acceptor pairs. As a result, there could be several electron-hole recombination paths. The photoluminescence of quantum dots should be a synergistic effect of all these recombination paths. Cu $T_2$ states and/or new CIS donor-acceptor pairs are Cu-concentration dependent, and thus gradually they can be more dominant than AIS donor-acceptor pairs as the Cu concentration increases in the doping process. As a result, the change of the photoluminescence spectrum shape versus Cu concentration can be observed. With respect to the prolonged average photoluminescence lifetime, due to the incorporation of Cu $T_2$ states, the excited-state lifetime of the dopant emission is longer than the excitonic emission and the surface emission. Thus, Cu doped quantum dots gain a prolonged photoluminescence lifetime. The new CIS donor-acceptor pairs also are energy levels in the AIS bandgap and they could function as Cu $T_2$ states to prolong the average photoluminescence lifetime. Of note, these $T_2$ states and/or new CIS donor-acceptor pairs should be the causes for the emission at longer wavelengths (or red-shift in the doping process). Through this measurement on photoluminescence decay, it is also good to know that the average photoluminescence lifetime of the produced quantum dots is in the range of 300~500 ns. The quantum dots with long lifetimes are attractive for bioimaging—as bioimaging probes, they can be scanned using microscopy not only in regular intensity-based fluorescence mode but also in time-resolved fluorescence mode. Specifically, in the time-resolved mode, the long lifetime can distinguish NC fluorescence signals from the fast decaying autofluorescence in cells/tissue, and ensure quantum dots for more sensitive imaging.

TABLE 2

| Nanocrystals | $\tau_1$/ns | $A_1$ | $\tau_2$/ns | $A_2$ | $\tau_{avg}$/ns |
| --- | --- | --- | --- | --- | --- |
| AIS | 49 | 51.6% | 369 | 48.4% | 329 |
| 1.67% Cu:AIS | 62 | 45.2% | 413 | 54.8% | 374 |
| 6.67% Cu:AIS | 66 | 44.8% | 414 | 55.2% | 374 |
| AIS/ZnS | 125 | 49.2% | 416 | 50.8% | 350 |
| 1.67% Cu:AIS/ZnS | 131 | 41.7% | 461 | 58.3% | 405 |
| 6.67% Cu:AIS/ZnS | 151 | 42.2% | 499 | 57.8% | 436 |

Figure 40:
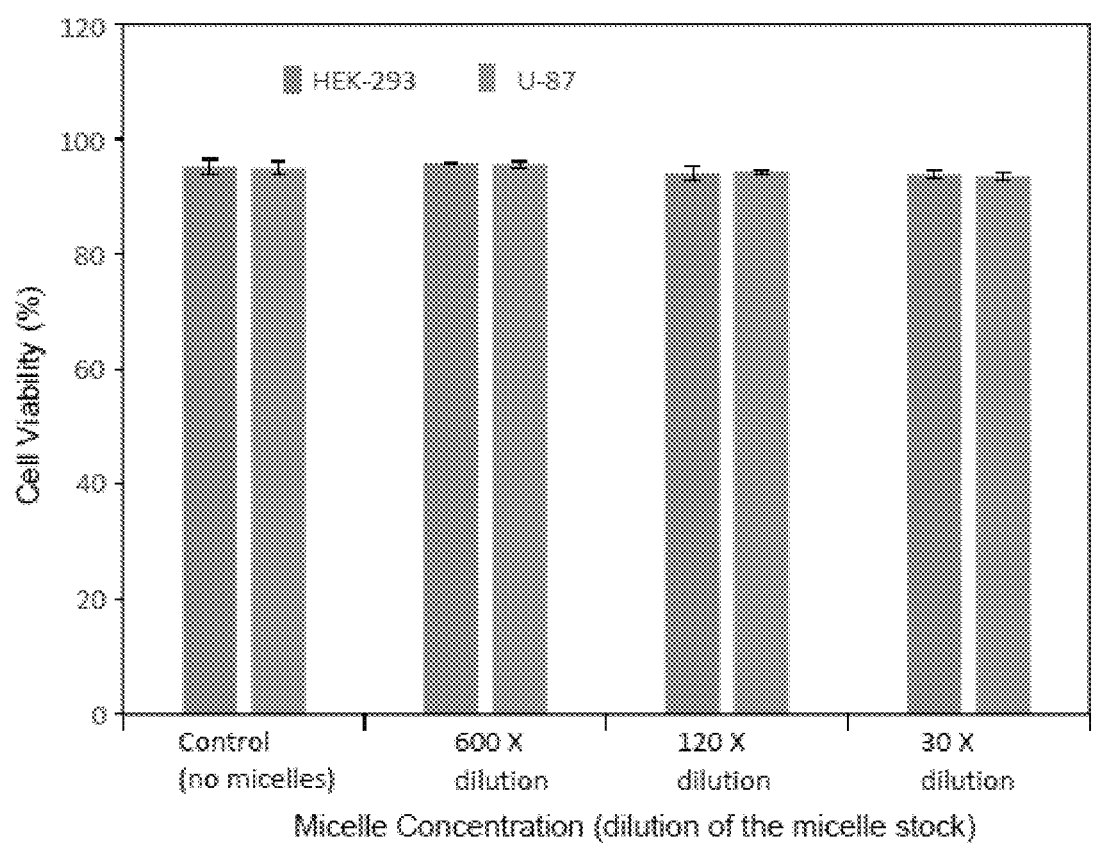
FIG. 40 is a graph of cell viability (%) as a function of composite (referred to as "micelle") concentration showing cell viability of U-87 MG cell and HEK-293 cells treated with representative composite embodiments at different concentrations over 48 hours.
Figure 41C:
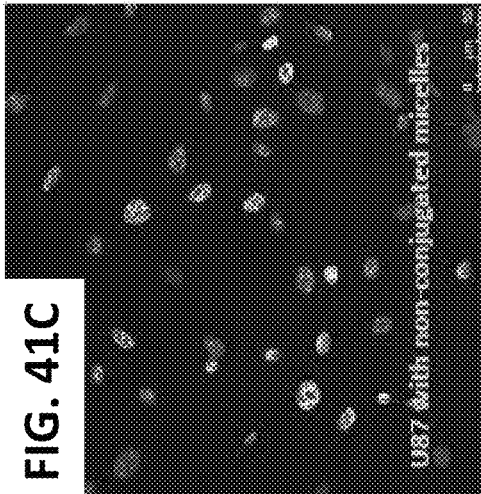
FIGS. 41-41F are overlaid confocal images demonstrating the cellular uptake/internalization of RGD-conjugated, RAD-conjugated, and non-conjugated composites under the same dilution or concentration of composites (25 times dilution from the conjugate stock) by U-87 (FIGS. 41A-41C) and HEK-293 (FIGS. 41D-41F).
Figure 41B:
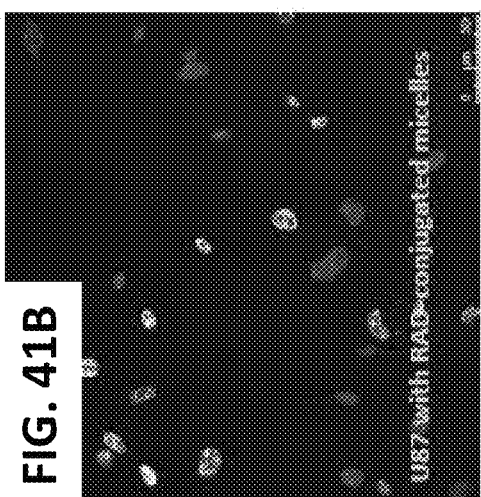
Figure 41A:
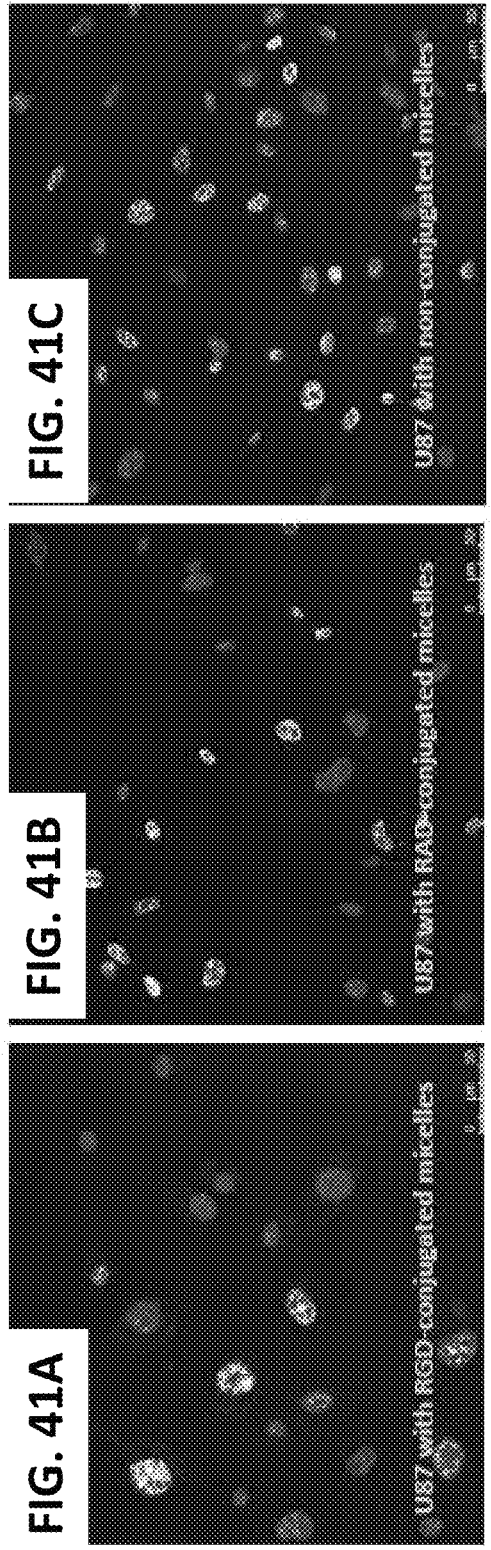
Figure 41F:
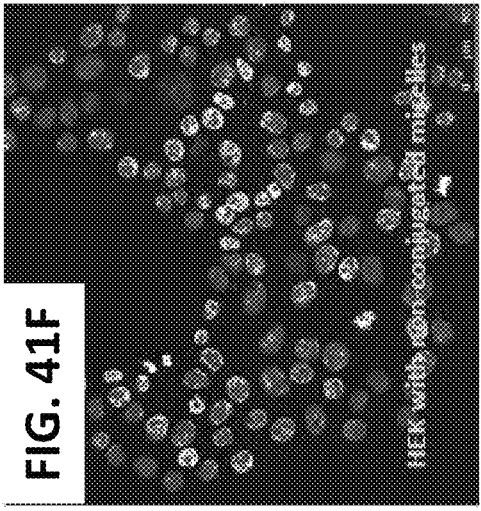
Figure 41E:
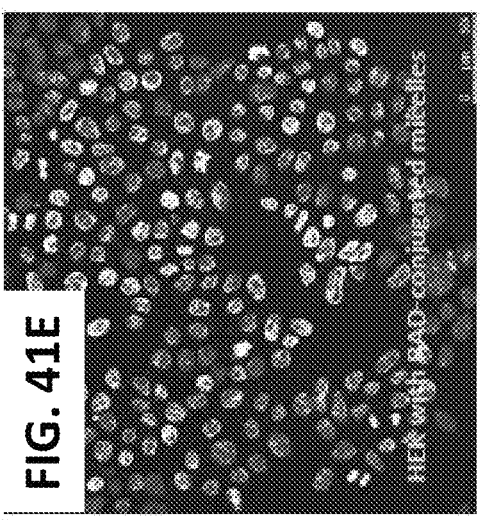
Figure 41D:
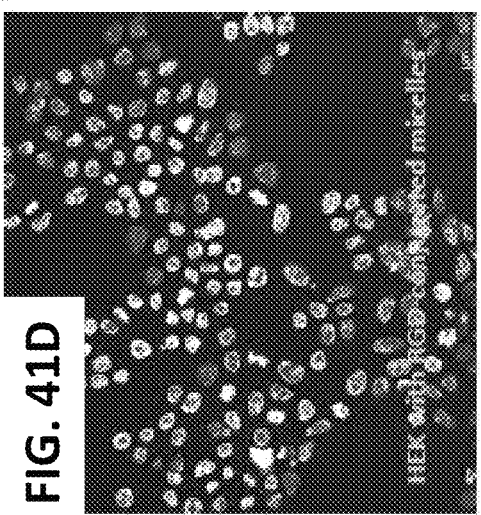
Figure 42:
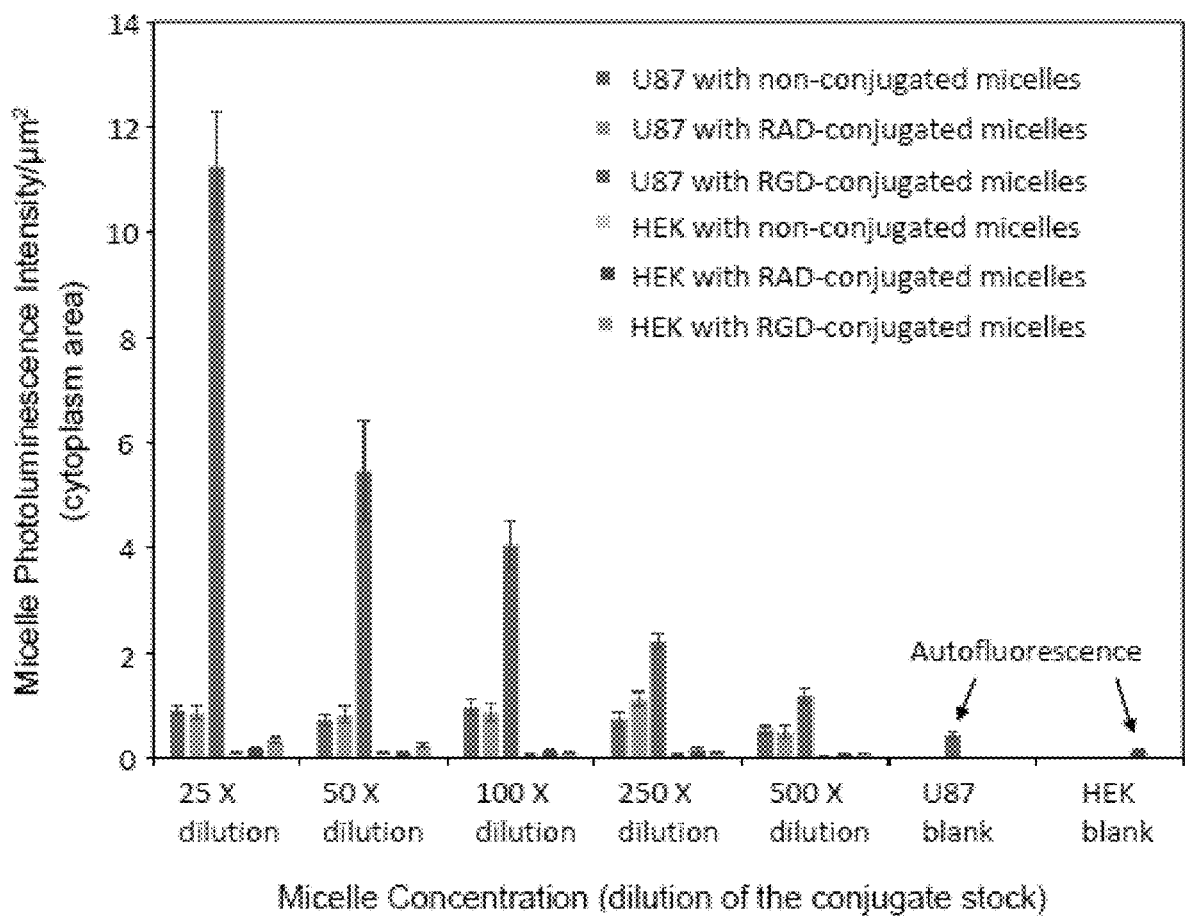
FIG. 42 is a graph of composite (or "micelle") photoluminescence intensity as a function of composite ("micelle") concentration showing the fluorescent intensity per unit area of cytoplasm for U-87 and HEK-293 cells incubated with non-conjugated micelles, RAD-conjugated micelles, and RGD-conjugated composites with different dilutions or concentrations (all p values for each comparison are less than 0.001).

To demonstrate potential biomedical applications of Cu:AIS/ZnS quantum dots (i.e., specific targeting to brain tumor cells), composites with 6.67% Cu:AIS/ZnS quantum dots and a zwitterionic polymer coating were formed through self-assembling. Human primary glioblastoma U-87 MG cells and human embryonic kidney 293 cells (HEK-293) are cell lines used in this example. The cytotoxicity of the micelles was first studied using these two cell lines. Cells were incubated with micelles in growth medium with 10% FBS at various concentrations for 48 hours at 37° C. After incubation, the growth medium was removed and the cells released from well bottom using stempro accutase, and then stained with FDA/PI to determine live vs dead cells using flow cytometry (Dead cells are red staining by PI and live cells are green staining by FDA). The cell viability was calculated as the ratio of live cells over the sum of live cells and dead cells. FIG. 40 shows the measured cell viabilities for U-87 MG (right-most bar for each bar group) and HEK-293 (left-most bar for each bar group) after 48-hour incubation with micelles under different concentrations. It can be seen that for each cell line, the cell viabilities under all different micelle concentrations are around 95%, which are comparable to that of controls (no micelles in incubation). Thus the micelles loaded with Cu:AIS quantum dots are biocompatible. On the basis of the cytotoxicity example, these micelles were further conjugated with RGD and RAD peptides via EDC/Sulfo-NHS mediated reaction. RGD can specifically target to integrin αvβ3 overexpressed on U-87 MG cells and thus it is specific to U-87 MG cells. RAD with a molecular structure similar to RGD but is nonspecific to U-87 MG cells and thus used as a control. HEK-293 not expressing integrin αvβ3 is used as a cell line control. In cellular uptake studies, each cell line was incubated with the RGD-conjugated micelles, RAD-conjugated micelles, and non-conjugated micelles under difference concentrations or dilutions in MEM medium with 2% BSA for 3 hours at 37° C. After incubation, cells were gently rinsed three times with PBS, fixed with 4% PFA in PBS solution for 20 minutes and washed three times with PBS. Afterwards, cells were incubated with DAPI for cellular nuclei staining, washed three times with PBS, and then mounted on glass slides. The mounted cells were then imaged using a Leica confocal microscope and images were analyzed using ImageJ. FIGS. 41A-41F shows representative cellular uptake images (overlaid confocal images) for U-87 and HEK-293. Quantitative data counting>100 cells for each experimental condition were presented in FIG. 42. It can be seen that for each micelle concentration or dilution, U-87 cells internalize more RGD-conjugated micelles (FIG. 42, third bar from the left for each bar group) than HEK-293 (FIG. 42, sixth bar from the left for each bar group). RAD-conjugated (FIG. 42, second and fifth bars from the left for each bar group) and non-conjugated micelles (FIG. 42, left-most and fourth bars from the left for each bar group) had no significant cellular uptake by any of cell lines. Clearly, the micelles using Cu:AIS/ZnS quantum dots can be applied to the detection of endogenous targets expressed on brain tumor cells. In this embodiment, the micelles were scanned in regular intensity-based fluorescence mode. Scanning also could be conducted in time-resolved fluorescence mode to achieve better image quality with respect to signal/noise ratio. In addition, radioactive Cu may be doped into AIS quantum dots so that the achieved quantum dots have dual imaging functionalities for positron emission tomography (PET) and luminescence imaging. Considering the hydrophobic core of micelles can also be loaded with both drugs and image contrasts, the specific cellular internalization suggests that the cadmium-free Cu:AIS/ZnS-micelles may also load drugs to be versatile nanoplatforms for cell- or tissue-based diagnosis and therapy.

Effect of Chloride Surface Passivation on AgInS$_2$ (AIS) QDs

Figure 44A:
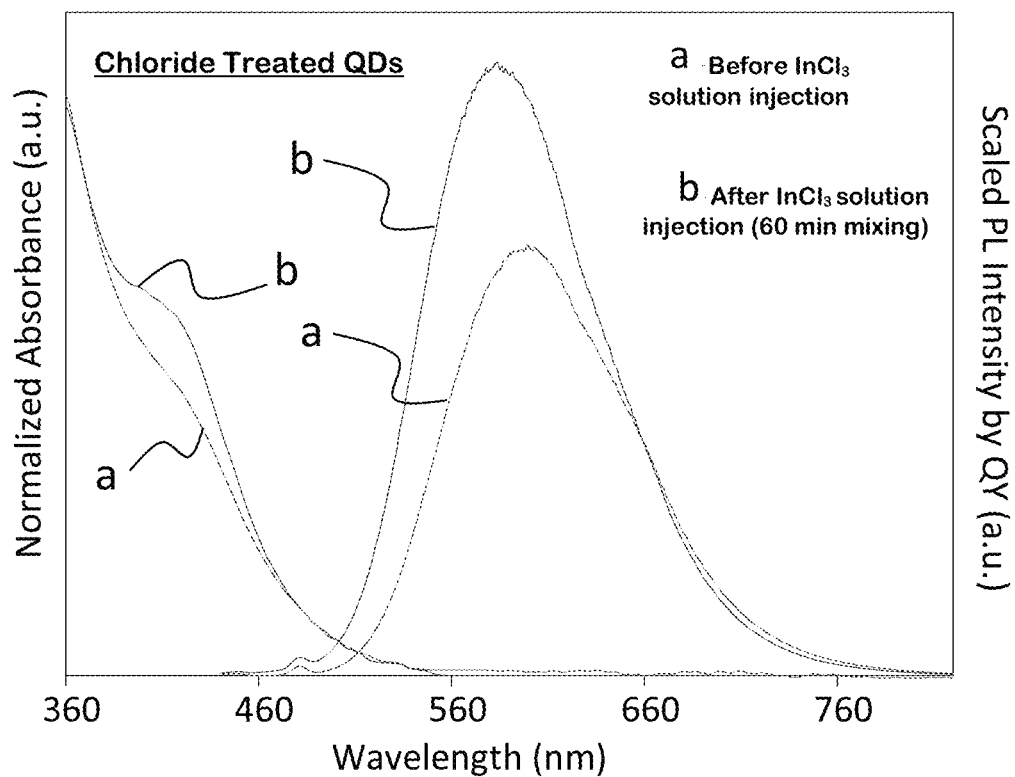
FIGS. 44A and 44B are spectra showing absorbance and photoluminescence intensity for composites comprising chloride shells (FIG. 44A) and control examples without chloride shells (FIG. 44B).
Figure 44B:
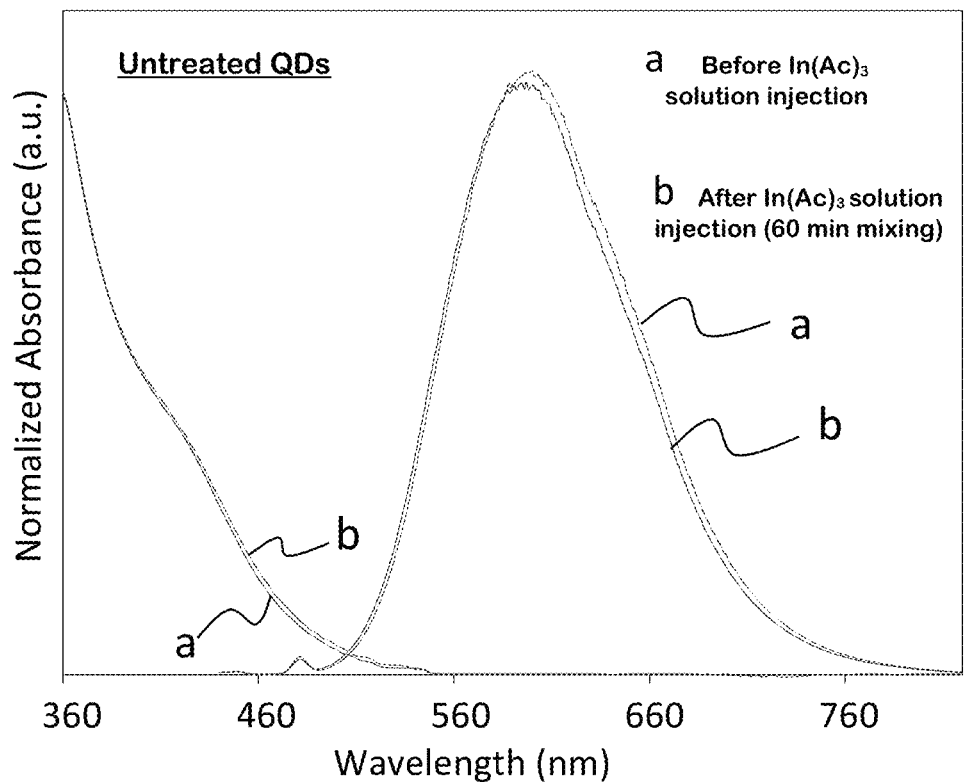
Figure 45A:
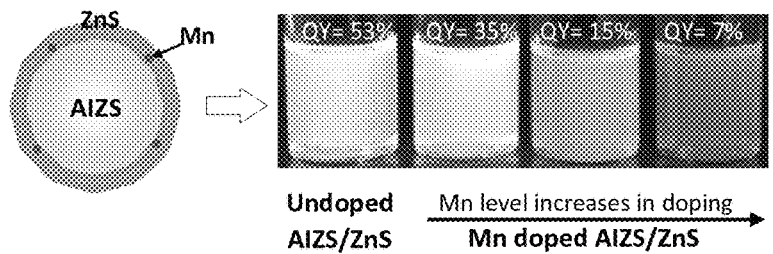
FIGS. 45A-45C illustrate results obtained from analyzing Mn-doped nanocrystals as described herein, wherein the surface doping is used.
Figure 45B:
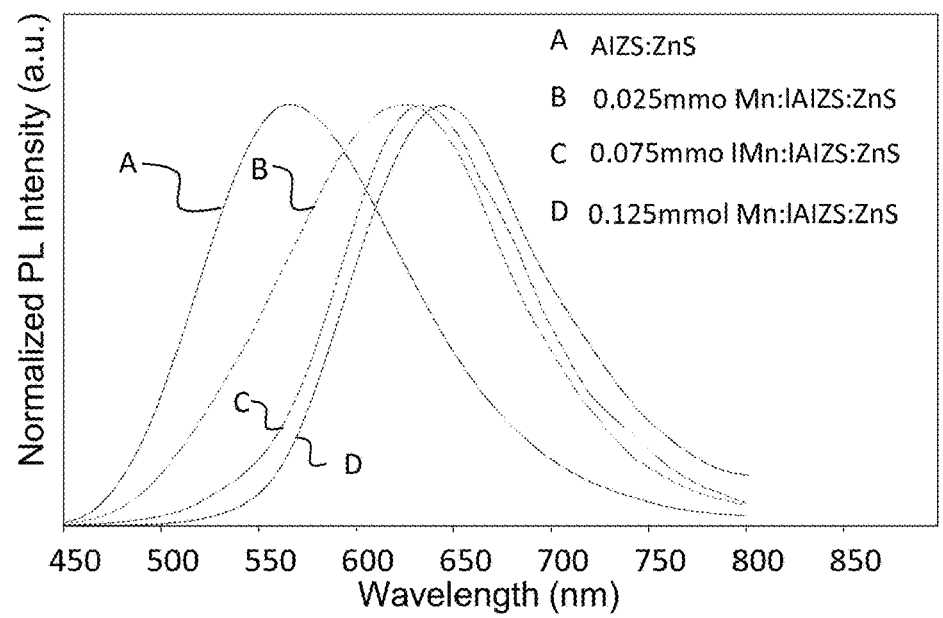
Figure 45C:
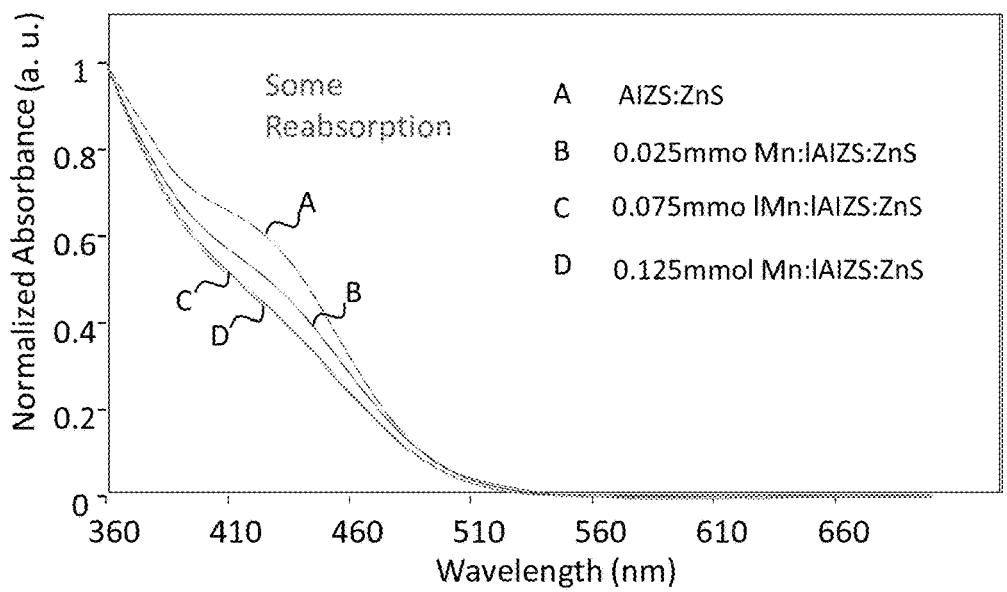
Figure 46:
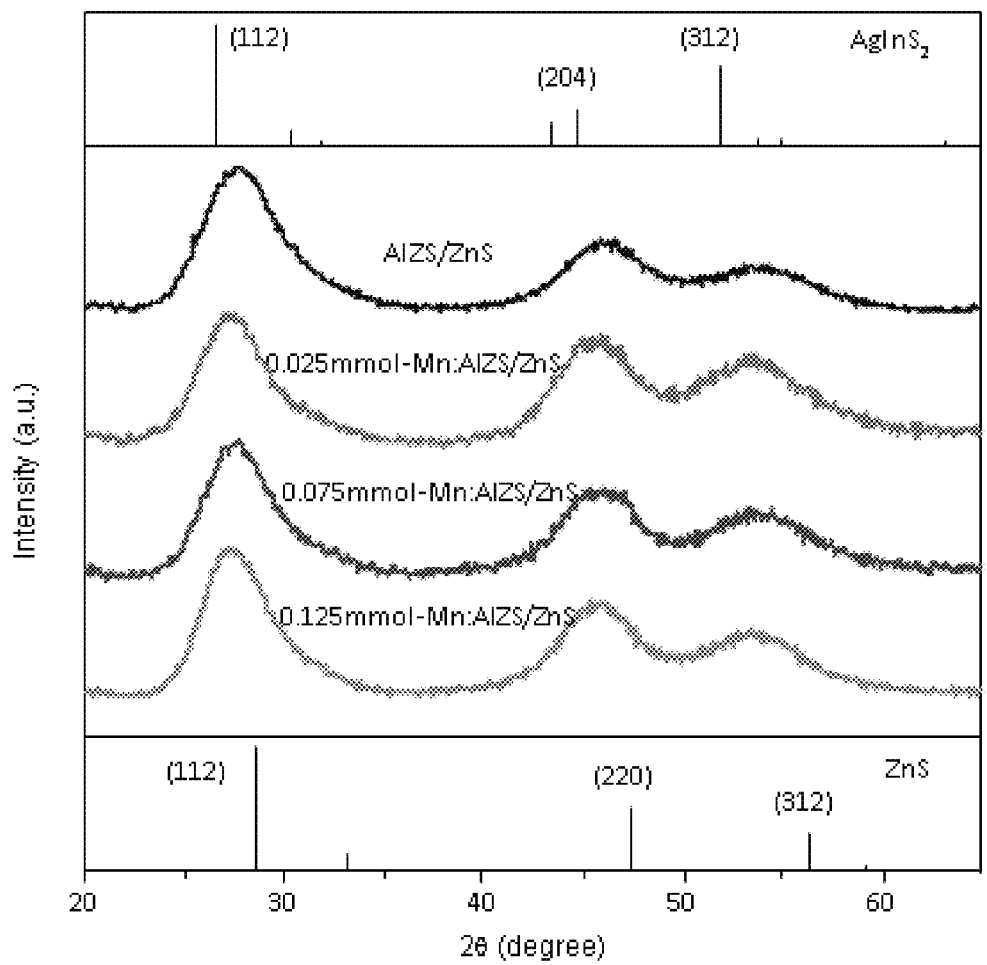
FIG. 46 illustrates XRD patterns of an undoped AIS/ZnS nanocrystal, a 0.025 mmol-Mn-doped AIS/ZnS nanocrystal, a 0.075 mmol-Mn-doped AIS/ZnS nanocrystal, and a 0.125 mmol-Mn-doped AIS/ZnS nanocrystal, wherein diffraction peaks of tetragonal AgInS₂ and ZnS, as obtained from the JCPDS database (specifically, JCPDS #25-1330 and JCPDS #05-0566), are shown as references.
Figure 47A:
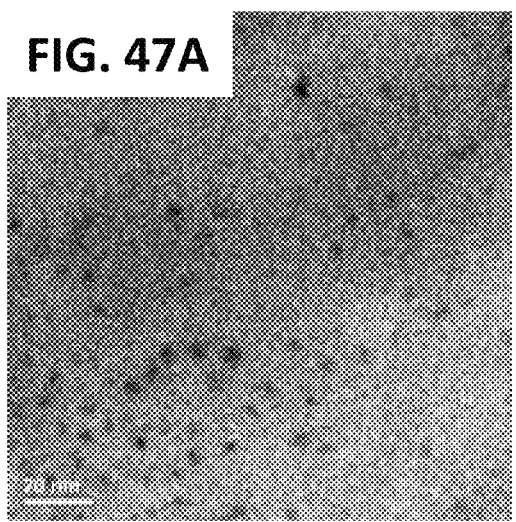
Figure 47B:
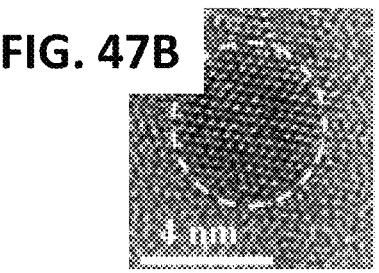
Figure 47C:
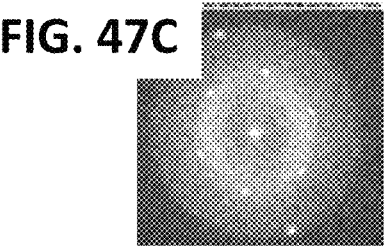
Figure 47D:
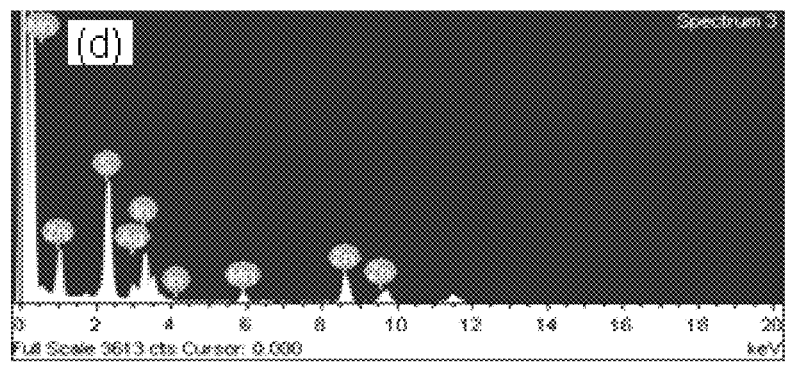
Figure 48:
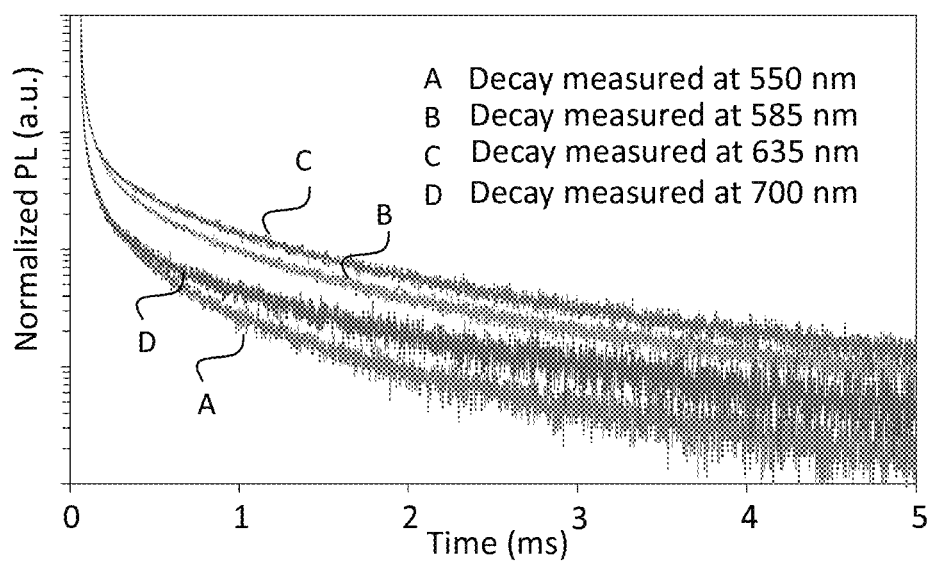
FIG. 48 is a graph illustrating photoluminescence decay curves of a 0.075 mmol-Mn-doped AIZS/ZnS nanocrystal, wherein the sample is excited at 300 nm by a xenon lamp and its photoluminescence decays were measured at different wavelengths.

In these examples, AIS quantum dots re synthesized using In(Ac)$_3$ and then are mixed with InCl$_3$ solution at 130° C. (InCl$_3$ dissolved in a mixture of oleic acid and 1-octadecene). The controls used as comparisons can be synthesized using In(Ac)$_3$ and then mixing with In(Cl)$_3$ solution at 130° C. ((In(Ac)$_3$ dissolved in a mixture of oleic acid and 1-octadecene). At 130° C., such a temperature will not trigger any reactions but promote the diffusion of chloride to quantum dot surfaces. In some examples, AIS QDs were synthesized using silver nitrate (0.1 mmol), In(Ac)$_3$ (0.2 mmol), 1-DDT (8 mL) and oleic acid (250 μL) at 175° C. Then, the quantum dot solution was cooled down from 175° C. and maintained at 130° C. under an Ar flow. 0.1 mmol InCl$_3$ or In(Ac)$_3$ was dissolved in a mixture of oleic acid and 1-octadecene at 130° C. 2.5 mL of InCl$_3$ or In(Ac)$_3$ solution was injected into the quantum dot solution for 60 min stirring. The quantum dot solutions were sampled for quantum yield measurements before and after the injection of InCl$_3$ or In(Ac)$_3$ solution. The data are illustrated graphically in FIGS. 44A and 44B, wherein FIG. 44A shows that with chloride treatment, the quantum dots reach around 40% enhancement, and FIG. 44B shows that without chloride treatment, the quantum yield of the quantum dots remains unchanged.

Synthesis of Mn-Doped AIZS/ZnS Composites

Ag(DDTC) (0.1 mmol), In(Ac)3 (0.2 mmol) and DDT (4 mL) were added into a 50 mL three-necked round bottom flask equipped with a condenser and a magnetic stir bar. The mixture was heated to 125° C. under vacuum until a clear solution was obtained, and to 200° C. under a flow of argon for 10 minute reaction. Then, 0.5 mL of Zn precursors (0.4 mmol zinc stearate in 4 mL of ODE) was added drop-wise into the AIS core solution to form AIZS nanocrystals. Afterwards, 0.25, 0.75 or 1.25 mL of Mn precursors, which were prepared by dissolving 0.1 mmol Mn(Ac)$_2$ in the mixture of 0.75 mL of ODE and 0.25 mL of OAm, were added drop-wise into the AIZS nanocrystal solution and the solution was maintained at 240° C. for 15 minutes. Subsequently, for the ZnS shell coating or nanocrystal surface etching by zinc, 2 mL of Zn precursors were slowly added drop-wise to the Mn-doped AIZS growth solution (cooled to 200° C.) and the solution was then maintained at 200° C. After the reaction was complete, the mixture was cooled down to room temperature. The Mn:AIZS/ZnS nanocrystals were purified repeatedly with the solvent combinations of hexane/ethanol and chloroform/acetone by centrifugation and then dried under vacuum. Undoped AIZS/ZnS nanocrystals were prepared in the way as described above but without any addition of Mn precursors. Results obtained from this example are shown in FIGS. 45A-45C, 46, 47A-47D, and 48.

Figure 49:
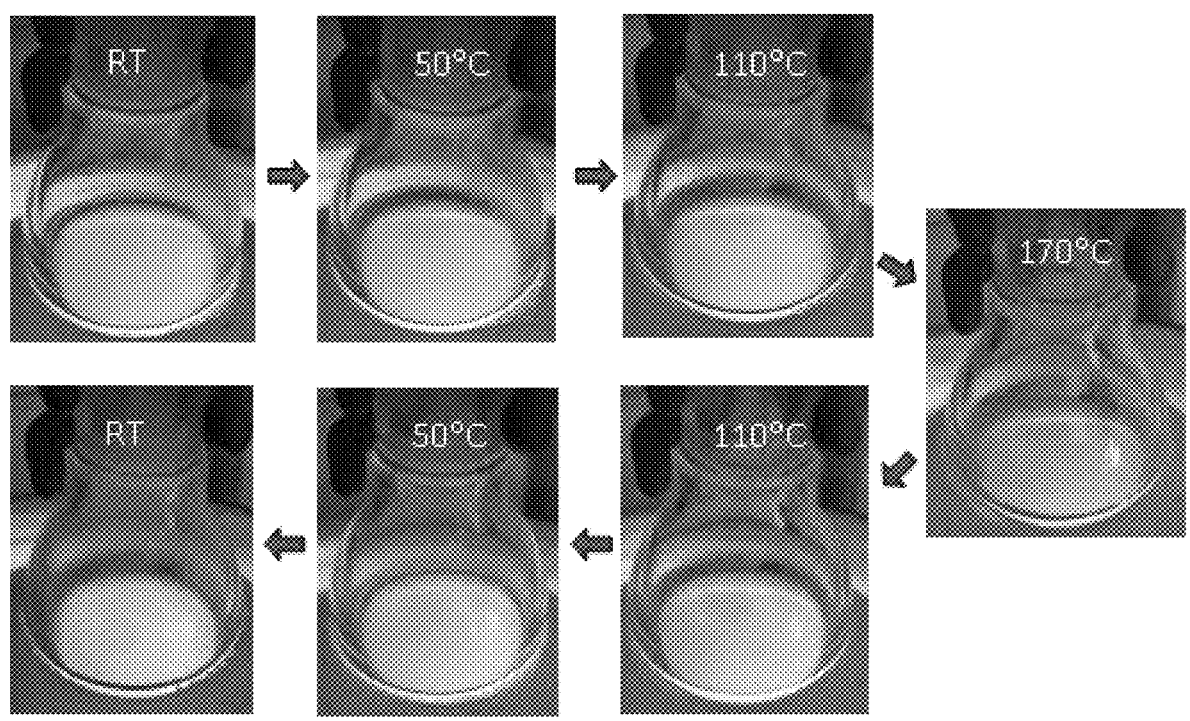
FIG. 49 is a collection of photographic images illustrating results obtained from a thermal stability study of Mn:AIZS/ZnS nanocrystal, wherein the Mn:AIZS nanocrystal solutions are shown at room temperature, after heating at 170° C., and cooled down to room temperature under a UV lamp.

Thermal stability study was performed on these Mn-doped ternary nanocrystals. A small amount of 0.075 mmol-Mn-doped AIZS/ZnS nanocrystals were dissolved in ODE and DDT (DDT is a native ligand coated on nanocrystals during synthesis, and it is thus here used as surfactant for nanocrystals). After vacuum and nitrogen filling, the solution was heated from room temperature (RT) to 170° C. and then back to room temperature. In this example, temperatures higher than 170° C. were avoided to avoid thermal decomposition of DDT. As shown in FIG. 49, after 50° C., the photoluminescence of the solution apparently fades with a slight blue-shift (towards yellow emission) in the time course of the temperature rising to 170° C. The photoluminescence (intensity and wavelength) of the solution recovers as the temperature is back to RT. This is a reversible photoluminescence quenching. Other two types of Mn:AIZS/ZnS nanocrystals were also tested and presented the similar behavior to that of 0.075 mmol-Mn:AIZS/ZnS nanocrystals. The results are illustrated in FIG. 49.

Figure 50A:
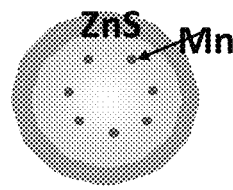
FIGS. 50A-50C are images illustrating results from analyzing a Mn-doped nanocrystal embodiment wherein the core of the nanocrystal is doped.
Figure 50B:
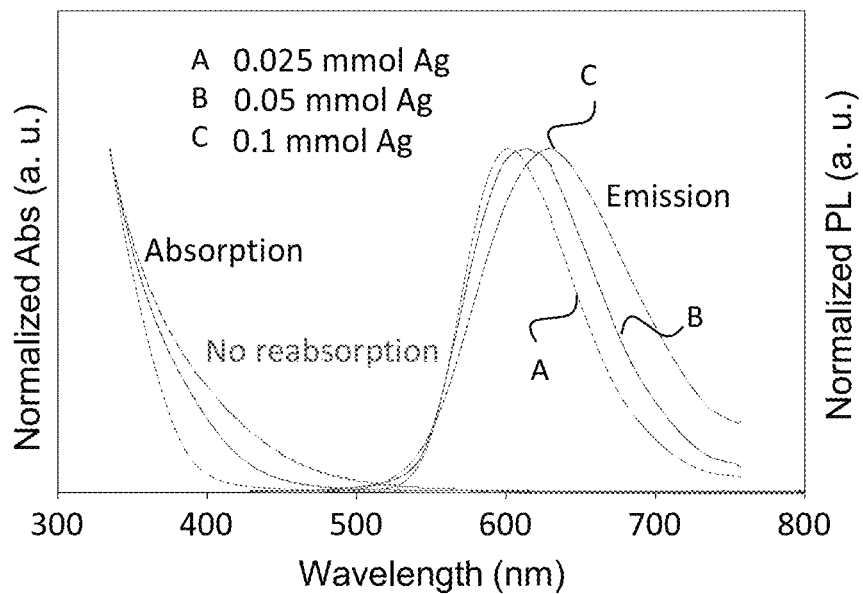
Figure 50C:
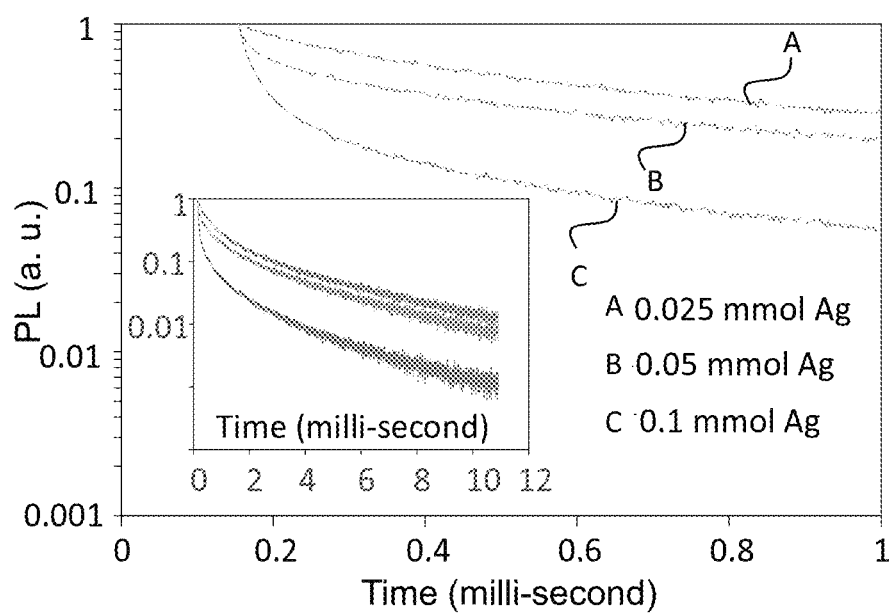

In another example, Mn-doped AZIS nanocrystals (schematically illustrated in FIG. 50A) were prepared using 0.2 mmol Zn precursor, 0.2 mmol In precursor, 0.025 mmol Mn precursor, 0.8 mmol sulfur precursor, and Ag precursor in the range of 0.025~0.1 mmol. After Mn atoms were doped into AZIS nanocrystals, a Zn precursor and sulfur precursor were added into the reaction flask to grow a ZnS shell on nanocrystals to form Mn-doped AZIS/ZnS nanocrystals. As references, AZIS/ZnS nanocrystals using the exact same conditions above but without any Mn precursors in synthesis were made. Results from analyzing nanocrystals formed in this example are shown in FIGS. 50B and 50C.

Figure 52:
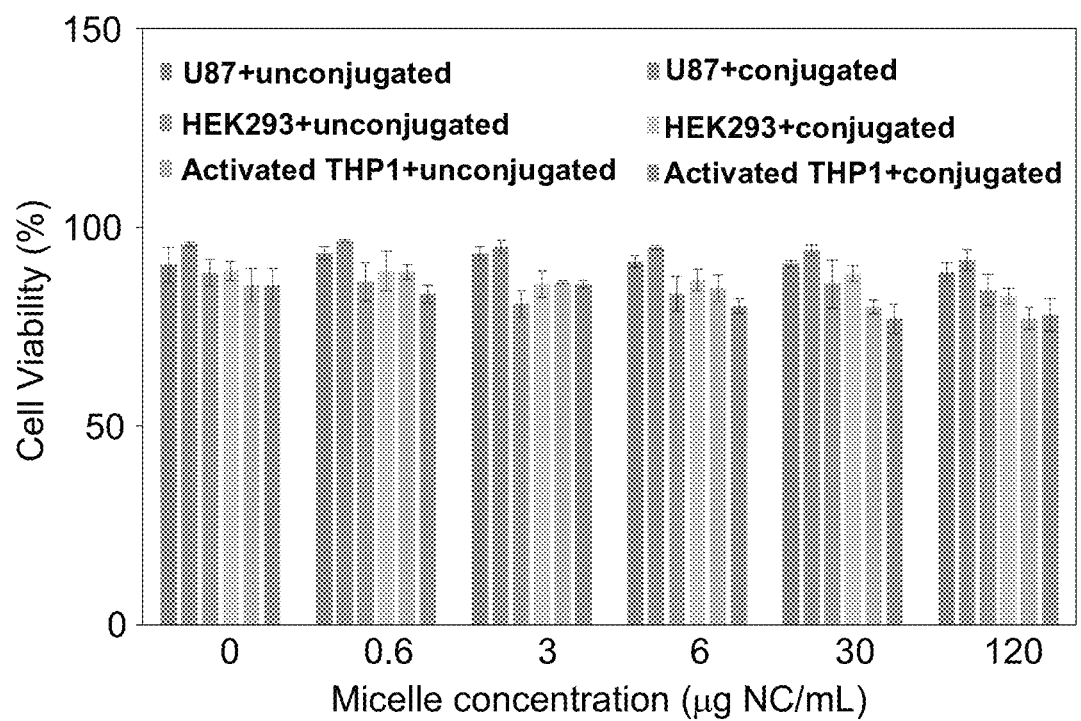
FIG. 52 is a graph illustrating results obtained from cell viability testing, wherein unconjugated and chlorotoxin-conjugated conjugates prepared using composite embodiments described herein were incubated with cells over 72 hours.

In this example, a composite comprising I(II)-III-VI nanocrystals was made having a composite structure similar to that illustrated schematically in FIG. 51A (though a person of ordinary skill in the art with the benefit of this disclosure recognizes that the synthesized composite may have more or fewer zwitterionic ligands that the four illustrated in FIG. 51A). The solution of 0.6 mg $MnFe_2O_4$ magnetic nanoparticles and 2.4 mg I(II)-III-VI nanocrystals in THF (900 μL) and 1.7 mg PMAO-CBSB in $CHCl_3$-MeOH (~50 μL) was layered on top of cold water in a glass vial. The mixture was ultrasonicated using the Misonix Ultrasonic Liquid Processor with a 5 W output power for 1 minute. After sonication, the organic solvents were removed by rotary evaporation at room temperature and the sample filtered through a 0.2 μm syringe filter. Empty micelles or single-nanoparticle based micelles were removed by centrifugation at 18,000 rpm for 25 min (twice). The collected ZW-MFNP conjugates were dispersed in 400 μL of water, and stored at 4° C. until further use. Representative magnetic resonance image and optical images obtained from such composites at difference concentrations are provided by FIG. 51B. In another example, composites were further coupled with chlorotoxin. As shown by FIG. 52, such conjugated composites are biocompatible with different cell lines (e.g., U87, HEK293, and activated THP1).

Figure 53A:
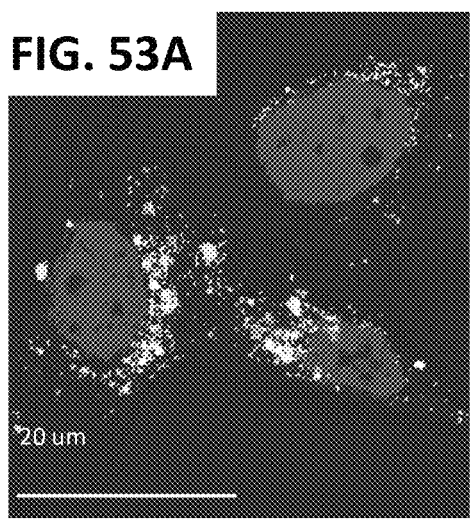
FIGS. 53A and 53B are images showing intracellular distribution of conjugated micelles in U-87, wherein micelles, endosomes or lysosomes are stained with Lysotracker green, and nuclei are stained with DAPI appear red, green, and blue, respectively.
Figure 53B:
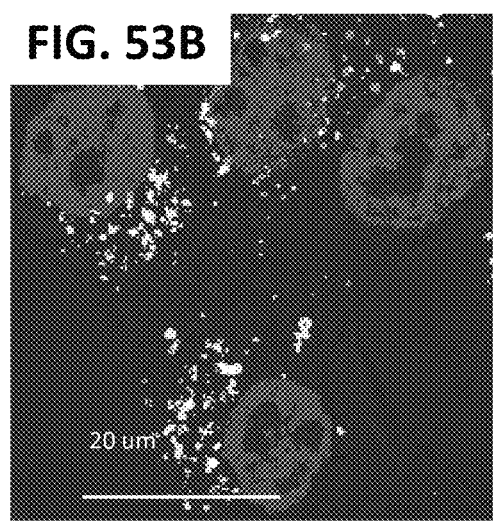

In another example, U87 cells were co-incubated with chlorotoxin-conjugated conjugates (7.2 mg NC/mL) and 1 mM LysoTracker (ex465/em535, a fluorescent marker from Invitrogen for secondary endosomes or lysosomes) for 3 hours and 24 hours, respectively. Afterward, U87 cells were fixed and stained with DPAI, and then scanned using confocal microscopy. Representative overlay images for 3 and 24 hr incubation times are shown in FIGS. 53A and 53B, respectively. Spot provided by these images represent micelles (smaller peripheral spots relative to the large spots), endosomes/lysosomes (smaller peripheral spots relative to the large spots) and nuclei (large spots). Also indicated in FIGS. 53A and 53B is the co-localization of micelles with endosomes/lysosomes. Such co-localization is qualitative, and it is affected by the intensity the different peripheral spots in these images. Mander's and Costes's methods, which are implemented in ImageJ as Plugin Coloc2, were used for colocalization analysis. These approaches are not affected by the intensity difference of two colors or probes, and automatically eliminate image backgrounds caused from autofluorescence, nonspecific labeling of dyes or markers, and probe fluorescence arising from out-of-focus image planes. With ImageJ, the colocalization ratio defined as (pixels of red)$_{colocalized}$/(pixels of red)$_{total}$ is found to be (0.78±0.25) for 3 hours incubation and (0.10±0.07) for 24 hours incubation, counting 10~20 cells to analyze the colocalization ratio (in some studies 10~20 cells were counted). This ratio indicates that the endosome/lysosome escape efficiency, which is defined as (1−colocalization ratio), is low in the early stage of micelle uptake by cells, but high with longer incubation times.

Table 3 lists the element atomic ratio for each investigated nanocrystals using EDX. With the increase of Mn levels in doping, the mole fractions of Mn atoms (Mn/(Ag+In+Zn+Mn+S)) that are incorporated in nanocrystals are increased—0.52%, 2.46%, and 2.96% for 0.025 mmol-, 0.075 mmol-, and 0.125 mmol-Mn-doped nanocrystals, respectively.

TABLE 3

| Nanocrystals | Measured Atomic Ratio by EDX | | | | |
|---|---|---|---|---|---|
| | Mn | Zn | Ag | In | S |
| AIZS/ZnS | — | 15.16 | 11.92 | 16.56 | 56.36 |
| 0.025 mmol-Mn:AIZS/ZnS | 0.52 | 21.48 | 10.71 | 18.70 | 48.60 |
| 0.075 mmol-Mn: AIZS/ZnS | 2.46 | 16.40 | 8.32 | 18.13 | 54.69 |
| 0.125 mmol-Mn:AIZS/ZnS | 2.96 | 19.56 | 12.99 | 13.46 | 51.05 |

As shown in Table 4, the fast and slow decays for 0.075 mmol-Mn:AIZS/ZnS nanocrystals are corresponding to $\tau_1$ at around 40 μs and $\tau_2$ at around 614 μs. These lifetimes are much longer than those of undoped AIZS/ZnS nanocrystals measured at their own photoluminescence peak wavelength. Moreover, the photoluminescence decays of 0.075 mmol-Mn:AIZS/ZnS nanocrystals measured at different wavelengths (550, 585, 700 nm) also present their own $\tau_1$ and $\tau_2$ in tens of microseconds and hundreds of microseconds. Without being limited to a single theory, it currently is believed that a thin layer of Mn was formed in host AIZS/ZnS nanocrystals, and that Mn clusters or concentrated Mn dopants may exist in this layer. Experimentally, photoluminescence quenching with Mn doping in nanocrystals was observed, which indicates Mn-related defect formation. The fast decay of 0.075 mmol-Mn:AIZS/ZnS nanocrystals could result from radiative decay from trap states (caused by Mn related lattice strains or defects) to the valence band. The trap states could be aligned or overlapping with Mn 3d states, so that excited electrons in conduction band could be relaxed to the trap states directly or through Mn 3d states as relay states. The fast decay of the nanocrystals also could be from the emission of Mn dopants but with Mn—Mn spin coupling due to concentrated Mn in the Mn-doped layer. Additionally, because the AIZS/ZnS nanocrystals act as host nanocrystals, the fast decay may also arise from alloying of Mn with AIZS/ZnS nanocrystals in a thin layer. That means, the new alloys may have new bandgap structures or electron-hole recombination paths. It is also possible that the photoluminescence of 0.075 mmol-Mn:AIZS/ZnS nanocrystals is a synergistic effect of various photoluminescence mechanisms. Notably, from Table 4, the intensity percentage of the slow decayed photoluminescence (i.e., A2) is low as several percent over the whole photoluminescence intensity.

Other nanocrystals with different Mn doping were measured in a similar way as 0.075 mmol-Mn:AIZS/ZnS nanocrystals. Their photoluminescence lifetime parameters are also listed in Table 4. The decay behavior of 0.125 mmol-Mn:AIZS/ZnS nanocrystals is very similar to that of 0.075 mmol-Mn:AIZS/ZnS nanocrystals. 0.025 mmol-Mn:AIZS/ZnS nanocrystals have smaller $\tau_1$ and A2 parameters compared to the other two types of nanocrystals, and thus they present short average photoluminescence lifetimes. According to Table 3, the Mn level in 0.025 mmol-Mn:AIZS/ZnS nanocrystals is much less than that in other two types of nanocrystals. The small $\tau_1$ and A2 for 0.025 mmol-Mn:AIZS/ZnS nanocrystals could be related to the low Mn level in the hosts. Interestingly, according to the literature, a lower Mn level in host nanocrystals should produce a longer photoluminescence lifetime probably because the Mn—Mn distance is long. Such a conflict indicates that the Mn emission with Mn—Mn coupling could be existing but not be the major photoluminescence mechanism for the fast decay (corresponding to $\tau_1$) in Mn:AIZS/ZnS nanocrystals. Without being limited to a single theory, it currently is believed that he radiative decay from trap states or new electron-hole recombination pathways in the Mn-alloyed AISZ layer could be the dominant mechanisms for the fast decayed photoluminescence. With respect to A2, it may be relative to the ratio of the number of Mn pairs or diluted Mn dopants out of the Mn-doped layer over the number of all Mn dopants (in and out of the Mn-doped layer). For a low level Mn (0.025 mmol) in the doping reaction, the Mn spatial distribution in nanocrystals could be more uniform by diffusion when compared to high Mn levels, and thus the ratio of the number of Mn dopants out of the doped layer over the number of Mn dopants in and out of the doped layer (or alternatively $A_2$) would be smaller. Notably, all prepared nanocrystals have their average photoluminescence lifetimes above one hundred microseconds, and they have good potential to be used as time-gated or time resolved probes in biosening/imaging.

TABLE 4

| Nanocrystals | Measured Wavelength | $\tau_1$ (ms) | $A_1$ | $\tau_2$ (ms) | $A_2$ | $\tau_{avg}$ (ms) |
|---|---|---|---|---|---|---|
| 0.025 mmol-Mn:AIZS/ZnS | 525 nm | 21.8 | 98.9% | 332.6 | 1.1% | 66.6 |
| | 575 nm | 30.1 | 98.1% | 280.0 | 1.9% | 67.5 |
| | 625 nm | 27.2 | 99.1% | 517.0 | 0.9% | 100.6 |
| | 700 nm | 17.5 | 99.8% | 498.9 | 0.2% | 39.9 |

TABLE 4-continued

| Nanocrystals | Measured Wavelength | $\tau_1$ (ms) | $A_1$ | $\tau_2$ (ms) | $A_2$ | $\tau_{avg}$ (ms) |
|---|---|---|---|---|---|---|
| 0.075 mmol-Mn:AIZS/ZnS | 550 nm | 33.0 | 97.0% | 311.1 | 3.0% | 95.3 |
| | 585 nm | 41.2 | 96.6% | 519.1 | 3.4% | 187.2 |
| | 635 nm | 40.1 | 96.0% | 614.2 | 4.0% | 263.5 |
| | 700 nm | 31.0 | 98.2% | 480.8 | 1.8% | 129.1 |
| 0.125 mmol-Mn:AIZS/ZnS | 550 nm | 33.4 | 97.8% | 321.1 | 2.2% | 85.1 |
| | 585 nm | 41.3 | 96.7% | 509.7 | 3.3% | 178.6 |
| | 642 nm | 42.8 | 96.8% | 496.4 | 3.2% | 169.4 |
| | 700 nm | 32.3 | 98.2% | 264.1 | 1.8% | 62.9 |

Figure 54A:
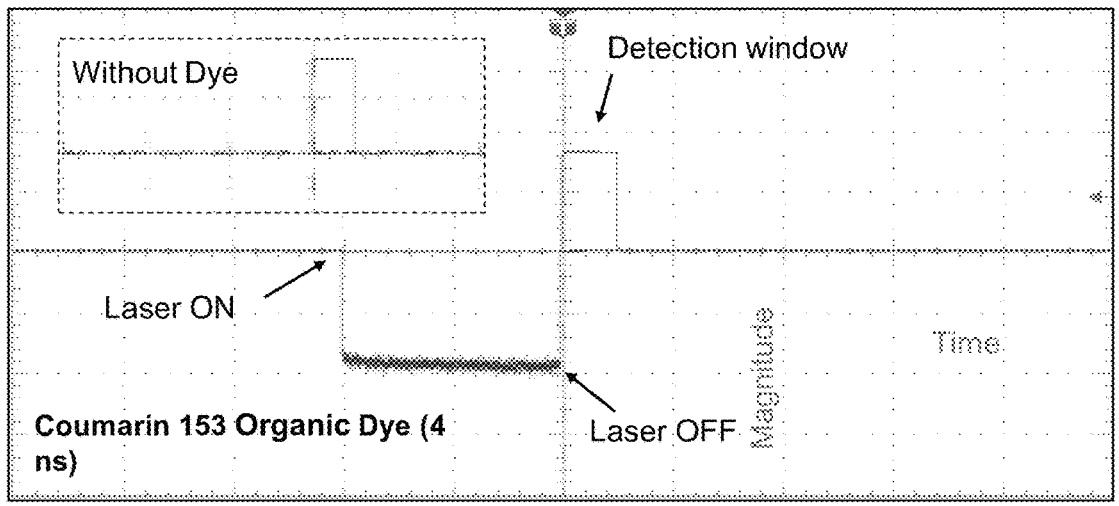
FIGS. 54A-54C shows results obtained from measuring the fluorescence lifetime of a control (organic dye C153) and two composite embodiments described herein, namely an Mn-doped AZIS/ZnS composite having an average lifetime of 0.1 ms (FIG. 54B) and another embodiment having an average lifetime of 1 ms (FIG. 54C), wherein the insets show the zero backgrounds.
Figure 54B:
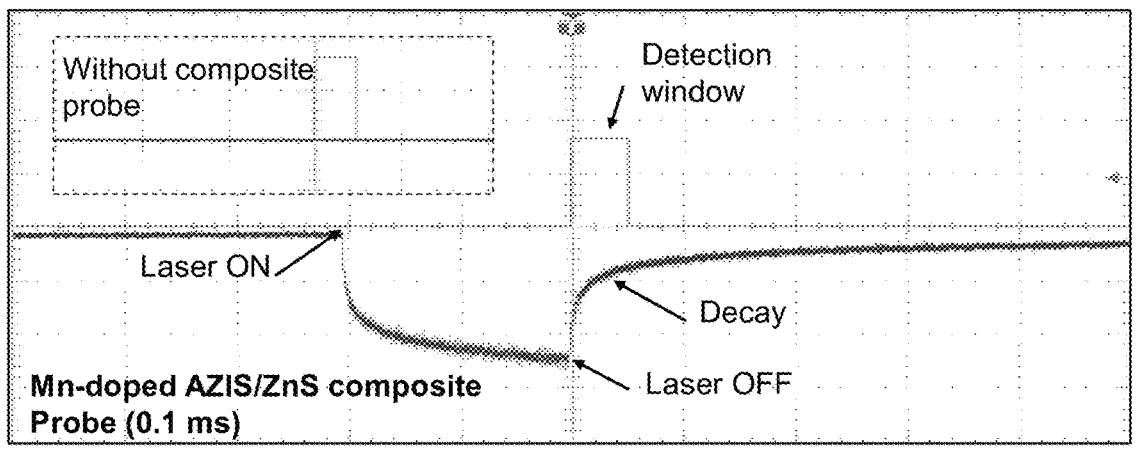
Figure 54C:
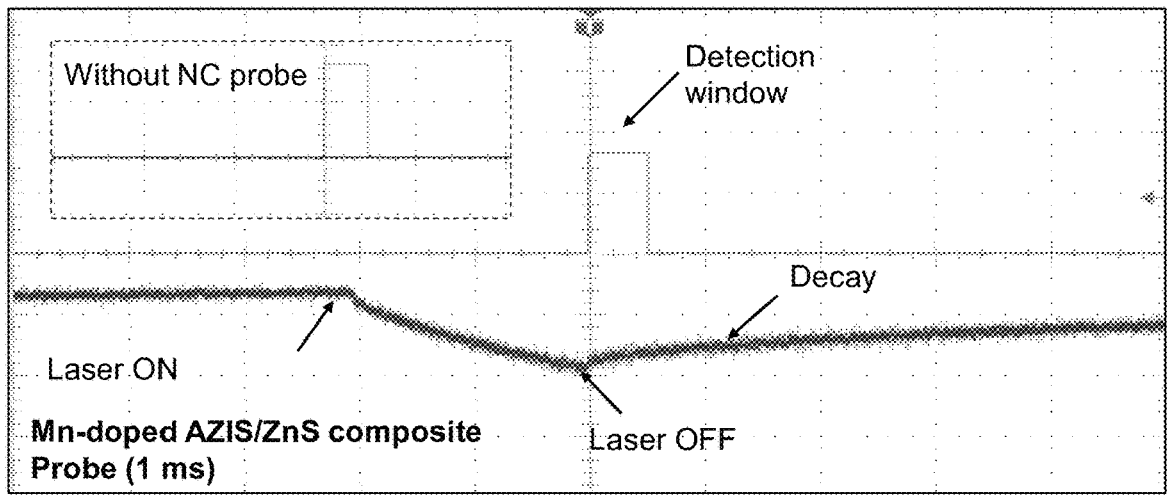

FIGS. 54A-54C include results obtained from analyzing the fluorescence lifetime of a control (organic dye Coumarin 153 in ethanol) and two Mn-doped composite embodiments of the present disclosure, which were prepared by encapsulating Mn-doped AZIS/ZNS nanocrystals (their average lifetimes at around 0.1 and 1 ms, respectively) with a zwitterionic polymeric coating as described herein. This data was obtained using an optical detection system, which was capable of measuring fluorescence above 520 nm.

In view of the many possible embodiments to which the principles of the present disclosure may be applied, it should be recognized that the illustrated embodiments are only preferred examples of the present disclosure and should not be taken as limiting the scope. Rather, the scope of the present disclosure is defined by the following claims. We therefore claim as our invention all that comes within the scope and spirit of these claims.

We claim:

1. A composite, comprising:
a core comprising one or more magnetic nanoparticles, one or more quantum dots, or a combination thereof; and
a zwitterionic polymeric coating defining the core and comprising a zwitterionic polymer having a structure satisfying a formula

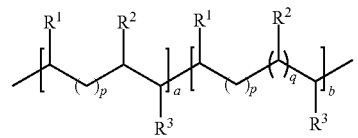

wherein each $R^1$ independently is hydrogen or aliphatic; each $R^2$ independently is —C(O)Z, wherein Z is hydroxyl, ether, amine, thiol, or thioether; at least one $R^3$ is amide-aliphatic-amine-aliphatic-carboxylate or amide-aliphatic-amine-aliphatic-sulfonate wherein the amine is positively charged, and each other $R^3$ independently is amide-aliphatic-amine, amide-aliphatic-amine-aliphatic-carboxylate, amide-aliphatic-amine-aliphatic-sulfonate, or amide-aliphatic-thiol; each p independently is an integer selected from zero to 5; q is an integer selected from zero or 1; and each of a and b independently is an integer selected from 1 to 200.

2. The composite of claim 1, wherein the zwitterionic polymeric coating comprises a zwitterionic polymer having a structure satisfying a formula selected from

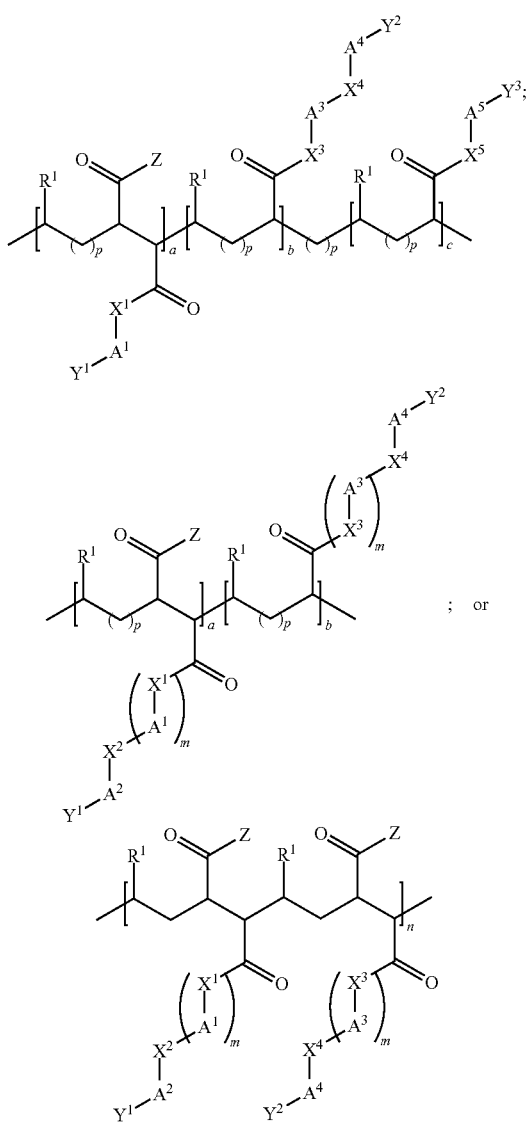

wherein each $R^1$ independently is hydrogen or aliphatic; each of $X^1$, $X^2$, $X^3$, $X^4$, and $X^5$ independently is $NR^b$, $N(R^b)_{2+}$, oxygen, or sulfur, wherein each $R^b$ independently is hydrogen, aliphatic, heteroaliphatic, aryl, or heteroaryl; each of $A^1$, $A^2$, $A^3$, $A^4$, and $A^5$ independently is aliphatic or heteroaliphatic; each of $Y^1$, $Y^2$, and $Y^3$ independently is amine, thiol, carboxylate or sulfonate; each Z independently is hydroxyl, ether, amine, thiol, or thioether; n is an integer selected from 1 to 200; each m independently is an integer selected from 0 to 3; each p independently is an integer selected from zero to 5; each of a, b, and c independently is an integer selected from 1 to 200.

3. The composite of claim 2, wherein each $R^1$ independently is hydrogen, alkyl, alkenyl, or alkynyl; each of $X^1$, $X^2$, $X^3$, $X^4$, and $X^5$ independently is $NR^b$, $N(R^b)_{2+}$, oxygen, or sulfur, wherein each Rb independently is hydrogen, alkyl, alkenyl, alkynyl, heteroalkyl, heteroalkenyl, heteroalkynyl, phenyl, naphthyl, or pyridinyl; each of $A^1$, $A^2$, $A^3$, $A^4$, and $A^5$ independently is alkyl, alkenyl, alkynyl, heteroalkyl, heteroalkenyl, or heteroalkynyl; each of $Y^1$ and $Y^2$ independently is carboxylate or sulfonate and $Y^3$ is thiol; each Z is hydroxyl; and m is 1.

4. The composite of claim 1, wherein the zwitterionic polymeric coating comprises a zwitterionic polymer have a structure selected from

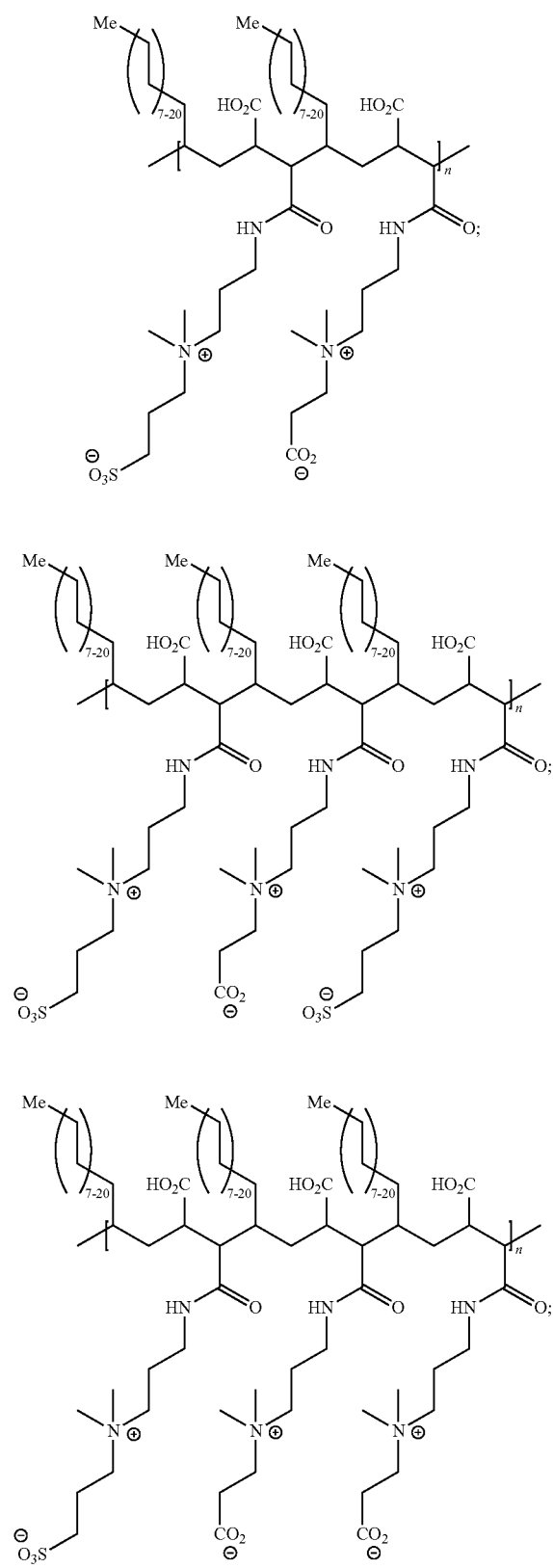

-continued

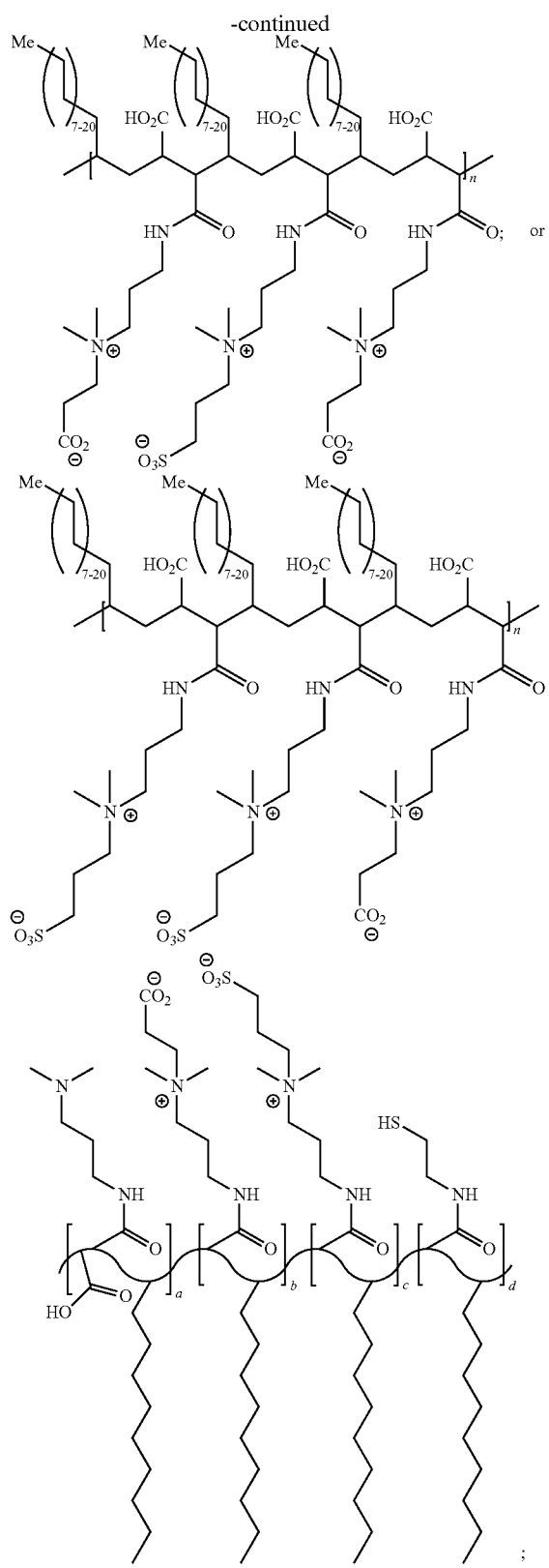

wherein d is an integer selected from 1 to 200.

5. The composite of claim 1, wherein the core comprises at least one magnetic nanoparticle and at least one quantum dot.

6. The composite of claim 1, wherein the core is doped with a metal selected from Cu, Ag, Au, Mn, Zn, or combinations thereof and wherein the core is doped with greater than 0 mol % to 10 mol % of the metal.

7. The composite of claim 6, wherein the core is a I-II-VI quantum dot core and the quantum dot core comprises a ZnS or a chloride shell.

8. The composite of claim 1, wherein the magnetic nanoparticle is $MnFe_2O_4$, $Fe_3O_4$, $CoFe_2O_4$, FePt or a combination thereof.

9. The composite of claim 1, wherein the core comprises a combination of $MnFe_2O_4$ nanoparticles and an $AgInS_2$ quantum dot, a $CuInS_2$ quantum dot, or a combination thereof.

10. The composite of claim 1, comprising:
a core comprising a combination of $MnFe_2O_4$ nanoparticles and $CuInS_2$ quantum dots, $AgInS_2$ quantum dots, or both $CuInS_2$ quantum dots, $AgInS_2$ quantum dots; and
a zwitterionic polymeric coating comprising a zwitterionic polymer having a structure selected from

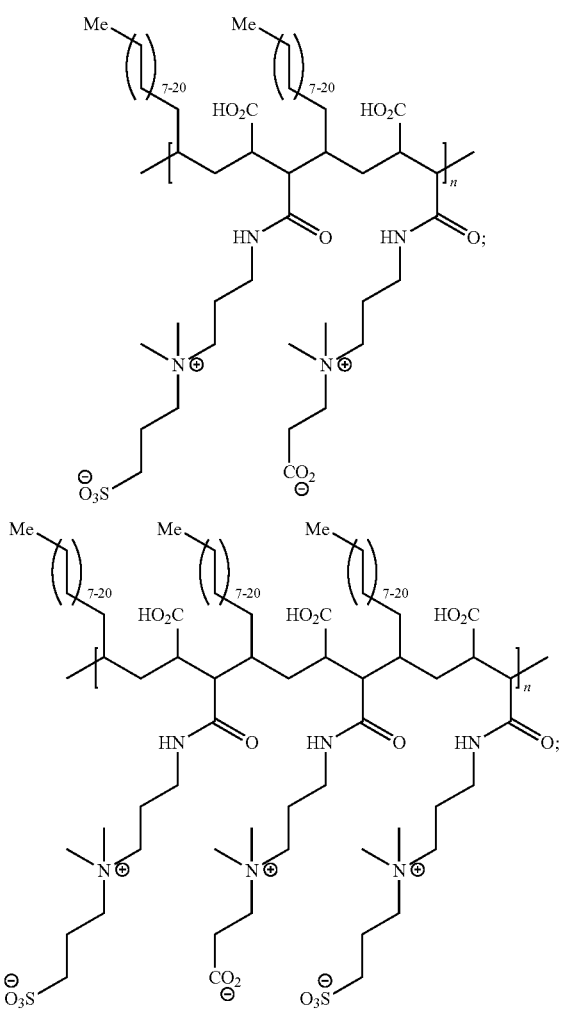

-continued

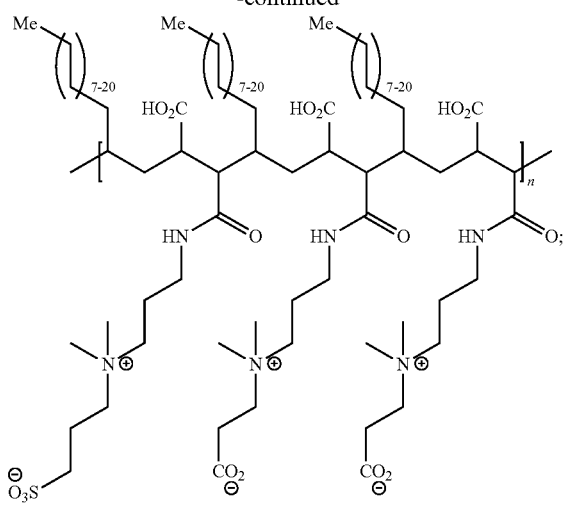

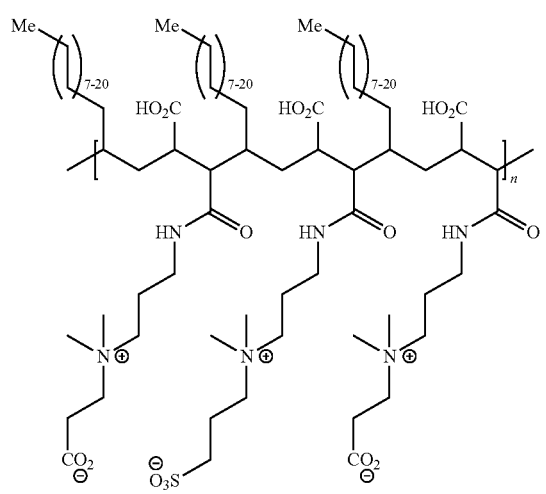

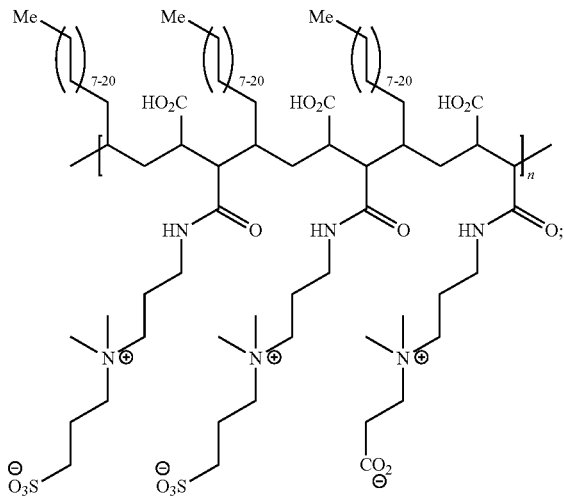

or

-continued

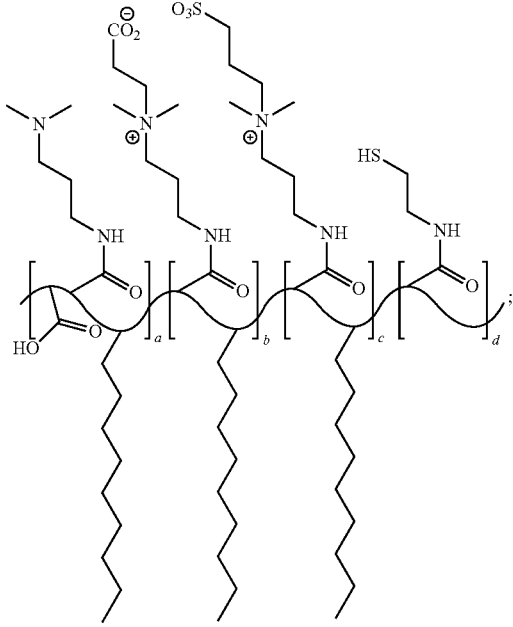

wherein d is an integer ranging from 1 to 200.

11. The composite of claim 10, wherein the core further comprises a dopant selected from Cu, Ag, Au, Mn, Zn, or combinations thereof, a ZnS or chloride shell, or both the dopant and the ZnS or chloride shell.

12. A composition comprising:
a composite having a core comprising one or more magnetic nanoparticles, one or more quantum dots, or a combination thereof and a zwitterionic polymeric coating comprising a zwitterionic polymer having a structure satisfying a formula

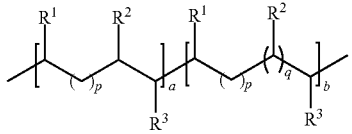

wherein each $R^1$ independently is selected from hydrogen or aliphatic; each $R^2$ independently is —C(O)Z, wherein Z is selected from hydroxyl, ether, amine, thiol, or thioether; at least one $R^3$ is amide-aliphatic-amine-aliphatic-carboxylate or amide-aliphatic-amine-aliphatic-sulfonate wherein the amine is positively charged, and each other $R^3$ independently is selected from amide-aliphatic-amine, amide-aliphatic-amine-aliphatic-carboxylate, amide-aliphatic-amine-aliphatic-sulfonate, or amide-aliphatic-thiol; each p independently is an integer selected from zero to 5; q is an integer selected from zero or 1; and each of a and b independently is an integer selected from 1 to 200; and
a biomolecule, a drug, or a combination thereof.

13. The composition of claim 12, wherein the biomolecule is chemically conjugated to the composite through the zwitterionic polymeric coating or through a carboxylate group of the zwitterionic polymeric coating.

14. The composition of claim 13, wherein the carboxylate group of the zwitterionic polymeric coating is further chemically bound to a linker, wherein the linker is also chemically bound to the biomolecule.

15. The composition of claim 12, wherein the biomolecule is selected from chlorotoxin, avidin, biotin, folic acid, arginylglycylaspartic acid, or combinations thereof.

16. The composition of claim 12, wherein the drug is encapsulated within the zwitterionic polymeric coating and is selected from doxorubicin, daunorubicin, epirubicin, idarubicin, or a combination thereof.

17. A method of making the composite of claim 1, comprising:
  combining, to form a mixture, a solution comprising the one or more magnetic nanoparticles, the one or more quantum dots, or the combination thereof with a solution of the zwitterionic polymer;
  dispersing the mixture into water using sonication to form a dispersed composition; and
  isolating the composite from the dispersed composition.

18. A method for imaging cells, comprising:
  contacting a cell with the composite of claim 1; and
  detecting cellular update and/or the location of the composite in the cell.

19. A method of delivering a therapeutic drug to a subject, comprising contacting the subject with a therapeutically effective amount of a composition comprising the therapeutic drug and the composite of claim 1.

* * * * *